(12) United States Patent
Wang et al.

(10) Patent No.: US 8,524,947 B2
(45) Date of Patent: Sep. 3, 2013

(54) ACYLSULFONAMIDES AND PROCESSES FOR PRODUCING THE SAME

(75) Inventors: Hong-Gang Wang, Palmyra, PA (US); Roman Manetsch, Tampa, FL (US); Xiangdong Hu, Xi'an (CN); Sameer Kulkarni, Tampa, FL (US); Jiazhi Sun, Tampa, FL (US)

(73) Assignees: University of South Florida, Tampa, FL (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 269 days.

(21) Appl. No.: 12/867,812

(22) PCT Filed: Feb. 23, 2009

(86) PCT No.: PCT/US2009/034869
§ 371 (c)(1),
(2), (4) Date: Feb. 14, 2011

(87) PCT Pub. No.: WO2009/105751
PCT Pub. Date: Aug. 27, 2009

(65) Prior Publication Data
US 2011/0130568 A1    Jun. 2, 2011

Related U.S. Application Data

(60) Provisional application No. 61/030,756, filed on Feb. 22, 2008, provisional application No. 61/030,753, filed on Feb. 22, 2008.

(51) Int. Cl.
*C07C 321/00* (2006.01)
*C07D 217/02* (2006.01)
*C07D 211/06* (2006.01)
*C07D 277/00* (2006.01)

(52) U.S. Cl.
USPC ............ 564/85; 546/144; 546/206; 548/200

(58) Field of Classification Search
USPC .................. 564/85; 546/144, 206; 548/200
See application file for complete search history.

(56) References Cited

U.S. PATENT DOCUMENTS
2005/0215819 A1*  9/2005  Williams ................. 564/133

OTHER PUBLICATIONS

Hu et al. J. Am. Chem. Soc. 2008, 130, 13820-13821.*
Patent Cooperation Treaty, International Search Report issued for PCT/US2009/034869, mailed Jul. 29, 2009, 4 pages.
Kolakowski, R. V. et al., Mechanism of Thio Acid/Azide Amidation, Journal of the American Chemical Society, 2006, 128(17), pp. 5695-5702.
Shangguan, N. et al., The Reaction of Thio Acids with Azides: A New Mechanism and New Synthetic Applications, Journal of the American Chemical Society, 2003, 125(26), pp. 7754-7755.
Bretschneider, H. et al, New reactions on sulfanilamide and new N-substituted sulfanilamides. 1. Nl-acylation with carboxylic acid esters, Monatshefie fuer Chemie, 1956,87, pp. 47-59, ISSN: 0026-9247.

* cited by examiner

*Primary Examiner* — Nizal Chandrakumar
(74) *Attorney, Agent, or Firm* — Bryan Cave LLP

(57) ABSTRACT

The present disclosure relates to acylsulfonamides and processes for their preparation. The processes involve a target-guided synthesis approach, whereby a thioacid and a sulfonyl azide are reacted in the presence of a biological target protein, a Bcl-2 family protein, to form the acylsulfonamide.

19 Claims, 19 Drawing Sheets

FIG. 1
Ribbon structure of Bcl-X$_L$-Bak complex.
Surface representation of the binding pocket of Bcl-X$_L$ bound to the Bak peptide.

Fig. 7
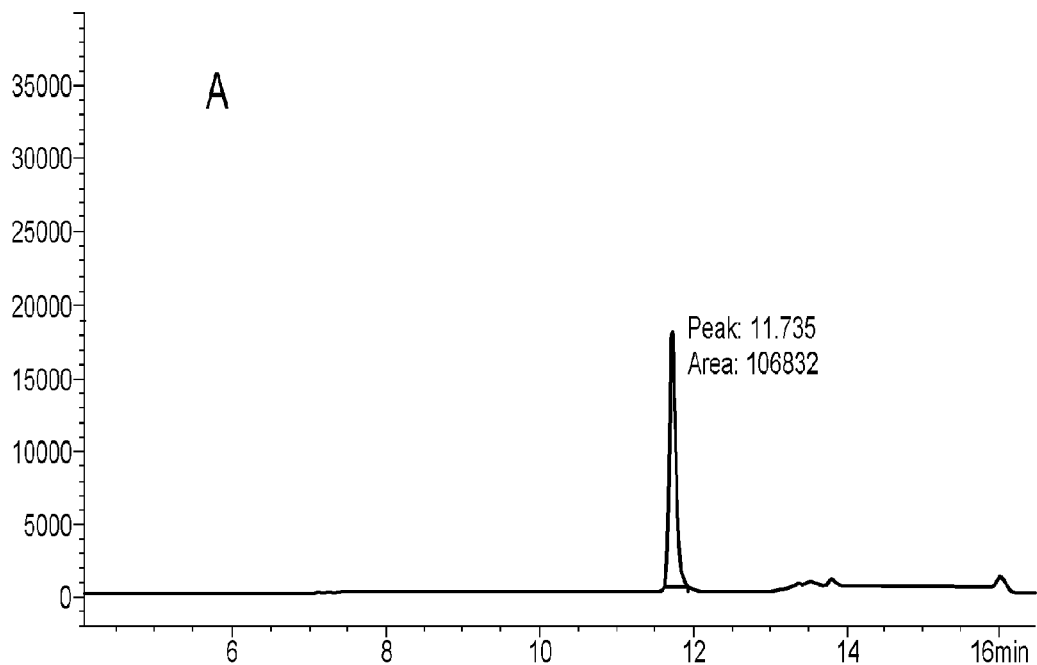
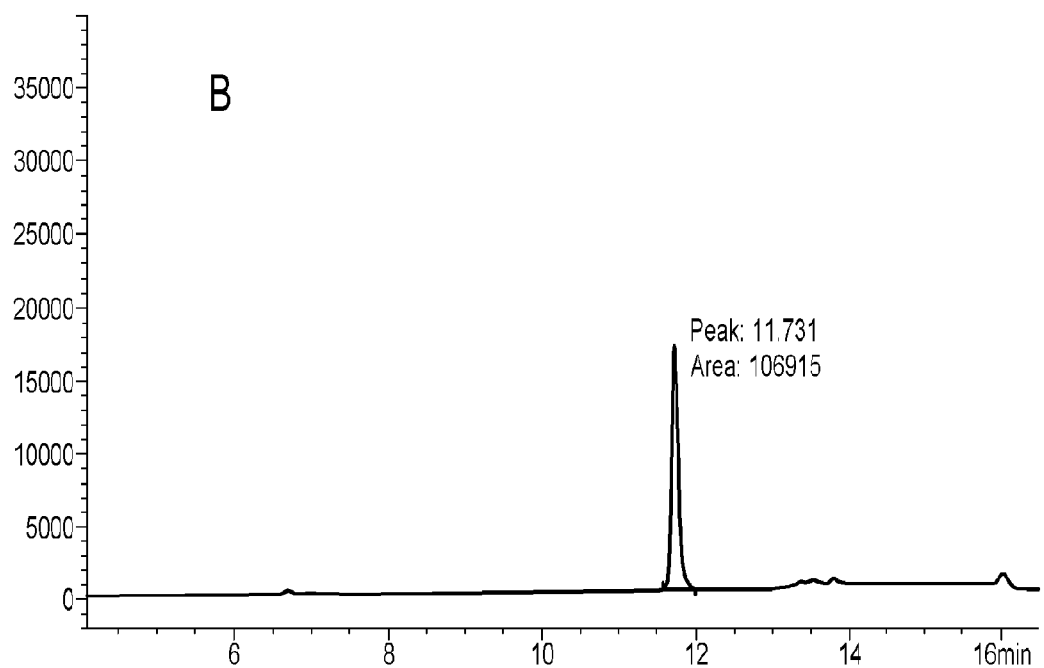

ACYLSULFONAMIDES AND PROCESSES FOR PRODUCING THE SAME

CROSS-REFERENCE TO RELATED APPLICATIONS

This application claims the benefit of U.S. Provisional Application Ser. Nos. 61/030,753 and 61/030,756, filed Feb. 22, 2008, which are hereby incorporated by reference in their entirety, including any figures, tables, and drawings.

STATEMENT OF GOVERNMENT RIGHTS

This invention was made with government support under Grant No. P01 CA118210 awarded by the National Institutes of Health. The government has certain rights in the invention.

BACKGROUND

The present disclosure generally relates to acylsulfonamides and processes for their preparation. The disclosure also relates to a kinetically controlled target-guided synthesis approach for the discovery and development of small molecules.

Combinatorial chemistry and parallel synthesis are the tools commonly utilized for lead compound identification and optimization. However, even though in the last two decades combinatorial chemistry and parallel synthesis have gone hand in hand with the dramatic advances of technology for rapid production, handling and screening of large numbers of compounds, they are often accompanied by challenges such as the efficiency of library synthesis, the purity of each library member, and the unambiguous identification of lead compounds in the screening of each library member against a particular biological target. In the last decade, fragment-based lead compound discovery or target-guided synthesis (TGS) approaches have been developed in which the biological target is actively engaged in the design and the synthesis of its own enzyme inhibitory compounds. To date, target-guided synthesis has exclusively been applied for enzymatic targets only. See, e.g., Manetsch et al., Journal of the American Chemical Society 2004, 126, 12809-12818; Sharpless et al., Expert Opin. Drug Discovery 2006, 1, 525-538; and Kolb et al., U.S. Patent Publication No. 2006/0269942.

Among a variety of proteins, the Bcl-2 family of proteins, which consists of both anti- and pro-apoptotic molecules, in particular, can play an important role in the regulation of the intrinsic (mitochondrial) pathway of apoptosis. The anti-apoptotic Bcl-2 family proteins (e.g., Bcl-2, Bcl-$X_L$, Mcl-1) inhibit the release of certain pro-apoptotic factors from mitochondria, whereas pro-apoptotic Bcl-2 family members, which can be further separated into two subgroups, the multidomain BH1-3 proteins (Bax and Bak) and the BH3-only proteins (e.g., Bad, Bim, and Noxa), induce the release of mitochondrial apoptogenic molecules into the cytosol. Although the precise biochemical mechanisms by which Bcl-2 family proteins exert their influence on cell life and death remains far from clear, the relative ratios of pro- and anti-apoptotic Bcl-2 family proteins determine the ultimate sensitivity or resistance of cells to a wide variety of apoptotic signals.

Evidence has accumulated that the majority of human cancers overexpress the pro-survival Bcl-2 family proteins, which not only contribute to cancer progression by preventing normal cell turnover, but also render cancer cells resistant to current cancer treatments. For example, high levels of Bcl-2 are found in ~30% to 60% of prostate cancer, ~60% to 90% of breast cancer, ~20% to 40% of non-small cell lung cancer, ~60% to 80% of small cell lung cancer, ~50% to 100% of colorectal cancer, ~65% of melanoma, ~30% of neuroblastomas, and ~80% of B cell lymphomas. Similarly, Bcl-$X_L$ is overexpressed in ~100% of hormone-refractory prostate cancer, ~40% to 60% of breast cancer, ~80% of colorectal cancer, ~90% of melanoma, ~90% of pancreatic cancer, and ~80% of hepatocellular carcinoma. It has been shown that overexpression of Bcl-2 and/or Bcl-$X_L$ renders cancer cells resistant to most of the currently available chemotherapeutic drugs as well as radiation therapy. Therefore, it is an attractive strategy to design and develop a new class of anticancer drugs that specifically target the anti- and pro-apoptotic functions of the Bcl-2 family proteins.

SUMMARY OF THE DISCLOSURE

Among the various aspects of the present disclosure is the provision of a target-guided synthesis approach for the discovery and development of small molecules, and in particular acylsulfonamides.

Briefly, therefore, the present disclosure is directed to a process for the preparation of an acylsulfonamide (3), the process comprising reacting a thioacid (1) with a sulfonyl azide (2) in the presence of a protein of the Bcl-2 family, wherein the thioacid (1), the sulfonyl azide (2), and the acylsulfonamide (3) correspond to Formulae (1), (2), and (3):

(1)

(2)

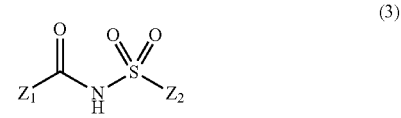

(3)

$Z_1$ is hydrocarbyl, substituted hydrocarbyl, heteroaryl, or heterocyclo; and $Z_2$ is hydrocarbyl, substituted hydrocarbyl, heteroaryl, or heterocyclo.

Another aspect of the disclosure is directed to an acylsulfonamide (3) having the formula:

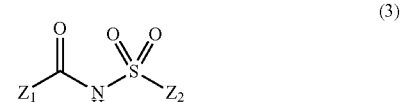

(3)

wherein
$Z_1$ has the formula:

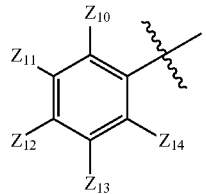

$Z_2$ has the formula:

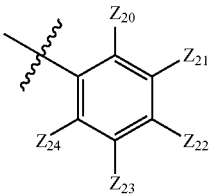

$Z_{11}$ and $Z_{13}$ are alkyl, substituted alkyl, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo, among others, wherein each occurrence of R$_Z$ is substituted or unsubstituted alkyl, substituted or unsubstituted aryl, or substituted or unsubstituted aralkyl;

$Z_{22}$ is —N($Z_{220}$)($Z_{221}$) or —CH$_2$—N($Z_{220}$)($Z_{221}$), wherein $Z_{220}$ and $Z_{221}$ are independently hydrogen, alkyl, substituted alkyl, aryl, substituted aryl, or $Z_{220}$ and $Z_{221}$ together with the nitrogen atom to which they are attached, form a substituted or unsubstituted alicyclic, bicyclic, aryl, or heterocyclic moiety; and $Z_{10}$, $Z_{12}$, $Z_{14}$, $Z_{20}$, $Z_{21}$, $Z_{23}$, and $Z_{24}$ are hydrogen.

Other aspects and features will be in part apparent and in part pointed out hereinafter.

BRIEF DESCRIPTION OF THE DRAWINGS

FIG. 1 illustrates the ribbon structure of a Bcl-X$_L$-Bak complex and the surface representation of the binding pocket of Bcl-X$_L$ bound to the Bak peptide.

FIG. 7 is an LC/MS trace illustrating the incubations of (SZ4) and (TA2) with Bak BH3 peptide for 24 hours. A) Incubation of (SZ4) and (TA2) without Bcl-X$_L$ or Bak BH3 peptide; B) Incubation of (SZ4) and (TA2) with 20 μM Bak BH3 peptide and without no Bcl-X$_L$.

DETAILED DESCRIPTION

Among other things, the present disclosure relates to a fragment-based lead compound discovery method, in which the biological target, e.g., a member of the Bcl-2 family of proteins, is directly involved in the assembly of its own bidentate ligand from two or more smaller reactive fragments or scaffolds. The methods described herein are versatile target-guided synthesis approaches for probing adaptive regions on/in biological targets, and in particular Bcl-2 family protein targets, and can be exploited as an innovative means to identify and optimize small molecules interacting with such biological targets. The target-guided synthesis methods are successful, in part, due to: (a) the nature of the chemical reaction combining the two fragments or scaffold compounds into a single molecule; and (b) the use of reactive fragments showing low to high affinity towards binding pockets or surfaces of the biological targets.

Another key component of the processes described herein is the reactivity of the utilized reactions; specifically, the functionalities on the building block or scaffold compounds can be tuned not only to the particular biological target, but also to speed up or slow down reactivity with the biological target, improving the formation of bidentate ligand(s) displaying good affinity to the biological target. Among other things, the processes described herein address certain limitations of the target-guided synthesis methods reported thus far; compared to the reported target-guided synthesis methods for the screening of enzymes, the discovery of protein interactions is more challenging because biological target/interfaces have relatively shallow binding sites on their surfaces, thus permitting only weak binding affinity for reactive fragments. This often translates to short residence times for these fragments within the binding cavities. For these and other reasons, previously reported target-guided synthesis methods poorly succeed or even fail in discovery attempts.

Figure 3:
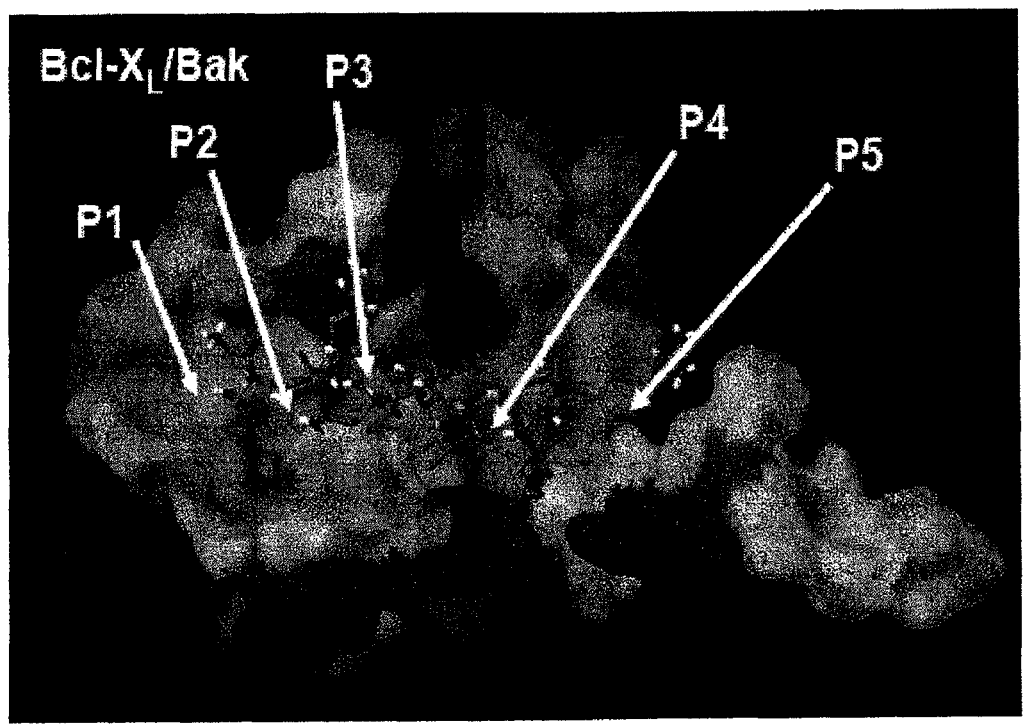
FIG. 3 illustrates the binding pockets of the Bcl-X$_L$-Bak complex.

As noted above, the processes described herein utilize certain structural moieties or scaffolds having activity against Bcl-2 family protein interactions (also referred to as protein-protein interaction modulation (PPIM)). PPIM activity can be achieved as described herein by compound design including one or two of the aforementioned structural moieties in the same compound. Each scaffold portion is designed to bind to one or more subpockets of a biological target, e.g., a Bcl-2 family protein. In a particular embodiment, the compounds prepared by the target-guided synthesis methods described herein are acylsulfonamide compounds that are capable of binding to one or more of the subpockets of a Bcl-2 family (e.g., Bcl-$X_L$, the binding subpockets of which are designated as P1, P2, P3, P4, and P5) (see, e.g., FIG. 3)). In a particular embodiment, the acylsulfonamide compounds target the P4 and/or P5 region of Bcl-$X_L$.

Compared to the previously reported target-guided synthesis screening methods for enzyme inhibitors, the target-guided synthesis approaches described herein utilize reactions with superior reactivity profiles, enabling the use of traditionally weak affinity small molecules as relatively reactive fragments for the discovery and optimization of ligands and compounds. The enhanced reactivity is due, in part, to the use of more reactive functionalities for the chemical reaction(s) that combines the two fragments into a larger molecule.

Among other things, the present disclosure relates to the preparation of acylsulfonamides. According to the processes described herein, at least one (and typically two or more) thioacid is incubated or reacted with at least one (and typically two or more) sulfonyl azide in the presence of a protein of the Bcl-2 family to form an acylsulfonamide. In certain embodiments, the protein is Bcl-$X_L$. In certain other embodiments, the protein is Mcl-1. In general, the reaction involves an amidation reaction between electron-poor thioacids and sulfonyl azides or between thioacids and electron-rich sulfonyl azides. See, e.g., Shangguan et al. J. Am. Chem. Soc. 2003, 125, 7754-7755.

The acylsulfonamide-forming reaction described herein is generally illustrated in Reaction Scheme (1), wherein $Z_1$ and $Z_2$ are described in connection with Formulae (1), (2), and (3) below:

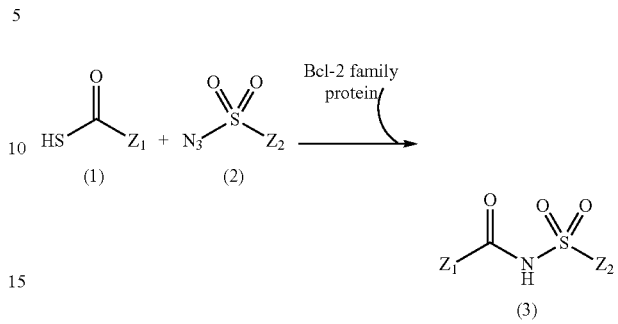

As shown, the thioacid (1) is reacted with a sulfonyl azide (2) in the presence of a Bcl-2 family protein. Usually, the reaction involves a pool or library of two or more thioacids (1), and a corresponding pool or library of two or more sulfonyl azides (2). The reaction is typically carried out at relatively ambient or slightly higher temperatures, which enhances the rate of the ligation reaction. The acylsulfonamide-forming reaction is typically carried out at a temperature of at least 20° C., preferably at least 25° C., and more preferably 30-40° C. Reaction times can range from about 1 hour to several days; e.g., from about 1 hour to about 48 hours (e.g., 6-12 hours, 12-36 hours, or 24-72 hours).

The reaction mixture for preparing the acylsulfonamide (3) according to the methods described herein typically comprises the thioacid (1) (or a library thereof), the sulfonyl azide (2) (or a library thereof), the biological target, and an aqueous buffer medium, which may be optimized depending on the particular thioacid(s) (1), sulfonyl azide(s) (2), and Bcl-2 family protein selected for the reaction. Preferably, the buffer is an aqueous physiological buffer that is compatible with biological materials. Buffers useful in the preparation of acylsulfonamides according to the processes described herein include but are not limited to phosphate-, citrate-, sulfosalicylate-, and acetate-based buffers, or other organic acid-based buffers. Still other buffers include ADA buffer, ACES buffer, BES buffer, BIS TRIS buffer, DIPSO buffer, HEPES buffer, MOPS buffer, MOPSO buffer, PIPES buffer, TES buffer, Tris buffer, Tricine buffer, TRISMA buffer, and the like. A more complete list can be found in the United States Pharmacopeia. In one embodiment, the buffer is a phosphate buffer (e.g., sodium phosphate, potassium phosphate). In certain preferred embodiments the buffering agent will be present in an amount sufficient to provide a pH ranging from about 6.0 to 9.5, more preferably pH 7.4. Other agents that may be present in the buffer medium include chelating agents, such as EDTA, EGTA, and the like.

Thioacids

In accordance with the present methods, a thioacid (or a library of thioacids) is reacted with a sulfonyl azide (or a library of sulfonyl azides) in the presence of a biological target molecule; in preferred embodiments, the biological target molecule is a Bcl-2 family protein. In general, the Bcl-2 family protein acts as a template for the formation of the acylsulfonamide. As noted above in connection with Reaction Scheme (1), the thioacid corresponds to Formula (1):

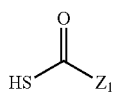

(1)

wherein $Z_1$ is hydrocarbyl, substituted hydrocarbyl, heteroaryl, or heterocyclo.

Typically, such hydrocarbyl substituents for $Z_1$ contain from 1 to 20 carbon atoms and may be linear, branched, or cyclic, and said substituted hydrocarbyl, heteroaryl, and heterocyclo moieties for $Z_1$ may be substituted with one or more of =O, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl).

Although $Z_1$ is hydrocarbyl, substituted hydrocarbyl, heteroaryl, or heterocyclo, in certain embodiments $Z_1$ is aryl, substituted aryl, or heteroaryl. In the embodiments in which $Z_1$ is aryl or substituted aryl, for example, $Z_1$ may have the formula:

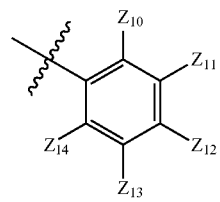

wherein $Z_{10}$, $Z_{11}$, $Z_{12}$, $Z_{13}$, and $Z_{14}$ are independently hydrogen, hydroxyl, protected hydroxyl, halo, hydrocarbyl, substituted hydrocarbyl, heterocyclo, heteroaryl, alkoxy, alkenoxy, alkynoxy, aryloxy, arylalkoxy (heterocyclo)alkoxy, trihaloalkoxy, amino, amido, or cyano, or two of $Z_{10}$, $Z_{11}$, $Z_{12}$, $Z_{13}$, and $Z_{14}$, together with the carbon atoms to which they are attached, form a fused carbocyclic (e.g., napthyl) or heterocyclic ring. In one embodiment, $Z_1$ corresponds to the aryl or substituted aryl structure illustrated above and $Z_{10}$, $Z_{11}$, $Z_{12}$, $Z_{13}$, and $Z_{14}$ are independently hydrogen, amino, alkoxy, nitro, or trihalomethoxy (e.g., trifluoromethoxy); more preferably in this embodiment, $Z_{10}$ and $Z_{14}$ are hydrogen and $Z_{11}$, $Z_{12}$, and $Z_{13}$ are independently hydrogen, amino, alkoxy, nitro, or trihalomethoxy. In one particular embodiment, $Z_1$ is a substituted phenyl or napthyl moiety, with substituents in the ortho-, para-, or meta-positions; more preferably in this embodiment, $Z_1$ is a para-substituted phenyl or napthyl moiety; thus, for example, at least $Z_{11}$ and $Z_{13}$ in the above structure are substituted with alkyl, substituted alkyl, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl). Typically in this embodiment, $Z_{10}$, $Z_{12}$, and $Z_{14}$ are hydrogen.

In the embodiments in which $Z_1$ corresponds to the aryl or substituted aryl structure illustrated above and where one or more of $Z_{10}$, $Z_{11}$, $Z_{12}$, $Z_{13}$, and $Z_{14}$ are hydrocarbyl, for example, they may be independently alkyl, alkenyl, alkynyl, aryl, alkaryl, or aralkyl. Typically, such substituents contain from 1 to 20 carbon atoms and may be linear, branched, or cyclic. By way of example, the $Z_{10}$, $Z_{11}$, $Z_{12}$, $Z_{13}$, and $Z_{14}$ substituents may be selected from methyl, ethyl, n-propyl, cyclopropyl, isopropyl, n-butyl, cyclobutyl, isobutyl, s-butyl, n-pentyl, isopentyl, cyclopentyl, n-hexyl, isohexyl, cyclohexyl, benzyl, phenyl, and napthyl. Where one or more of $Z_{10}$, $Z_{11}$, $Z_{12}$, $Z_{13}$, and $Z_{14}$ are substituted hydrocarbyl, for example, they may be independently substituted alkyl, substituted alkenyl, substituted alkynyl, substituted aryl, substituted alkaryl, or substituted aralkyl. Similar to the hydrocarbyl moieties, these substituents may contain 1 to 20 carbon atoms and may be linear, branched, or cyclic; one or more hydrogen atoms of the substituted hydrocarbyl moieties, however, are replaced with a different substituent such as, for example, =O, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl).

Where $Z_1$ corresponds to the aryl or substituted aryl structure illustrated above and where one or more of $Z_{10}$, $Z_{11}$, $Z_{12}$, $Z_{13}$, and $Z_{14}$ are amino, for example, the amino moiety may have the formula: —N($Z_X$)($Z_Y$) wherein $Z_X$ and $Z_Y$ are independently hydrogen, hydrocarbyl, substituted hydrocarbyl, heteroaryl, heterocyclo, or an amino protecting group, or $Z_X$ and $Z_Y$, together with the nitrogen atom to which they are attached, form a substituted or unsubstituted alicyclic, bicyclic, aryl, heteroaryl, or heterocyclic moiety, typically having 3 to 10 atoms in the ring.

In one particular embodiment, $Z_1$ has the formula:

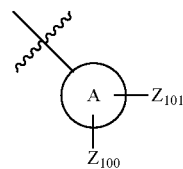

wherein A is phenyl or a five- or six-membered aromatic carbocyclic or heterocyclic ring wherein from one to three carbon atoms may be replaced by a heteroatom selected from N, O, or S, and wherein A is substituted with $Z_{100}$ and $Z_{101}$ through ring carbon atoms or ring heteroatoms, and $Z_{100}$ and $Z_{101}$ are independently hydrogen, hydrocarbyl, substituted hydrocarbyl, heterocyclo, alkoxy, alkenoxy, alkynoxy, aryloxy, heterocyclo(alkoxy), or halo. Where $Z_{100}$ and $Z_{101}$ are hydrocarbyl or substituted hydrocarbyl, for example, they may be substituted or unsubstituted (straight, branched, or cyclic) alkyl, alkenyl, alkynyl, aryl, aralkyl, or arylalkenyl, wherein the substituents for such groups may be, for example, =O, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl). In one particular embodiment, $Z_{100}$ and $Z_{101}$ are selected from hydrogen, alkyl, aryl, arylalkenyl, arylalkoxy, cycloalkenyl, cycloalkyl, halo, heterocyclo, or (heterocyclo)alkoxy. Where $Z_{100}$ and/or $Z_{101}$ are heterocyclo, for example, they may be selected from substituted or unsubstituted morpholino, pyran, tetrahydropyran, piperazinyl, piperidinyl, tetrahydropyridinyl, pyrrolidinyl, 1,4-diazepanyl, and azepinyl.

In another particular embodiment, $Z_1$ has the structure:

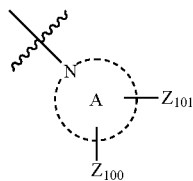

wherein A is a five-, six-, or seven-membered non-aromatic ring containing a nitrogen atom wherein from zero to two carbon atoms are replaced by a heteroatom selected from N, O, or S, and wherein A is substituted with $Z_{100}$ and $Z_{101}$ through ring carbon atoms or ring heteroatoms, and $Z_{100}$ and $Z_{101}$ are independently hydrogen, hydrocarbyl, substituted hydrocarbyl, heterocyclo, alkoxy, alkenoxy, alkynoxy, aryloxy, heterocyclo(alkoxy), or halo. In accordance with these embodiments, for example, $Z_1$ may be a substituted or unsubstituted piperazine, piperidine, tetrahydropyridine, pyrrolidine, pyrroline, 1,4-diazepane, or azepane moiety. Where $Z_{100}$ and $Z_{101}$ are hydrocarbyl or substituted hydrocarbyl, for example, they may be substituted or unsubstituted (straight, branched, or cyclic) alkyl, alkenyl, alkynyl, aryl, aralkyl, or arylalkenyl, wherein the substituents for such groups may be, for example, =O, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl). In one particular embodiment, $Z_{100}$ and $Z_{101}$ are selected from hydrogen, alkyl, aryl, arylalkenyl, arylalkoxy, cycloalkenyl, cycloalkyl, halo, heterocyclo, or (heterocyclo)alkoxy. Where $Z_{100}$ and/or $Z_{101}$ are heterocyclo, for example, they may be selected from substituted or unsubstituted morpholino, pyran, tetrahydropyran, piperazinyl, piperidinyl, tetrahydropyridinyl, pyrrolidinyl, 1,4-diazepanyl, and azepinyl.

As noted above, in certain embodiments, $Z_1$ is heteroaryl. According to these embodiments, for example, $Z_1$ may be substituted or unsubstituted furyl, thienyl, pyridyl, oxazolyl, isoxazolyl, imidazolyl, pyridyl, pyrimidyl, purinyl, triazolyl, or thiazolyl. In one particular embodiment, $Z_1$ is phenyl, substituted phenyl, substituted alkyl, or substituted or unsubstituted furyl, thienyl, pyridyl, pyridinyl, oxazolyl, imidazolyl, pyridyl, pyrimidyl, purinyl, triazolyl, or thiazolyl; more preferably in this embodiment, $Z_1$ is phenyl, substituted phenyl, pyridinyl, substituted pyridinyl, furyl, or substituted furyl. In these embodiments, the substituents for the substituted groups may correspond to those described above in connection with $Z_{100}$ and $Z_{101}$.

In another embodiment, $Z_1$ is heterocyclo. In accordance with this embodiment, for example, $Z_1$ may be substituted or unsubstituted morpholino, pyran, tetrahydropyran, piperazinyl, piperidinyl, tetrahydropyridinyl, pyrrolidinyl, pyrrolinyl, 1,4-diazepanyl, or azepinyl. In these embodiments, the substituents for the substituted groups may correspond to those described above in connection with $Z_{100}$ and $Z_{101}$.

In another embodiment, $Z_1$ is alkyl or substituted alkyl. In accordance with this embodiment, therefore, $Z_1$ may be —(CH$_2$)$_x$—$Z_{102}$ wherein $Z_{102}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3. Where $Z_{102}$ is amino, for example, $Z_{102}$ may have the formula: —N(Z$_X$)(Z$_Y$) wherein Z$_X$ and Z$_Y$ are independently hydrogen, hydrocarbyl, substituted hydrocarbyl, heteroaryl, heterocyclo, or an amino protecting group, or Z$_X$ and Z$_Y$, together with the nitrogen atom to which they are attached, form a substituted or unsubstituted alicyclic, bicyclic, aryl, heteroaryl, or heterocyclic moiety, typically having 3 to 10 atoms in the ring. In one embodiment in which $Z_{102}$ is amino, for example, $Z_{102}$ is a substituted or unsubstituted piperidine, piperazine, or tetrahydroisoquinoline; according to certain embodiments in which $Z_{102}$ is a tetrahydroisoquinoline, the tetrahydroisoquinoline may have the structure:

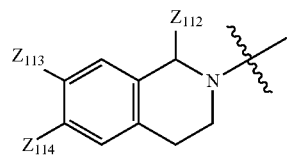

wherein $Z_{112}$, $Z_{113}$, and $Z_{114}$ are independently hydrogen, hydroxyl, hydrocarbyl, substituted hydrocarbyl, alkoxy, alkenoxy, alkynoxy, or aryloxy. In one particular embodiment in which the tetrahydroisoquinoline has the structure shown above, $Z_{112}$, $Z_{113}$, and $Z_{114}$ are independently hydrogen, hydroxyl, alkyl, substituted alkyl, aryl, substituted aryl, alkoxy, or aryloxy.

In combination, among certain of the preferred embodiments are thioacids corresponding to Formula (2) wherein $Z_1$ is heteroaryl, heterocyclo, or has the formula:

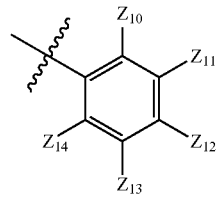

wherein $Z_{10}$, $Z_{11}$, $Z_{12}$, $Z_{13}$, and $Z_{14}$ are independently hydrogen, amino, alkoxy, nitro, or trihalomethoxy (e.g., trifluoromethoxy); or $Z_1$ is —(CH$_2$)$_x$—$Z_{102}$ wherein $Z_{102}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3. Still more preferably in these embodiments, $Z_1$ is phenyl or napthyl optionally substituted with one or more amino, alkoxy, nitro, or trihalomethoxy groups, or $Z_1$ is aminoalkyl, or substituted or unsubstituted thiazolyl, furyl, or isoxazolyl.

In certain embodiments, the thioacids (1) are selected from the group consisting of (TA1), (TA2), (TA3), (TA4), (TA5), (TA6), (TA7), (TA8), (TA9), and (TA10):

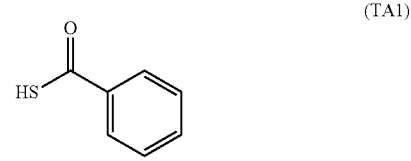

(TA1)

(TA2) 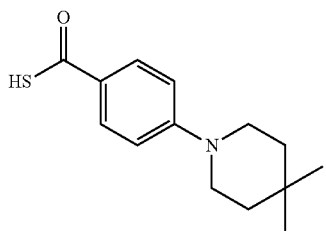

(TA3) 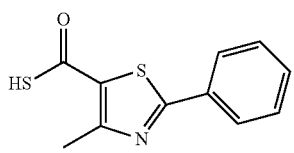

(TA4) 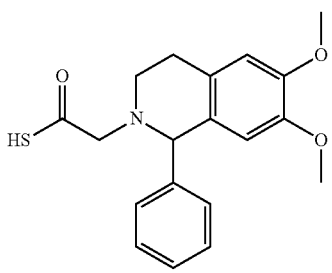

(TA5) 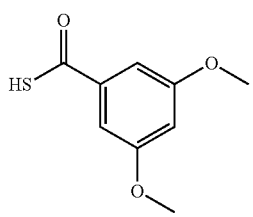

(TA6) 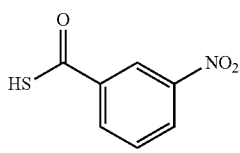

(TA7) 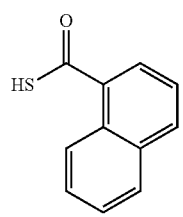

(TA8) 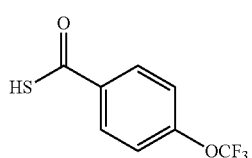

(TA9) 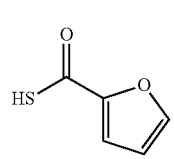

(TA10) 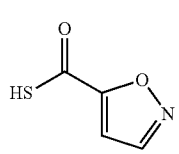

In one particular embodiment, the thioacid (1) corresponds to one or more of formulae: (TA2), (TA3), (TA4), (TA5), (TA9), and (TA10). In another particular embodiment, the thioacid (1) corresponds to one or more of formulae: (TA2), (TA3), (TA4), (TA5), (TA6), and (TA7).

In general, the thioacids described above for use in the processes described herein are commercially available or can be prepared according to conventional organic synthesis techniques.

Sulfonyl Azides

The sulfonyl azides for use in reacting with the thioacids corresponding to Formula (1) in the acylsulfonamide-forming processes described herein generally correspond to Formula (2):

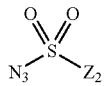

(2)

wherein $Z_2$ is hydrocarbyl, substituted hydrocarbyl, heteroaryl, or heterocyclo. Typically, such hydrocarbyl substituents for $Z_2$ contain from 1 to 20 carbon atoms and may be linear, branched, or cyclic, and said substituted hydrocarbyl, heteroaryl, and heterocyclo moieties for $Z_2$ may be substituted with one or more of =O, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl).

In general, although $Z_2$ is hydrocarbyl, substituted hydrocarbyl, heteroaryl, or heterocyclo, in certain embodiments $Z_2$ is substituted or unsubstituted alkyl, alkenyl, alkynyl, aryl, alkaryl, or aralkyl. In one particular embodiment, $Z_2$ is aryl or substituted aryl; thus, for example, $Z_2$ may have the formula:

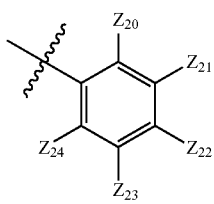

wherein $Z_{20}$, $Z_{21}$, $Z_{22}$, $Z_{23}$, and $Z_{24}$ are independently hydrogen, halo, hydrocarbyl, substituted hydrocarbyl, alkoxy, alkenoxy, alkynoxy, aryloxy, nitro, cyano, amino, or amido, or two of $Z_{20}$, $Z_{21}$, $Z_{22}$, $Z_{23}$, and $Z_{24}$, together with the carbon atoms to which they are attached, form a fused carbocyclic (e.g., napthyl) or heterocyclic ring. In another particular embodiment, $Z_2$ is phenyl, substituted phenyl, napthyl, or substituted napthyl.

In one embodiment in which $Z_2$ corresponds to the aryl or substituted aryl structure illustrated above, $Z_{20}$, $Z_{21}$, $Z_{22}$, $Z_{23}$, and $Z_{24}$ are independently alkyl, substituted alkyl, amino, alkoxy, alkenoxy, alkynoxy, or aryloxy. In a particular embodiment, $Z_{20}$, $Z_{21}$, $Z_{23}$, and $Z_{24}$ are hydrogen and $Z_{23}$ is alkyl, substituted alkyl, amino, alkoxy, alkenoxy, alkynoxy, or aryloxy.

Where one or more of $Z_{20}$, $Z_{21}$, $Z_{22}$, $Z_{23}$, and $Z_{24}$ are substituted alkyl, for example, the alkylene moieties may be substituted, for example, with =O, —OH, —OR$_Z$, —COOH, —COOR$_Z$, —CONH$_2$, —NH$_2$, —NHR$_Z$, —NR$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl). In one particular embodiment, $Z_2$ corresponds to the aryl or substituted aryl structure illustrated above, wherein $Z_{20}$, $Z_{21}$, $Z_{23}$, and $Z_{24}$ are hydrogen and $Z_{22}$ is —N($Z_{220}$)($Z_{221}$) or —CH$_2$—N($Z_{220}$)($Z_{221}$), wherein $Z_{220}$ and $Z_{221}$ are independently hydrogen, alkyl, substituted alkyl, aryl, substituted aryl, or $Z_{220}$ and $Z_{221}$ together with the nitrogen atom to which they are attached, form a substituted or unsubstituted alicyclic, bicyclic, aryl, or heterocyclic moiety. In another particular embodiment, $Z_2$ corresponds to the aryl or substituted aryl structure illustrated above, wherein $Z_{20}$, $Z_{21}$, $Z_{23}$, and $Z_{24}$ are hydrogen and $Z_{22}$ is —N($Z_{220}$)($Z_{221}$) or —CH$_2$—N($Z_{220}$)($Z_{221}$), wherein $Z_{220}$ and $Z_{221}$ are independently hydrogen, alkyl, substituted alkyl, aryl, substituted aryl, or $Z_{220}$ and $Z_{221}$ together with the nitrogen atom to which they are attached, form a substituted or unsubstituted alicyclic, bicyclic, aryl, or heterocyclic moiety; more preferably in this embodiment, $Z_2$ is an N,N-disubstituted (amino)phenyl or (aminomethyl)phenyl. Substituents for the $Z_{220}$ and $Z_{221}$ moieties may be, for example, =O, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl).

In one particular embodiment in which $Z_2$ corresponds to the aryl or substituted aryl structure illustrated above, $Z_{20}$, $Z_{21}$, $Z_{22}$, $Z_{23}$, and $Z_{24}$ are independently alkyl (straight, branched, or cyclic), alkenyl (straight, branched, or cyclic), alkynyl (straight or branched), aryl, alkoxy, arylalkoxy, aryloxy, aryloxyalkoxy, alkylcarbonyloxy, alkylsulfanyl, arylsulfanyl, arylsulfanylalkoxy, cycloalkylalkoxy, cycloalkyloxy, cyano, halo, haloalkyl, haloalkoxy, heterocyclo, (heterocyclo)oxy, nitro, and amino. Where one or more of $Z_{20}$, $Z_{21}$, $Z_{22}$, $Z_{23}$, and $Z_{24}$ are amino, the amino moiety may have the formula: —N($Z_X$)($Z_Y$) wherein $Z_X$ and $Z_Y$ are independently hydrogen, alkyl, alkenyl, alkoxyalkyl, alkoxycarbonylalkyl, alkylsulfanylalkyl, alkylsulfonylalkyl, aryl, arylalkyl, arylalkylsulfanylalkyl, aryloxyalkyl, arylsulfanylalkyl, arylsulfinylalkyl, arylsulfonylalkyl, carboxyalkyl, cycloalkenyl, cycloalkenylalkyl, cycloalkyl, (cycloalkyl)alkyl, cycloalkylcarbonyl, heterocyclo, (heterocyclo)alkyl, (heterocyclo)sulfanylalkyl, hydroxyalkyl, or a nitrogen protecting group, or $Z_X$ and $Z_Y$ together with the nitrogen atom to which they are attached, form a substituted or unsubstituted imidazolyl, morpholinyl, piperazinyl, piperidinyl, pyrrolidinyl, pyrrolyl, thiomorpholinyl, or thiomorpholinyl dioxide moiety.

In another particular embodiment, $Z_2$ is alkyl or substituted alkyl. In accordance with this embodiment, therefore, $Z_2$ may be —(CH$_2$)$_X$—$Z_{200}$ wherein $Z_{200}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3.

Alternatively, $Z_2$ may be heteroaryl. Thus, for example, $Z_2$ may be substituted or unsubstituted furyl, thienyl, pyrrolyl, oxazolyl, imidazolyl, pyridyl, pyrimidyl, purinyl, triazolyl, or thiazolyl.

In another alternative embodiment, $Z_2$ is heterocyclo. In accordance with this embodiment, for example, $Z_2$ may be substituted or unsubstituted morpholino, pyran, tetrahydropyran, piperazinyl, piperidinyl, tetrahydropyridinyl, pyrrolidinyl, pyrrolinyl, 1,4-diazepanyl, or azepinyl. In these embodiments, the substituents for the substituted groups may correspond to those described above in connection with $Z_{20}$, $Z_{21}$, $Z_{22}$, $Z_{23}$, and $Z_{24}$.

In certain embodiments, the sulfonyl azides (2) are selected from the group consisting of (SZ1), (SZ2), (SZ3), (SZ4), (SZ5), (SZ6), (SZ7), (SZ8), (SZ9), (SZ10), (SZ11), (SZ12), (SZ13), (SZ14), (SZ15), (SZ16), and (SZ17):

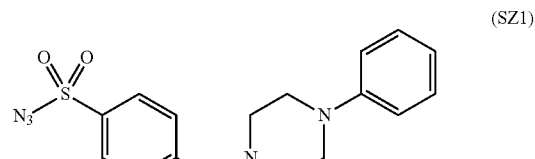

(SZ1)

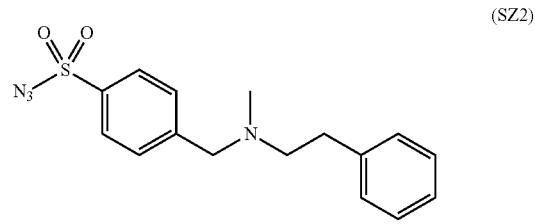

(SZ2)

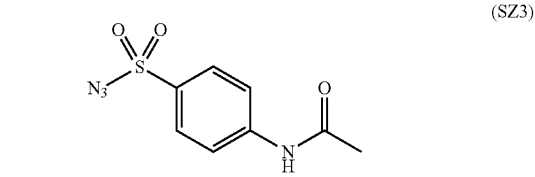

(SZ3)

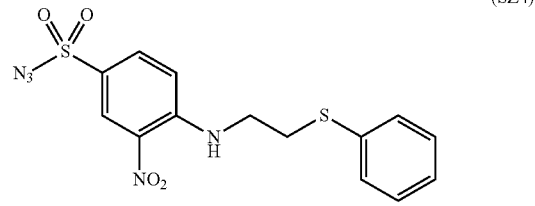

(SZ4)

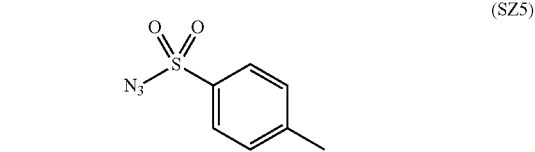

(SZ5)

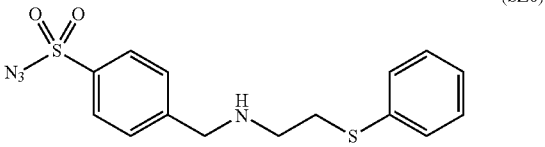

(SZ6)

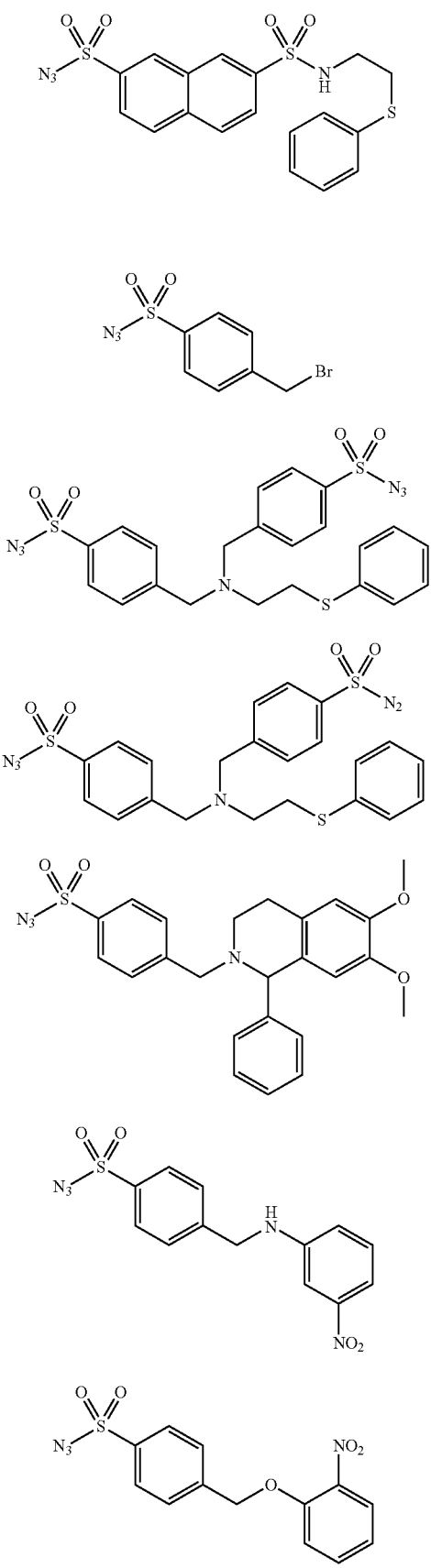

In one particular embodiment, the sulfonyl azide (2) corresponds to one or more of formulae: (SZ9), (SZ10), (SZ11), (SZ15), (SZ16), and (SZ17). In general, the sulfonyl azides described above for use in the processes described herein are commercially available or can be prepared according to conventional organic synthesis techniques.

Bcl-2 Family Proteins

The thioacid (1) and the sulfonyl azide (2), or libraries thereof, are reacted in the presence of a biological target. In general, the biological target is a biological molecule involved in one or more biological pathways associated with various diseases and conditions including cancer, diabetes, neurodegenerative diseases, cardiovascular diseases, respiratory diseases, digestive system diseases, infectious diseases, inflammatory diseases, autoimmune diseases, and the like. Likewise, a range of biological pathways may be involved, including cell cycle regulation (e.g., cellular proliferation and apoptosis), angiogenesis, signaling pathways, tumor suppressor pathways, inflammation, oncogenes, and growth factor receptors, among a variety of others.

As noted above, the Bcl-2 family of proteins includes both anti-apoptotic molecules and pro-apoptotic molecules. The anti-apoptotic Bcl-2 family members (e.g., Bcl-2, Bcl-$X_L$, Mcl-1, A1/BFL-1, Boo/Diva, Bcl-w, and Bcl-y) inhibit the release of certain pro-apoptotic factors from mitochondria, whereas pro-apoptotic Bcl-2 family members (e.g., Bak, Bax, Bad, tBid, Harakiri (HRK), Bim, Bcl-Xs, Bmf, Egl-1, Puma, and Noxa) induce the release of mitochondrial apoptogenic molecules into the cytosol. In accordance the process described herein, the thioacid(s) (1) is/are reacted with the sulfonyl azide(s) (2) in the presence of a protein of the Bcl-2 family; thus, in one embodiment the Bcl-2 family protein is an anti-apoptotic Bcl-2 family protein, and in another embodiment the Bcl-2 family protein is a pro-apoptotic Bcl-2 family protein. In some of these embodiments, the Bcl-2 family proteins contemplated include, but are not limited to, Bcl-2, Bcl-$X_L$, Mcl-1, A1/BFL-1, Boo/Diva, Bcl-w, Bcl-y, Bak, Bax, Bad, tBid, Harakiri, Bim, Bcl-Xs, Bmf, Egl-1, Puma, and Noxa. It is also contemplated that two or more Bcl-2 protein family members may be utilized in the reaction. In one particular embodiment, the Bcl-2 family protein is Bcl-$X_L$. In another particular embodiment, the Bcl-2 family protein is Mcl-1.

Acylsulfonamides

The processes described herein generally utilize the biological target molecule (e.g., Bcl-$X_L$ or Mcl-1) as the reaction vessel or reaction template to assemble an acylsulfonamide compound having preferential binding to the biological target, from one or more thioacids and one or more sulfonyl azides. Thus, the target-guided synthesis strategy utilizes the biological molecule itself as a template for generating potential ligand inhibitors from the initial building block fragments or scaffolds (i.e., the thioacids and the sulfonyl azides in the library), that are selectively bound to the target biomolecule and then irreversibly linked to each other within the confines of the binding pockets of the target protein. As this approach employs the biological target to assemble its own inhibitors from relatively few starting reagents (which can be combined in thousands or tens of thousands of different ways), rather than requiring tedious synthesis, purification, and screening of thousands of library compounds, it is more efficient than conventional combinatorial chemistry techniques. However, as described in further detail below, certain aspects of combinatorial chemistry can be used in the methods described herein.

The thioacids and the sulfonyl azides generally combine to form an acylsulfonamide. These techniques are capable of producing high-affinity inhibitors by assembling the building block reagents irreversibly inside the binding pockets of a target biomolecule. Subsequent screening of target biomolecule-generated "hits" then establish their binding affinity to and specificity for the target. Once the "hit" compounds are determined, they can be synthesized according to conventional organic chemistry methods such as described below, or extracted from the target protein and purified in trace amounts.

For bivalent molecules that have multiple interactions with the Bcl-2 family protein, the resulting hits are very potent (e.g., high affinity); the bivalent molecules bind to the protein binding site and reach into the substrate pocket. For entropy reasons (e.g., avoidance of the loss of three degrees of rotational and translational freedom), among other things, ligand inhibitors display much higher affinity to their biological targets than the individual components. Thus, even initial compound (e.g., thioacids and sulfonyl azides) fragments with only modest micromolar affinity to individual binding pockets can generate nanomolar inhibitors when coupled together to permit optimal binding interactions with the biological target. Thus, the binding affinity of the building block reagent (i.e., scaffold) or precursor to the Bcl-2 family protein does not need to be in the nanomolar range.

Figure 2:
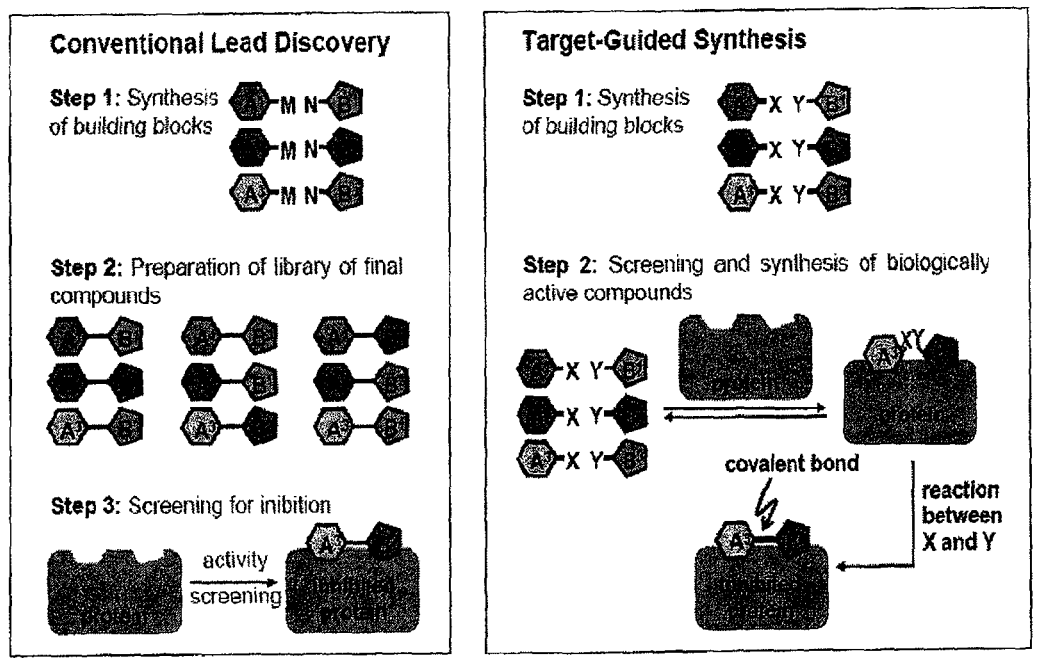
FIG. 2 illustrates exemplary steps of conventional lead discovery and target-guided synthesis protocols.

The general approach of in situ ligation chemistry is illustrated in FIG. 2, and ligation chemistry techniques are described, for example, in the following references: Kolb et al., Angew. Chem. Int. Ed. 2001, 40, 2004-2021; Kolb et al., Drug Discovery Today 2003, 8, 1128-1137; Rostovtsev et al., Angew. Chem. Int. Ed. 2002, 41, 2596-2599; Tornoe et al., Journal of Organic Chemistry 2002, 67, 3057-3064; Wang et al., Journal of the American Chemical Society 2003, 125, 3192-3193; Lee et al., Journal of the American Chemical Society 2003, 125, 9588-9589; Lewis et al., Angew. Chem., Int. Ed. 2002, 41, 1053-1057; Manetsch et al., Journal of the American Chemical Society 2004, 126, 12809-12818; Mocharla et al., Angew. Chem. Int. Ed. 2005, 44, 116-120; Whiting et al., Angew. Chem. 2006, 118, 1463-1467; Whiting et al., Angew. Chem. Int. Ed. Engl. 2006, 45, 1435-1439; and Sharpless et al., Expert Opin. Drug Discovery 2006, 1, 525-538.

In particular, the thioacids and sulfonyl azides corresponding to Formula (1) and (2), respectively, undergo an amidation reaction as illustrated in Reaction Scheme (1) (see also, e.g., Shangguan et al. J. Am. Chem. Soc. 2003, 125, 7754-7755). As noted above, the reaction of the thioacid and the sulfonyl azide is templated by the biological target molecule, a Bcl-2 family protein, in situ within its binding pockets. Typically, several thioacids (1) and sulfonyl azides (2) in the form of one or more libraries will be reacted in the presence of the Bcl-2 family protein; the resulting acylsulfonamide(s) (3) which bind(s) to the Bcl-2 family protein will be the compound(s) of interest (e.g., for further synthesis, testing, and analysis).

Thus, the acylsulfonamides which can be prepared in accordance with the process described herein generally correspond to Formula (3):

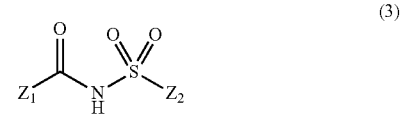

wherein $Z_1$ and $Z_2$ are as defined in connection with Formulae (1) and (2).

For instance, in one embodiment, $Z_1$ is aryl, substituted aryl, or heteroaryl. Thus, in certain embodiments. $Z_1$ has the formula:

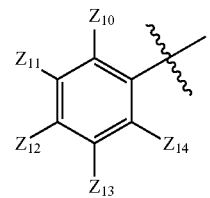

wherein $Z_{10}$, $Z_{11}$, $Z_{12}$, $Z_{13}$, and $Z_{14}$ are independently hydrogen, hydroxyl, protected hydroxyl, halo, hydrocarbyl, substituted hydrocarbyl, heterocyclo, heteroaryl, alkoxy, alkenoxy, alkynoxy, aryloxy, arylalkoxy (heterocyclo)alkoxy, trihaloalkoxy, amino, amido, or cyano, or two of $Z_{10}$, $Z_{11}$, $Z_{12}$, $Z_{13}$, and $Z_{14}$, together with the carbon atoms to which they are attached, form a fused carbocyclic (e.g., napthyl) or heterocyclic ring. In one particular embodiment, $Z_{10}$, $Z_{11}$, $Z_{12}$, $Z_{13}$, and $Z_{14}$ are independently hydrogen, amino, alkoxy, nitro, or trihalomethoxy.

In an alternative embodiment, $Z_1$ has the formula:

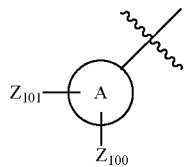

wherein A is phenyl or a five- or six-membered aromatic carbocyclic or heterocyclic ring wherein from one to three carbon atoms may be replaced by a heteroatom selected from N, O, or S, and wherein A is substituted with $Z_{100}$ and $Z_{101}$ through ring carbon atoms or ring heteroatoms, and $Z_{100}$ and $Z_{101}$ are independently hydrogen, hydrocarbyl, substituted hydrocarbyl, heterocyclo, alkoxy, alkenoxy, alkynoxy, aryloxy, heterocyclo(alkoxy), or halo.

In other embodiments, $Z_1$ is substituted or unsubstituted furyl, thienyl, pyridyl, oxazolyl, isoxazolyl, imidazolyl, pyridyl, pyrimidyl, purinyl, triazolyl, or thiazolyl, or $Z_1$ is substituted or unsubstituted morpholino, pyran, tetrahydropyran, piperazinyl, piperidinyl, tetrahydropyridinyl, pyrrolidinyl, pyrrolinyl, 1,4-diazepanyl, or azepinyl. In still other embodiments, $Z_1$ is alkyl or substituted alkyl; here, for example, $Z_1$ may be —$(CH_2)_x$—$Z_{102}$ wherein $Z_{102}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3. Substituents for such groups in these embodiments may be selected from the group consisting of =O, —OH, —$OR_Z$, —COOH, —CO-$OR_Z$, —$CONH_2$, —$NH_2$, —$NHR_Z$, —$NR_ZR_Z$, —$NO_2$, —SH, —$SR_Z$, —$SO_2R_Z$, —$SO_2H$, —$SOR_Z$, heterocyclo, and halo (including F, Cl, Br and I), among others, wherein each occurrence of $R_Z$ may be hydrocarbyl or substituted hydrocarbyl (e.g., substituted or unsubstituted alkyl, substituted or unsubstituted aryl, or substituted or unsubstituted aralkyl).

Alternatively, $Z_1$ may be heteroaryl, heterocyclo, or have the formula:

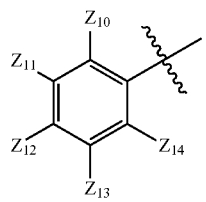

wherein $Z_{10}$, $Z_{11}$, $Z_{12}$, $Z_{13}$, and $Z_{14}$ are independently hydrogen, amino, alkoxy, nitro, or trihalomethoxy (e.g., trifluoromethoxy); or $Z_1$ may be —$(CH_2)_x$—$Z_{102}$ wherein $Z_{102}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3.

Similarly, in these and other embodiments, $Z_2$ may be substituted or unsubstituted alkyl, alkenyl, alkynyl, aryl, alkaryl, or aralkyl. Thus, in certain embodiments, for example, $Z_2$ may have the formula:

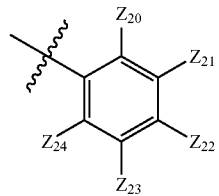

wherein
$Z_{20}$, $Z_{21}$, $Z_{22}$, $Z_{23}$, and $Z_{24}$ are independently hydrogen, halo, hydrocarbyl, substituted hydrocarbyl, alkoxy, alkenoxy, alkynoxy, aryloxy, nitro, cyano, amino, or amido, or two of $Z_{20}$, $Z_{21}$, $Z_{22}$, $Z_{23}$, and $Z_{24}$, together with the carbon atoms to which they are attached, form a fused carbocyclic or heterocyclic ring. For instance, $Z_{20}$, $Z_{21}$, $Z_{22}$, $Z_{23}$, and $Z_{24}$ may independently be alkyl, substituted alkyl, amino, alkoxy, alkenoxy, alkynoxy, or aryloxy. In another embodiment, $Z_2$ is phenyl, substituted phenyl, napthyl, or substituted napthyl.

In other embodiments, $Z_2$ is substituted or unsubstituted furyl, thienyl, pyridyl, oxazolyl, isoxazolyl, imidazolyl, pyridyl, pyrimidyl, purinyl, triazolyl, or thiazolyl, or $Z_2$ is substituted or unsubstituted morpholino, pyran, tetrahydropyran, piperazinyl, piperidinyl, tetrahydropyridinyl, pyrrolidinyl, pyrrolinyl, 1,4-diazepanyl, or azepinyl. In still other embodiments, $Z_2$ is alkyl or substituted alkyl; here, for example, $Z_2$ may be —$(CH_2)_x$—$Z_{200}$ wherein $Z_{200}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3.

In combination, $Z_1$ and $Z_2$ may each be a substituted or unsubstituted aryl or heteroaryl moiety. In one particular embodiment, $Z_1$ is an N,N-disubstituted (aminomethyl)phenyl moiety and $Z_2$ is a para-substituted benzene or napthyl moiety. The substituents for $Z_1$ and/or $Z_2$ in this embodiment may be, for example, =O, —OH, —$OR_Z$, —COOH, —CO-$OR_Z$, —$CONH_2$, —$NH_2$, —$NHR_Z$, —$NR_ZR_Z$, —$NO_2$, —SH, —$SR_Z$, —$SO_2R_Z$, —$SO_2H$, —$SOR_Z$, heterocyclo, and halo (including F, Cl, Br and I), among others, wherein each occurrence of $R_Z$ may be hydrocarbyl or substituted hydrocarbyl (e.g., substituted or unsubstituted alkyl, substituted or unsubstituted aryl, or substituted or unsubstituted aralkyl), among other things.

In one particular embodiment, the acylsulfonamide (3) has the formula:

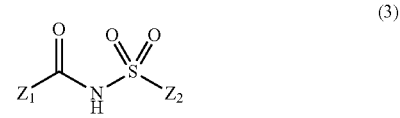

(3)

wherein
$Z_1$ is:

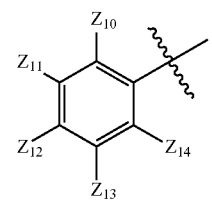

$Z_2$ is:

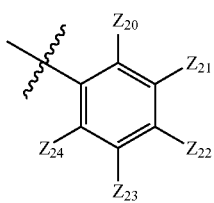

$Z_{11}$ and $Z_{13}$ are alkyl, substituted alkyl, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo, among others, wherein each occurrence of R$_Z$ is substituted or unsubstituted alkyl, substituted or unsubstituted aryl, or substituted or unsubstituted aralkyl;

$Z_{22}$ is —N($Z_{220}$)($Z_{221}$) or —CH$_2$—N($Z_{220}$)($Z_{221}$), wherein $Z_{220}$ and $Z_{221}$ are independently hydrogen, alkyl, substituted alkyl, aryl, substituted aryl, or $Z_{220}$ and $Z_{221}$ together with the nitrogen atom to which they are attached, form a substituted or unsubstituted alicyclic, bicyclic, aryl, or heterocyclic moiety; and $Z_{10}$, $Z_{12}$, $Z_{14}$, $Z_{20}$, $Z_{21}$, $Z_{23}$, and $Z_{24}$ are hydrogen.

In certain embodiments, the acylsulfonamides (3) are selected from the group consisting of (SZ4TA2), (SZ7TA2), (SZ9TA5), (SZ9TA2), (SZ10TA2), (SZ15TA3), (SZ15TA8), (SZ16TA6), (SZ16TA8), (SZ17TA7), (SZ2TA1), (SZ2TA2), (SZ2TA3), (SZ4TA1), (SZ5TA1), (SZ5TA2), (SZ9TA1), (SZ10TA1), (SZ10TA5), (SZ15TA1), (SZ15TA2), (SZ15TA4), (SZ15TA5), (SZ15TA6), (SZ15TA7), (SZ15TA9), (SZ15TA10), (SZ17TA3), (SZ3TA6), (SZ3TA9), and (SZ9TA7):

(SZ7TA2)

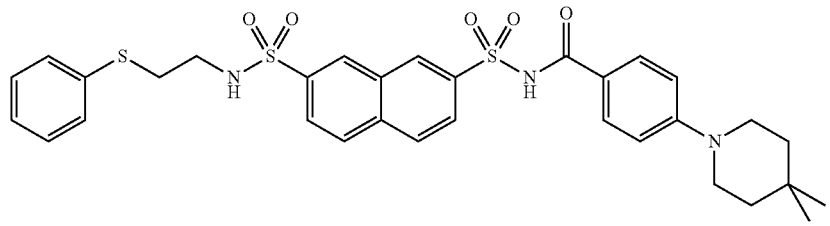

(SZ9TA5)

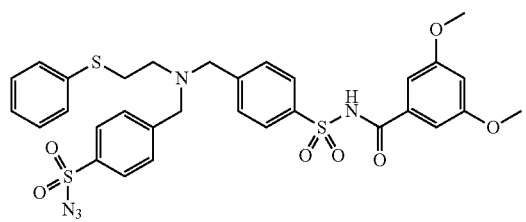

(SZ9TA2)

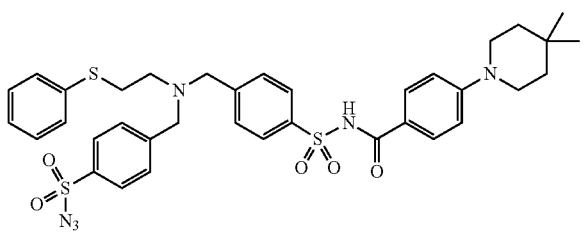

(SZ10TA2)

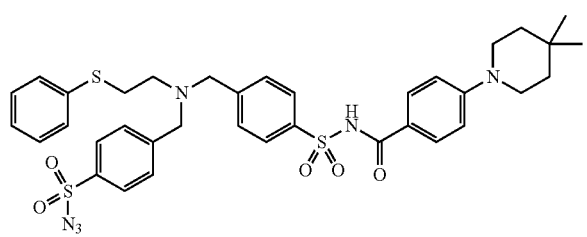

(SZ15TA3)

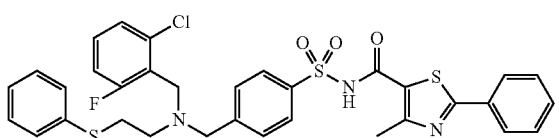

(SZ15TA8)

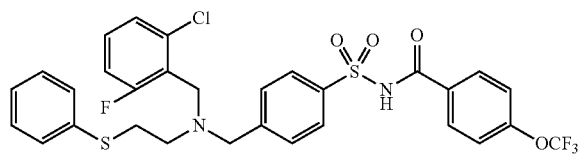

(SZ16TA6)

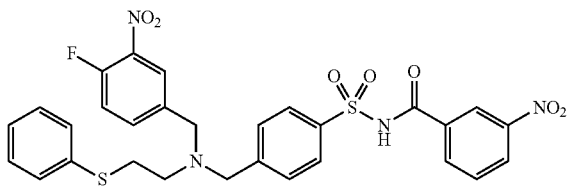

-continued
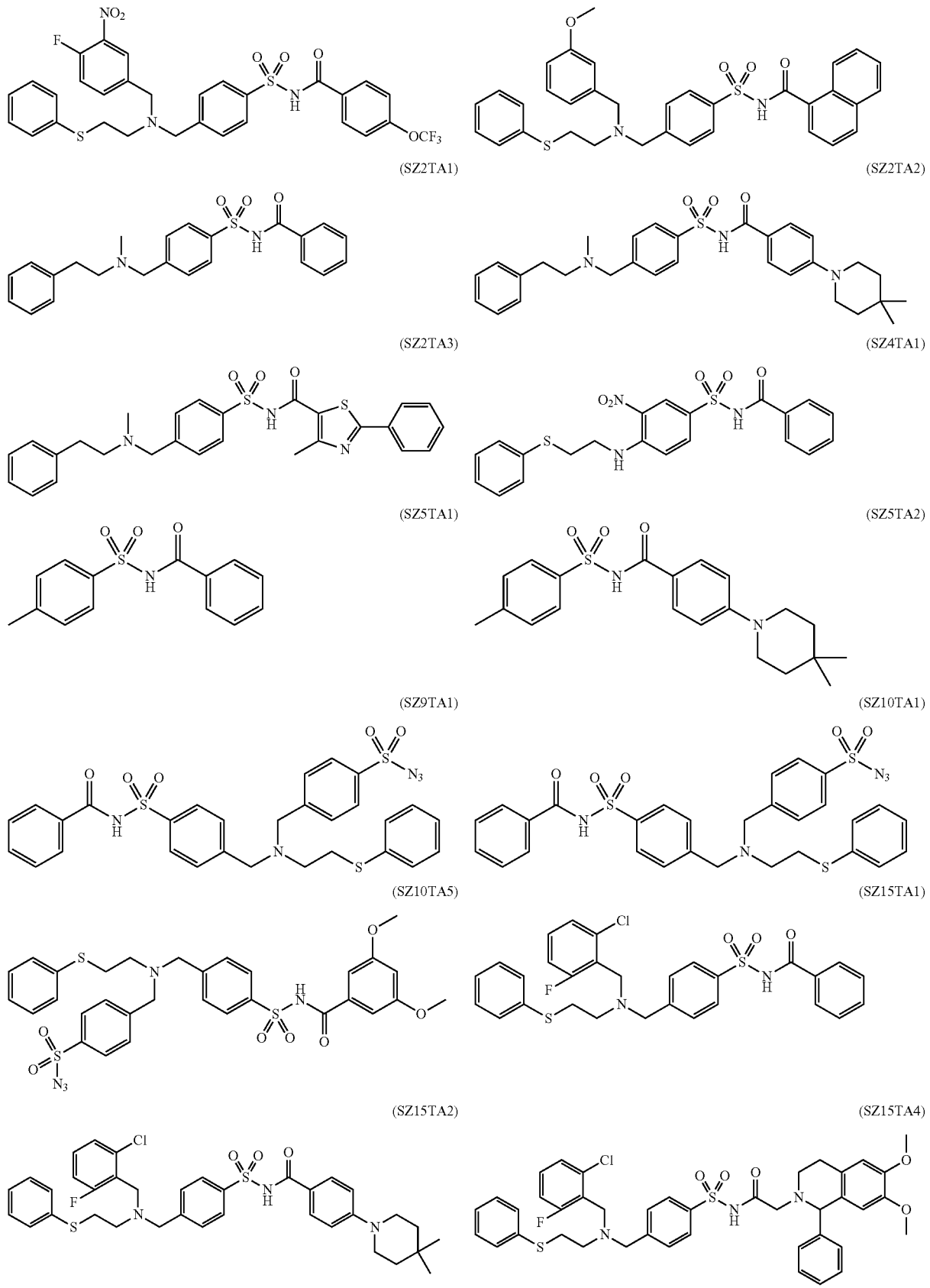

-continued

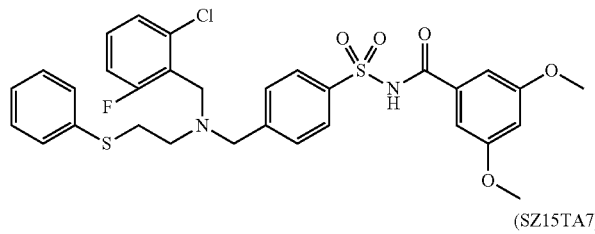
(SZ15TA5)

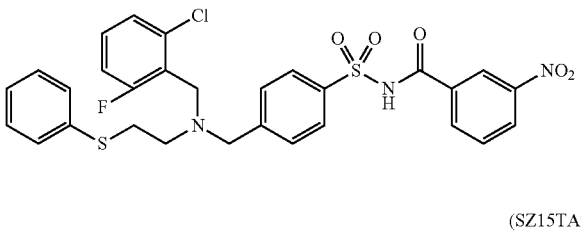
(SZ15TA6)

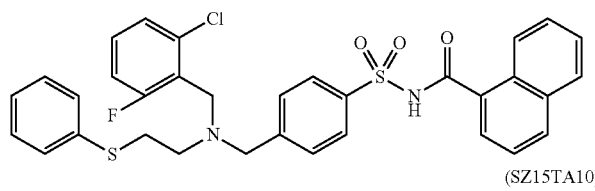
(SZ15TA7)

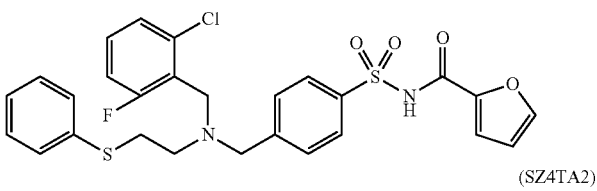
(SZ15TA9)

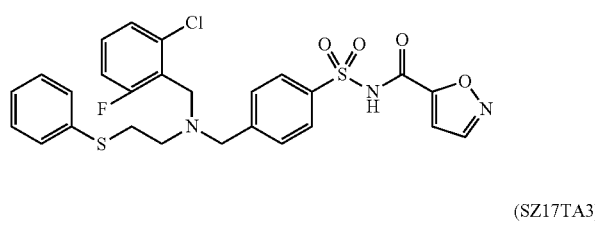
(SZ15TA10)

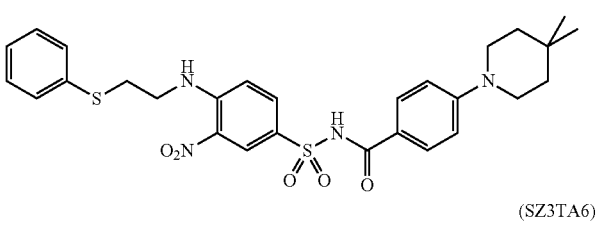
(SZ4TA2)

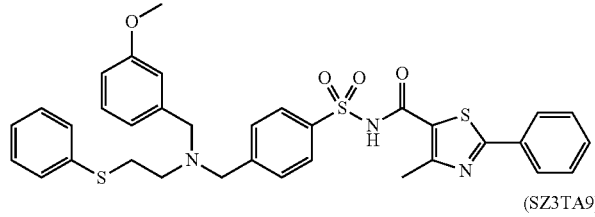
(SZ17TA3)

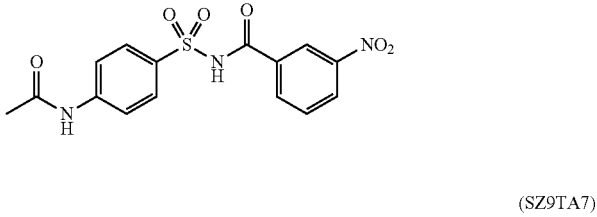
(SZ3TA6)

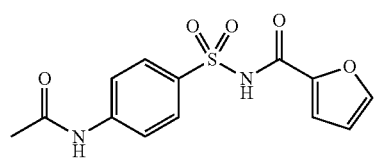
(SZ3TA9)

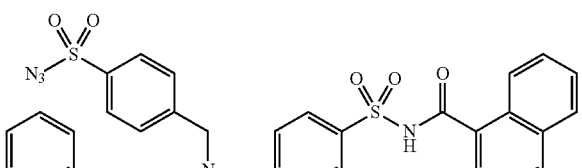
(SZ9TA7)

In one particular embodiment, the acylsulfonamide (3) corresponds to one or more of formulae: (SZ4TA2), (SZ7TA2), (SZ9TA5), (SZ9TA2), (SZ10TA2), (SZ15TA3), (SZ15TA8), (SZ16TA6), (SZ16TA8), and (SZ17TA7). In another particular embodiment, the acylsulfonamide (3) corresponds to one or more of formulae: (SZ2TA1), (SZ2TA2), (SZ2TA3), (SZ4TA1), (SZ5TA1), (SZ5TA2), (SZ9TA1), (SZ10TA1), (SZ10TA5), (SZ15TA1), (SZ15TA2), (SZ15TA4), (SZ15TA5), (SZ15TA6), (SZ15TA7), (SZ15TA9), (SZ15TA10), (SZ17TA3), (SZ3TA6), (SZ3TA9), and (SZ9TA7).

Certain other preferred acylsulfonamides are disclosed in U.S. Pat. No. 6,720,338 to Augeri et al.; U.S. Pat. No. 7,030,115 to Elmore et al.; and U.S. Pat. No. 7,390,799 to Bruncko et al., each of which is hereby incorporated by reference in its entirety.

Generally, the processes described herein are not wholly dependent on the screening of final compounds, prepared through traditional means, but rather allow the Bcl-2 family protein to select and combine building blocks that fit into its binding site to assemble its own inhibitor molecules. For example, with just 2 to 200 building blocks (1 to 100 mono-thioacids and 1 to 100 mono-sulfonyl azides, e.g., in libraries of compounds), one can quickly scan through 1 to 10,000 possible combinations (1×1 to 100×100) without actually having to make and test these compounds via conventional synthesis and analysis. This number becomes even larger, with the same number of building blocks, if one includes di- or tri-thioacids or -sulfonyl azides, thereby providing the target protein with greater flexibility to choose the appropriate building block and functional group at the same time. The screening method is as simple as determining whether or not the product has been formed in a given test mixture by LC/MS, or other suitable instrument. A compound that is formed by the target Bcl-2 family protein likely to be a good and selective binder, due to the multivalent nature of the interaction. In one embodiment, 1 to 10 thioacids corresponding to Formula (1) and 1 to 17 sulfonyl azides corresponding to Formula (2) are incubated or reacted in the presence of the Bcl-2 family protein.

Additional aspects, for example, involve screening methods for identifying a plurality of molecules that exhibit affinity for the binding site of the target Bcl-2 family protein. A functional group capable of participating in a ligation chemistry reaction, such as an thio or azide group, present on the compounds of Formulae (1) and (2), is also attached to the molecule, optionally via a linker. Individual members of the resulting plurality of molecules are then mixed with the target molecule and individual members of a plurality or library of compounds that may exhibit affinity for a substrate binding site of the protein. The members of the substrate-binding library have been chemically modified to include a ligation chemistry functional group compatible with the functional group of the library of protein-binding molecules. Thus, any pair of thioacid and sulfonyl azide compounds, one from each library, that exhibits affinity for the binding sites of the protein will covalently bond via the acylsulfonamide ligation chemistry functional groups in situ. The screening process can utilize conventional screening equipment known in the art such as multi-well microtiter plates.

A mass spectrometer may be used for sequential, automated data analysis of the screening process. Exemplary spectrometer equipment that can be used include the Agilent MSD 1100 SL system, linear ion trap systems (ThermoFinnigan LTQ), quadrupole ion trap (LCQ), or a quadrupole time-of-flight (QTOF from Waters or Applied Biosystems). Each of these analyzers have very effective HPLC interfaces for LC-MS experiments.

In accordance with one embodiment, using the starting precursor fragment, that may be an anchor molecule, discovery can be performed by designing small, targeted compound libraries (e.g., less than 100 compounds) based on known drugs and/or substrates. These libraries may be screened using traditional binding assays. The anchor molecules may be incubated with the Bcl-2 family protein target and small libraries of complementary ligation chemistry reagents or precursors (e.g., thioacids, if the anchor molecule is a sulfonyl azide, and vice versa). Each reaction mixture may be analyzed by LC/MS to identify products that are formed by the Bcl-2 protein. Hit validation is performed through competition experiments to demonstrate that the compound is indeed formed by the protein, and binding assays may establish the binding affinities of the protein-generated hits.

The thioacids and sulfonyl azides may also include various linker moieties between the $Z_1$ substituent and the carbonyl carbon, between the thiol moiety and the carbonyl carbon, between the $Z_2$ substituent and the —S(=O)$_2$— moiety, or between the azide moiety and the —S(=O)$_2$— moiety. The nature and the length of the linker between the two reacting groups or precursors may be selected to afford compounds with optimal binding affinities. Therefore, various types of linkers can be attached to the substrate mimics discussed above. This can readily be accomplished through carbon-heteroatom bond-forming reactions, which can involve the azide groups either directly (acylsulfonamide formation) or indirectly (azide reduction, followed by acylation or sulfonylation of the resulting amines), or other synthesis techniques.

Combinatorial Chemistry Approaches

In a combinatorial approach for identifying or optimizing acylsulfonamides and/or the thioacid and sulfonyl azide building blocks from which they are prepared, a large compositional space (e.g., of thioacids, sulfonyl azides, acylsulfonamides, target proteins, buffer(s), or of relative ratios of two or more of the aforementioned) and/or a large reaction condition space (e.g., of temperature, pressure, reaction time, or other parameter(s)) may be rapidly explored by preparing libraries of thioacids, sulfonyl azides, acylsulfonamides, and/or target proteins and then rapidly screening such libraries. The libraries can comprise, for example, the two or more thioacids, two or more sulfonyl azides, and/or two or more target biomolecules (for use in the preparation of acylsulfonamides), or two or more acylsulfonamides resulting from the reactions described above that are varied with respect to such scaffolds, proteins, and reaction conditions.

Combinatorial approaches for screening a library can include an initial, primary screening, in which initial reaction mixtures or reaction product mixtures are rapidly evaluated to provide valuable preliminary data and, optimally, to identify several "hits," e.g., particular candidate materials having characteristics that meet or exceed certain predetermined metrics (e.g., performance characteristics, desirable properties, unexpected and/or unusual properties, etc., such as binding, inhibition, and so on). Such metrics may be defined, for example, by the characteristics of a known or standard thioacid, sulfonyl azide, target protein, acylsulfonamide, synthetic scheme, or binding parameters. Because local performance maxima may exist in compositional spaces between those evaluated in the primary screening of the first libraries or alternatively, in process-condition spaces different from those considered in the first screening, it may be advantageous to screen more focused libraries (e.g., libraries focused on a smaller range of compositional gradients, or libraries comprising compounds having incrementally smaller structural variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused (thioacid, sulfonyl azide, target protein, or acylsulfonamide) libraries can continue as long as the high-throughput primary screen can meaningfully distinguish between neighboring library compositions or compounds.

Once one or more hits have been satisfactorily identified based on the primary screening, initial scaffold or final product libraries focused around the primary-screen hits can be evaluated with a secondary screen, e.g., a screen designed to provide (and typically verified, based on known materials, to provide) chemical process conditions that relate with a greater degree of confidence to commercially-important processes and conditions than those applied in the primary screen. For example, certain "real-world-modeling" considerations may be incorporated into the secondary screen at the expense of methodology speed (e.g., as measured by sample throughput) compared to a corresponding primary screen. Particular compounds, proteins, reaction conditions, or post-synthesis processing conditions having characteristics that surpass the predetermined metrics for the secondary screen may then be considered to be "leads." If desired, additional thioacid, sulfonyl azide, acylsulfonamide, or other libraries focused about such lead materials can be screened with additional secondary screens or with tertiary screens. Identified lead thioacids, sulfonyl azides, acylsulfonamides, proteins, and/or reaction conditions may be subsequently developed for commercial applications through traditional bench-scale and/or pilot scale experiments.

While the concept of primary screens and secondary screens as outlined above provides a valuable combinatorial research model for investigating thioacid/sulfonyl azide/acylsulfonamide/Bcl-2 family protein reactions, a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen.

In general, the systems, devices and methods, and the building block or final compounds described herein may be applied as either a primary or a secondary screen, depending on the specific research program and goals thereof.

According to certain aspects, methods, systems and devices are disclosed that improve the efficiency and/or effectiveness of the steps necessary to characterize a thioacid or sulfonyl azide sample or a plurality of thioacid or sulfonyl azide samples, or an acylsulfonamide sample or a plurality of acylsulfonamide samples (e.g., libraries of initial and final product mixtures comprising the thioacids and sulfonyl azides, and the acylsulfonamides, respectively). In certain preferred embodiments, a property of a plurality of samples or of components thereof can be detected in a characterization system with an average sample-throughput sufficient for an effective combinatorial or TGS research program. The property may be, for example, protein binding, protein inhibition, or other related or unrelated parameter.

Characterizing a (building block and/or final) sample can include (i) preparing the sample (e.g., synthesis or dilution), (ii) injecting the sample into a mobile phase of a flow characterization system (e.g., liquid chromatography system, flow-injection analysis system, or related apparatus), (iii) separating the sample chromatographically, (iv) detecting a property of the sample or of one or more components thereof, and/or (v) correlating the detected property or parameter to a characterizing property or parameter of interest. Various characterization protocols may be employed involving some or all of the aforementioned steps. For example, a property of a thioacid, sulfonyl azide, or resulting acylsulfonamide sample (or libraries thereof) may be detected in a non-flow, static system either with preparation (steps (i) and (iv)) or without preparation (step (iv)). Alternatively, a property of a sample may be detected in a flow characterization system, either with or without sample preparation and either with or without chromatographic separation. In certain characterization protocols involving flow characterization systems without chromatographic analysis or separation, for example, a property of a sample may be detected in a flow-injection analysis system either with preparation (steps (i), (ii), and (iv)) or without preparation (steps (ii) and (iv)). If chromatographic separation of a sample is desired, a property of the sample may be detected in a liquid chromatography system either with preparation (steps (i), (ii), (iii), and (iv)) or without preparation (steps (ii), (iii), and (iv)). While the physically-detected property (e.g., refracted light, absorbed light, scattered light) from two samples being screened could be compared directly, in most cases the detected property is preferably correlated to a characterizing property of interest (e.g., molecular weight, protein binding, inhibition, etc.) (step (v)).

A plurality of samples may be characterized as described above. As a general approach for improving the sample throughput for a plurality of thioacids, sulfonyl azides, acylsulfonamides, or proteins, each of the steps, applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner, as understood in accordance with conventional combinatorial chemistry protocols.

The throughput of a plurality of samples through a single step in a characterization process is improved by optimizing the speed of that step, while maintaining, to the extent necessary, the information-quality aspects of that step. In many cases, such as with chromatographic or mass spectroscopic analysis, speed can be gained at the expense of resolution of the separated or analyzed components. Although conventional research norms, developed in the context in which research was rate-limited primarily by the synthesis of samples, may find such an approach less than wholly satisfactory, the degree of rigor can be entirely satisfactory for a primary or a secondary screen of a combinatorial library of samples. For combinatorial research (and as well, for many on-line process control systems), the quality of information should be sufficiently rigorous to provide for scientifically acceptable distinctions between the compounds or process conditions being investigated, and for a secondary screen, to provide for scientifically acceptable correlation (e.g., values or, for some cases, trends) with more rigorous, albeit more laborious and time-consuming traditional characterization approaches.

The throughput of a plurality of samples through a series of steps, where such steps are repeated for the plurality of samples, can also be optimized. In accordance with one approach, one or more steps of the cycle can be compressed relative to traditional approaches or can have upstream or downstream aspects truncated to allow other steps of the same cycle to occur sooner compared to the cycle with traditional approaches. In another approach, the earlier steps of a second cycle can be performed concurrently with the later steps of a first cycle. In a rapid-serial approach for characterizing a sample, for instance, sample preparation for a second sample in a series can be effected while the first sample in the series is being synthesized, detected, and/or analyzed. As another example, a second sample in a series can be injected while the first sample in the series is being synthesized, detected, and/or analyzed.

A characterization protocol for a plurality of samples can involve a single-step process. In a rapid-serial detection approach for a single-step process, the plurality of samples and a single detector are serially positioned in relation to each other for serial detection of the samples. In a parallel detection approach, two or more detectors are employed to detect a property of two or more samples simultaneously. In a direct, non-flow detection protocol, for example, two or more samples and two or more detectors can be positioned in relation to each other to detect a property of the two or more samples simultaneously. In a serial-parallel detection approach, a property of a larger number of samples (e.g., three, four, or more) is detected as follows. First, a property of a subset of the three, four, or more samples (e.g., 2 samples) is detected in parallel for the subset of samples, and then serially thereafter, a property of another subset of four or more samples is detected in parallel.

For characterization protocols involving more than one step (e.g., two or more of steps (i), (ii), (iii), (iv), and (v), above), optimization approaches to effect high-throughput characterization of thioacids, sulfonyl azides, target biomolecules, and resulting acylsulfonamides) can vary. For instance, a plurality of samples can be characterized with a single characterization system (A) in a rapid-serial approach in which each of the plurality of samples ($A_1, A_2, A_3 \ldots A_n$) are processed serially through the characterization system (A) with each of the steps ((i), (ii), (iii), (iv), and (v)) effected in series on each of the of samples to produce a serial stream of corresponding characterizing property data ($d_1, d_2, d_3 \ldots d_n$). This approach benefits from relatively minimal capital investment, and may provide sufficient throughput, particularly when the steps (i), (ii), (iii), (iv), and (v) have been optimized with respect to speed and quality of information. As another example, a plurality of samples can be characterized with two or more characterization systems (A, B, C, D . . . N) in a pure parallel (or for larger libraries, serial-parallel) approach in which the plurality of samples ($A_1, A_2, A_3 \ldots A_n$) or a subset thereof are processed through the two or more characterization systems (A, B, C, D . . . ZZ) in parallel, with each individual system effecting each step on one of the samples to produce the characterizing property information ($A_1, A_2, A_3 \ldots A_n$; $B_1, B_2, B_3 \ldots B_n$; $C_1, C_2, C_3 \ldots C_n$, etc.) in parallel. This approach is advantageous with respect to overall throughput, but may be constrained by the required capital investment.

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series. Such a parallel-series hybrid approach can be exemplified, by parallel sample preparation (step (i)) of a plurality of thioacid, sulfonyl azide, or acylsulfonamide samples ($A_1, A_2, A_3 \ldots A_n$), followed by serial injection, chromatographic analysis, detection and correlation (steps (ii), (iii), (iv), and (v)) with a single characterization system (A) to produce a serial stream of corresponding characterizing property information ($d_1, d_2, d_3 \ldots d_n$). In another exemplary parallel-series hybrid approach, a plurality of thioacid, sulfonyl azide, or acylsulfonamide samples ($A_1, A_2, A_3 \ldots A_n$) are prepared, reacted, and injected in series into the mobile phase of four or more characterizing systems (e.g., LC/MS) (A, B, C . . . ZZ), and then detected and correlated in a slightly offset (staggered) parallel manner to produce the characterizing property information ($d_1, d_2, d_3 \ldots d_n$) in the same staggered-parallel manner. If each of the systems has the same processing rates, then the extent of the parallel offset (or staggering) will be primarily determined by the speed of the serial preparation and reaction. In a variation of the preceding example, where the detection and correlation steps are sufficiently rapid, a plurality of thioacid, sulfonyl azide, or acylsulfonamide samples ($A_1, A_2, A_3 \ldots A_n$) could be characterized by serial sample preparation and reaction, staggered-parallel analysis, and then serial correlation, to produce the characterizing property information ($d_1, d_2, d_3 \ldots d_n$) in series. In this case, the rate of injection into the various separation columns is preferably synchronized with the rate of detection. In general, optimization of individual characterization steps (e.g., steps (i), (ii), (iii), (iv), and (v)) with respect to speed and quality of information can improve sample throughput regardless of whether the overall characterization scheme involves a rapid-serial or parallel aspect (i.e., true parallel, serial-parallel or hybrid parallel-series approaches).

A plurality or library of samples generally comprises 2 or more thioacid, sulfonyl azide, target protein, or acylsulfonamide samples. The individual compounds may be physically or temporally separated from each other, e.g., by residing in different sample containers, by having a membrane or other partitioning material positioned between samples, by being partitioned (e.g., in-line) with an intervening fluid, by being temporally separated in a flow process line (e.g., as sampled for process control purposes), or otherwise, or two, three, or more compound samples may be combined or otherwise reside in the same sample container. In certain embodiments, the plurality (or library) of samples typically comprises 4 or more samples (e.g., 4 or more different thioacid, sulfonyl azide, or acylsulfonamide compounds), while in certain other embodiments, 8 or more samples (e.g., 4 or more different thioacid, sulfonyl azide, or acylsulfonamide compounds). Four samples can be employed, for example, in connection with experiments having one control sample and three samples varying (e.g., with respect to compound, target, or process conditions as discussed above) to be representative of a high, a medium and a low-value of the varied factor, and thereby, to provide some indication as to trends. Four samples may also be a minimum number of samples to effect a serial-parallel characterization approach, as described above (e.g., with two detector/analyzers operating in parallel). Eight samples can provide for additional variations in the explored factor space. Higher numbers of samples and libraries thereof can be investigated, according to the methods described herein, to provide additional insights into larger compositional and/or process space. In some cases, for example, the plurality of samples can be 15 or more samples, 20 or more samples, 40 or more samples, 80 or more samples, or more. Such numbers can be loosely associated with standard configurations of other parallel reactor configurations and/or of standard sample containers (e.g., 96-well microtiter plate-type formats). Moreover, even larger numbers of samples can be characterized according to the methods described herein for larger scale research endeavors. Hence, the number of thioacid, sulfonyl azide, and acylsulfonamide samples prepared and analyzed can be 150 or more, 400 or more, 500 or more, 750 or more, 1,000 or more, 1,500 or more, 2,000 or more, 5,000 or more and 10,000 or more. As such, the number of samples can range from about 2 samples to about 10,000 samples, or more, and preferably from about 8 samples to about 10,000 samples, or more. In some cases, in which processing of samples using typical 96-well microtiter-plate formatting is convenient or otherwise desirable, the number of samples can be 96*N, where N is an integer ranging from about 1 to about 100. For many applications, N can suitably range from 1 to about 20, and in some cases, from 1 to about 7.

The plurality of samples can likewise be a library of samples, e.g., a library of thioacids, a library of sulfonyl azides, and/or a library of acylsulfonamides. A library of samples generally comprises an array of two or more different thioacid, sulfonyl azide, and/or acylsulfonamide samples spatially separated, e.g., on a common substrate, or temporally separated, e.g., in a flow system. Candidate samples (i.e., members) within a library may differ in a definable and typically predefined way, including with regard to chemical structure (i.e., the substituents on the thioacid or sulfonyl azide), processing (e.g., synthesis) history (including the biological target utilized in the target-guided synthesis), mixtures of interacting components, purity, etc. The samples may be spatially separated, for instance, at an exposed surface of the substrate, such that the array of samples are separately addressable for characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. Typically, however, for combinatorial research applications, at least two or more, preferably at least four or more, even more preferably eight or more and, in many cases most, and allowably each of the plurality of samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In general, the substrate can be a structure having a rigid or semi-rigid surface on which or into which the array of samples can be formed or deposited. The substrate can be of any suitable material, and preferably consists essentially of materials that are inert with respect to the samples of interest (including, for example, the thioacid, sulfonyl azide, acylsulfonamide, or the biological target molecule (e.g., the Bcl-2 family protein(s)). Certain materials will, therefore, be less desirably employed as a substrate material for certain reaction process conditions (e.g., high temperatures or high pressures) and/or for certain reaction mechanisms. Stainless steel, silicon, including polycrystalline silicon, single-crystal silicon, sputtered silicon, and silica ($SiO_2$) in any of its forms (quartz, glass, etc.), for example, may be substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Organic and inorganic polymers may also be suitably employed in some applications. Exemplary polymeric materials that can be suitable as a substrate material in particular applications include polystyrenes, polyimides such as Kapton™, polypropylene, polytetrafluoroethylene (PTFE) and/or polyether etherketone (PEEK), among others. The substrate material is also preferably selected for suitability in connection with known fabrication techniques. As to form, the sample containers formed in, at or on a substrate can be preferably, but are not necessarily, arranged in a substantially flat, substantially planar surface of the substrate. The sample containers can be formed in a surface of the substrate as dimples, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting. The size and shape can be chosen, however, to be compatible with commercial availability, existing fabrication techniques, and/or with known or later-developed automation techniques, including automated sampling and automated substrate-handling devices, as well as detection and analysis equipment. The substrate is also preferably sized to be portable by humans. The substrate can be thermally insulated if needed, for example, for high-temperature and/or low-temperature applications. In preferred embodiments, the substrate is designed such that the individually addressable regions of the substrate can act as reaction vessels for preparing the acylsulfonamides from the reaction of the thioacids and the sulfonyl azides in the presence of the biological target (e.g., a Bcl-2 protein) in a product mixture (as well as sample containers for the samples during subsequent characterization thereof). Glass-lined, 96-well, 384-well and 1536-well microtiter-type plates, fabricated from stainless steel, aluminum, composite, polystyrene or other polymers or plastics, may be used as substrates for a library of samples. The choice of an appropriate specific substrate material and/or form for certain applications will be apparent to those of skill in the art in view of the guidance provided herein.

The library of materials can be a combinatorial library of building blocks (e.g., thioacids, sulfonyl azides) or a combinatorial library of product mixtures (e.g., acylsulfonamides). Thioacid libraries can comprise, for example, a variety of thioacids corresponding to Formula (1) to be used in the target-guided synthesis approaches described herein. Similarly, sulfonyl azide libraries can comprise, for example, a variety of sulfonyl azides corresponding to Formula (2) to be used in the target-guided synthesis approaches described herein. Acylsulfonamide libraries can comprise, for example, product mixtures resulting from such reactions of thioacids and sulfonyl azides (including libraries thereof) that are varied with respect to, for example, particular substituent patterns, buffers, biological targets, the relative amounts of components, reaction conditions (e.g., pH, temperature, pressure, reaction time) or any other factor that may affect the reaction. Design variables for reactions are well known in the art. A library of thioacid/sulfonyl azide/acylsulfonamide samples may be prepared in arrays, in parallel reactors or in a serial fashion. In certain embodiments, the libraries can be characterized directly, without being isolated, from the reaction vessel in which the compound(s) was synthesized.

While such methods may be generally preferred for a combinatorial approach to lead compound research, they are to be considered exemplary and non-limiting. As noted above, the particular samples characterized according to the methods and with the apparatus disclosed herein can be from any source, including, but not limited to product mixtures resulting from combinatorial synthesis approaches or from target-guided synthesis approaches.

Pharmaceutical Compositions and Methods for Treatment

Other aspects involve methods for treatment of various conditions and diseases using the compounds described herein. According to methods of treatment, the compounds described herein, and particularly the acylsulfonamides corresponding to Formula (3) can be useful for the prevention of metastases from the tumors described above either when used alone or in combination with radiotherapy and/or other chemotherapeutic treatments conventionally administered to patients for treating cancer. When using the compounds for chemotherapy, for example, the specific therapeutically effective dose level for any particular patient will depend upon factors such as the disorder being treated and the severity of the disorder; the activity of the particular compound used; the specific compound employed; the age, body weight, general health, sex, and diet of the patient; the time of administration; the route of administration; the rate of excretion of the compound employed; the duration of treatment; and drugs used in combination with or coincidentally with the compound used. For example, when used in the treatment of solid tumors, the compounds can be administered with chemotherapeutic agents such as alpha interferon, COMP (cyclophosphamide, vincristine, methotrexate, and prednisone), etoposide, mBACOD (methotrexate, bleomycin, doxorubicin, cyclophosphamide, vincristine, and dexamethasone), PRO-MACE/MOPP (prednisone, methotrexate (w/leucovin rescue), doxorubicin, cyclophosphamide, paclitaxel, docetaxel, etoposide/mechlorethamine, vincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like. For example, a tumor may be treated conventionally with surgery, radiation or chemotherapy and a compound disclosed herein subsequently administered to extend the dormancy of micrometastases and to stabilize and inhibit the growth of any residual primary tumor.

Additional aspects include compounds which have been described in detail hereinabove or to pharmaceutical compositions which comprise an effective amount of one or more compounds according to the disclosure, optionally in combination with a pharmaceutically acceptable carrier, additive or excipient (described in further detail below).

Dosage and Amount and Time Course of Treatment

The dose or amount of pharmaceutical compositions including the acylsulfonamide compositions described above administered to the mammal should be an effective amount for the intended purpose, i.e., treatment (or prophylaxis) of one or more of the diseases, pathological disorders, and medical conditions noted above. Generally speaking, the effective amount of the composition administered to the mammal can vary according to a variety of factors such as, for example, the age, weight, sex, diet, route of administration, and the medical condition of the mammal. Specifically preferred doses are discussed more fully below. It will be understood, however, that the total daily usage of the compositions described herein will be decided by the attending physician or veterinarian within the scope of sound medical judgment.

The specific therapeutically effective dose level for any particular mammal will depend upon a variety of factors including the disorder being treated and the severity of the disorder; activity of the specific compound(s) employed; the age, body weight, general health, sex and diet of the patient; the time of administration; the route of administration; the rate of excretion of the specific compound(s) employed; the duration of the treatment; drugs used in combination or coincidental with the specific compound(s) employed and like factors well known in the medical and/or veterinary arts. For example, it is well within the skill of the art to start doses of the compound(s) at levels lower than those required to achieve the desired therapeutic effect and to gradually increase the dosage until the desired effect is achieved. If desired, the effective daily doses may be divided into multiple doses for purposes of administration. Consequently, single dose compositions may contain such amounts or submultiples to make up the daily dose.

Administration of the pharmaceutical composition can occur as a single event or over a time course of treatment. For example, one or more of the compositions can be administered hourly (e.g., every hour, every two hours, every three hours, every four hours, every five hours, every six hours, and so on), daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the mammal in need of such treatment. Alternatively, the compositions can be administered hourly, daily, weekly, bi-weekly, or monthly, for a period of several weeks, months, years, or over the lifetime of the mammal as a prophylactic measure.

One or more of the compounds may be utilized in a pharmaceutically acceptable carrier, additive or excipient at a suitable dose ranging from about 0.05 to about 200 mg/kg of body weight per day, preferably within the range of about 0.1 to 100 mg/kg/day, most preferably in the range of 0.25 to 50 mg/kg/day. As noted above, the desired dose may conveniently be presented in a single dose or as divided doses administered at appropriate intervals, for example as two, three, four or more sub-doses per day.

Ideally, the active ingredient should be administered to achieve effective peak plasma concentrations of the active compound within the range of from about 0.05 uM to about 5 uM. This may be achieved, for example, by the intravenous injection of about a 0.05 to 10% solution of the active ingredient, optionally in saline, or orally administered as a bolus containing about 1 mg to about 5 g, preferably about 5 mg to about 500 mg of the active ingredient, depending upon the active compound and its intended target. Desirable blood levels may be maintained by a continuous infusion to preferably provide about 0.01 mg/kg/hour to about 2.0 mg/kg/hour or by intermittent infusions containing about 0.05 mg/kg to about 15 mg/kg of the active ingredient. Oral dosages, where applicable, will depend on the bioavailability of the compositions from the GI tract, as well as the pharmacokinetics of the compositions to be administered. While it is possible that, for use in therapy, one or more compositions of the invention may be administered as the raw chemical, it is preferable to present the active ingredient as a pharmaceutical formulation, presented in combination with a pharmaceutically acceptable carrier, excipient, or additive.

Routes of Administration, Formulations/Pharmaceutical Compositions

As noted above, the above-described compounds may be dispersed in a pharmaceutically acceptable carrier prior to administration to the mammal. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions can be formulated for any route of administration so long as the blood circulation system is available via that route. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in combination with the acylsulfonamide compounds are well known to those of ordinary skill in the art and are selected based upon a number of factors: the particular compound used, and its concentration, stability and intended bioavailability; the subject, its age, size and general condition; and the route of administration. Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristrate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$ to $C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, N.Y., 1980), Remington's Pharmaceutical Sciences (A. Gennaro, ed., 19th ed.) (Mack Publishing, Easton, Pa., 1995), The United States Pharmacopeia 24, The National Formulary 19, (National Publishing, Philadelphia, Pa., 2000), and A. J. Spiegel et al., Use of Nonaqueous Solvents in Parenteral Products, Journal of Pharmaceutical Sciences, Vol. 52, No. 10, pp. 917-927 (1963).

Formulations containing the above acylsulfonamide compounds may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages.

Salts and Prodrugs

As noted above, the pharmaceutical compositions may include acylsulfonamide compounds in their salt form. Typically, the salt will be a pharmaceutically acceptable salt; that is, a salt prepared from pharmaceutically acceptable non-toxic acids, including inorganic acids and organic acids. Suitable non-toxic acids include inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N"-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like. Pharmaceutically acceptable salts of the compounds described herein can be prepared by reacting the free acid or base forms of these compositions with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, each of which is hereby incorporated by reference herein.

Since prodrugs are known to enhance numerous desirable pharmaceuticals (e.g., solubility, bioavailability, manufacturing), the compound(s) may be delivered in prodrug form. Thus, the present disclosure is intended to cover prodrugs of the compounds (e.g., acylsulfonamides) described above, methods of delivering the same and compositions containing them. Prodrugs generally include any covalently bonded carriers which release an active parent drug in vivo when such prodrug is administered to a mammalian subject. Prodrugs are generally prepared by modifying functional groups present in the compound in such a way that the modifications are cleaved, either in routine manipulation or in vivo, to the parent compound. Prodrugs include compounds wherein a hydroxyl or amino group is bonded to any group that, when the prodrug is administered to a mammalian subject, cleaves to form a free hydroxyl or free amino group, respectively.

Examples of prodrugs include, but are not limited to, acetate, formate, and benzoate derivatives of alcohol and amine functional groups in the compounds and conjugates disclosed herein. Prodrugs of the compound are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compositions of the invention. Prodrugs may refer to compounds that are rapidly transformed in vivo to yield the compound(s) above, for example by hydrolysis in blood. A thorough discussion of prodrugs is provided in the following: Design of Prodrugs, H. Bundgaard, ea., Elsevier, 1985; Methods in Enzymology, K. Widder et al, Ed., Academic Press, 42, p. 309-396, 25 1985; A Textbook of Drug Design and Development, Krogsgaard-Larsen and H. Bundgaard, ea., Chapter 5; "Design and Applications of Prodrugs" p. 113-191, 1991; Advanced Drug Delivery Reviews, H. Bundgard, 8, p. 1-38, 1992; Journal of Pharmaceutical Sciences, 77, p. 285, 30 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ea., American Pharmaceutical Association and Pergamon Press, 1987, each of which is hereby incorporated by reference herein.

Additional Pharmaceutical Components

The above-described pharmaceutical compositions including the acylsulfonamides may additionally include one or more pharmaceutically active components. Suitable pharmaceutically active agents that may be included in the compositions include, for instance, anesthetics, antihypertensives, antianxiety agents, anticlotting agents, anticonvulsants, blood glucose-lowering agents, decongestants, antihistamines, antitussives, antineoplastics, beta blockers, anti-inflammatory agents, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's Disease agents, antibiotics, anti-depressants, and antiviral agents, among others.

The individual components of such combinations may be administered either sequentially or simultaneously in separate or combined pharmaceutical formulations.

ABBREVIATIONS AND DEFINITIONS

The following definitions and methods are provided to better define the present disclosure and to guide those of ordinary skill in the art in the practice of the present disclosure. Unless otherwise noted, terms are to be understood according to conventional usage by those of ordinary skill in the relevant art.

With regard to stereoisomers, it should be understood that a solid line designation for the bonds in the compositions corresponding to Formulae (1), (2), and (3) (and others herein) for attachment of an substituent group (e.g., $Z_1$, $Z_2$, and further substituents on these groups) to a chiral carbon atom of the compound indicates that these groups may lie either below or above the plane of the page (i.e., ◂▬R or ⋯⋯R). All isomeric forms of the compounds disclosed herein are contemplated, including racemates, racemic mixtures, and individual enantiomers or diastereomers.

The terms "acetal" and "ketal," as used herein alone or as part of another group, denote the moieties represented by the following formulae, respectively:

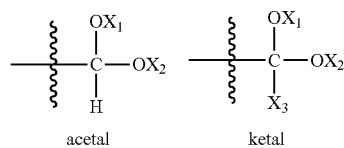

acetal          ketal wherein $X_1$ and $X_2$ are independently hydrocarbyl, substituted hydrocarbyl, heterocyclo, or heteroaryl, and $X_3$ is hydrocarbyl or substituted hydrocarbyl, as defined in connection with such terms, and the wavy lines represent the attachment point of the acetal or ketal moiety to another moiety or compound.

The term "acyl," as used herein alone or as part of another group, denotes the moiety formed by removal of the hydroxyl group from the group —COOH of an organic carboxylic acid, e.g., $X_4C(O)$—, wherein $X_4$ is $X^1$, $X^1O$—, $X^1X^2N$—, or $X^1S$—, $X^1$ is hydrocarbyl, heterosubstituted hydrocarbyl, or heterocyclo, and $X^2$ is hydrogen, hydrocarbyl or substituted hydrocarbyl. Exemplary acyl moieties include acetyl, propionyl, benzoyl, pyridinylcarbonyl, and the like.

The term "acyloxy," as used herein alone or as part of another group, denotes an acyl group as described above bonded through an oxygen linkage (—O—), e.g., $X_4C(O)$ O— wherein $X_4$ is as defined in connection with the term "acyl."

The term "alkanol," as used herein alone or as part of another group, denotes an alkyl radical having 1 to 10 carbon atoms, which is substituted by one, two or three, or more, hydroxyl group(s). Examples of alkanols include methanol, ethanol, n-propan-2-ol, n-propan-3-ol, isopropanol, i-butanol, and the like.

The term "alkanoyl," as used herein, represents an alkyl group attached to the parent molecular moiety through a carbonyl group. The alkanoyl groups of this invention can be optionally substituted with one or two groups independently selected from the group consisting of hydroxyl and amino.

The term "alkanoylalkyl," as used herein, represents an alkanoyl group attached to the parent molecular moiety through an alkyl group.

The term "alkoxy," as used herein alone or as part of another group, denotes an —$OX_5$ radical, wherein $X_5$ is as defined in connection with the term "alkyl." Exemplary alkoxy moieties include methoxy, ethoxy, propoxy, or 2-propoxy, n-, iso-, or tert-butoxy, and the like.

The term "alkenoxy," as used herein alone or as part of another group, denotes an —$OX_6$ radical, wherein $X_6$ is as defined in connection with the term "alkenyl." Exemplary alkenoxy moieties include ethenoxy, propenoxy, butenoxy, hexenoxy, and the like.

The term "alkynoxy," as used herein alone or as part of another group, denotes an —$OX_7$ radical, wherein $X_7$ is as defined in connection with the term "alkynyl." Exemplary alkynoxy moieties include ethynoxy, propynoxy, butynoxy, hexynoxy, and the like.

The term "alkoxyalkanoyl," as used herein, represents an alkoxy group attached to the parent molecular moiety through an alkanoyl group.

The term "alkoxyalkoxy," as used herein, represents an alkoxy group attached to the parent molecular moiety through another alkoxy group.

The term "alkoxyalkoxyalkyl," as used herein, represents an alkoxyalkoxy group attached to the parent molecular moiety through an alkyl group.

The term "alkoxyalkoxycarbonyl," as used herein, represents an alkoxyalkoxy group attached to the parent molecular moiety through a carbonyl group.

The term "alkoxyalkyl," as used herein, represents an alkoxy group attached to the parent molecular moiety through an alkyl group.

The term "alkoxycarbonyl," as used herein, represents an alkoxy group attached to the parent molecular moiety through a carbonyl group.

The term "alkoxycarbonylalkyl," as used herein, represents an alkoxycarbonyl group attached to the parent molecular moiety through an alkyl group.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkylamino," as used herein, represents —N($X_8$)$_2$, wherein $X_8$ is alkyl.

The term "alkylaminoalkyl," as used herein, represents an alkylamino group attached to the parent molecular moiety through an alkyl group.

The term "alkylaminocarbonyl," as used herein, represents an alkylamino group attached to the parent molecular moiety through a carbonyl group.

The term "alkylaminocarbonylalkyl," as used herein, represents an alkylaminocarbonyl group attached to the parent molecular moiety through an alkyl group.

The term "alkylidene," as used herein, represents an alkyl group attached to the parent molecular moiety through a carbon-carbon double bond.

The term "alkylsulfanyl," as used herein, represents an alkyl group attached to the parent molecular moiety through a sulfur atom.

The term "alkylsulfanylalkyl," as used herein, represents an alkylsulfanyl group attached to the parent molecular moiety through an alkyl group.

The term "alkylsulfonyl," as used herein, represents an alkyl group attached to the parent molecular moiety through a sulfonyl group.

The term "alkylsulfonylalkyl," as used herein, represents an alkylsulfonyl group attached to the parent molecular moiety through an alkyl group.

The term "alkylene," as used herein alone or as part of another group, denotes a linear saturated divalent hydrocarbon radical of one to eight carbon atoms or a branched saturated divalent hydrocarbon radical of three to six carbon atoms unless otherwise stated. Exemplary alkylene moieties include methylene, ethylene, propylene, 1-methylpropylene, 2-methylpropylene, butylene, pentylene, and the like. Unless otherwise indicated, one or more hydrogen atoms of the alkylene moieties can be replaced and substituted with one or more of =O, —OH, —OR$_Z$, —COOH, —COOR$_Z$, —CONH$_2$, —NH$_2$, —NHR$_Z$, —NR$_Z$R$_Z$, —NO$_2$, —SH, —SR$_Z$, —SO$_2$R$_Z$, —SO$_2$H, —SOR$_Z$, heterocyclo, and halo (including F, Cl, Br and I), among others, wherein each occurrence of R$_Z$ may be hydrocarbyl or substituted hydrocarbyl (e.g., substituted or unsubstituted alkyl, substituted or unsubstituted aryl, or substituted or unsubstituted aralkyl.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

Unless otherwise indicated, the terms "amine" or "amino," as used herein alone or as part of another group, represents a group of formula —N($X_9$)($X_{10}$), wherein $X_9$ and $X_{10}$ are independently hydrogen, hydrocarbyl, substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring. "Substituted amine," for example, refers to a group of formula —N($X_9$)($X_{10}$), wherein at least one of $X_9$ and $X_{10}$ are other than hydrogen. "Unsubstituted amine," for example, refers to a group of formula —N($X_9$)($X_{10}$), wherein $X_9$ and $X_{10}$ are both hydrogen.

By way of example, $X_9$ and $X_{10}$ may be independently selected from hydrogen, alkanoyl, alkenyl, alkoxyalkyl, alkoxyalkoxyalkyl, alkoxycarbonyl, alkyl, alkylaminoalkyl, alkylaminocarbonylalkyl, aryl, arylalkyl, cycloalkyl, (cycloalkyl)alkyl, cycloalkylcarbonyl, haloalkanoyl, haloalkyl, (heterocyclo)alkyl, heterocyclocarbonyl, hydroxyalkyl, an amino protecting group, —C(NH)NH$_2$, and —C(O)N($X_9$)($X_{10}$), wherein $X_9$ and $X_{10}$ are as previously defined; wherein the aryl; the aryl part of the arylalkyl; the cycloalkyl; the cycloalkyl part of the (cycloalkyl)alkyl and the cycloalkylcarbonyl; and the heterocycle part of the (heterocycle)alkyl and the heterocyclocarbonyl can be optionally substituted with one, two, three, four, or five substituents independently selected from the group consisting of alkanoyl, alkoxy, alkyl, cyano, halo, haloalkoxy, haloalkyl, hydroxyl, and nitro.

The term "aminoalkanoyl," as used herein, represents an amino group attached to the parent molecular moiety through an alkanoyl group.

The term "aminoalkyl," as used herein, represents an amino group attached to the parent molecular moiety through an alkyl group.

The term "aminocarbonyl," as used herein, represents an amino group attached to the parent molecular moiety through a carbonyl group.

The term "aminocarbonylalkyl," as used herein, represents an aminocarbonyl group attached to the parent molecular moiety through an alkyl group.

The term "aminosulfonyl," as used herein, represents an amino group attached to the parent molecular moiety through a sulfonyl group.

Unless otherwise indicated, the terms "amido" or "amide," as used herein alone or as part of another group, represents a group of formula —CON($X_9$)($X_{10}$), wherein $X_9$ and $X_{10}$ are as defined in connection with the terms "amine" or "amino." In general, "amido" or "amide" groups may be either substituted or unsubstituted. "Substituted amide," for example, refers to a group of formula —CON($X_9$)($X_{10}$), wherein at least one of $X_9$ and $X_{10}$ are other than hydrogen. "Unsubstituted amido," for example, refers to a group of formula —CON($X_9$)($X_{10}$), wherein $X_9$ and $X_{10}$ are both hydrogen.

The terms "amino protecting group," "protected amino," or "Pr" as used herein denote moieties that block reaction at the protected amino group while being easily removed under conditions that are sufficiently mild so as not to disturb other substituents of the various compounds. Common N-protecting groups comprise benzyl and acyl groups such as acetyl, benzoyl, 2-bromoacetyl, 4-bromobenzoyl, tert-butylacetyl, carboxaldehyde, 2-chloroacetyl, 4-chlorobenzoyl, a-chlorobutyryl, 4-nitrobenzoyl, o-nitrophenoxyacetyl, phthalyl, pivaloyl, propionyl, trichloroacetyl, and trifluoroacetyl; sulfonyl groups such as benzenesulfonyl, and p-toluenesulfonyl; carbamate forming groups such as benzyloxycarbonyl, benzyloxycarbonyl (Cbz), tert-butyloxycarbonyl (Boc), p-chlorobenzyloxycarbonyl, p-methoxybenzyloxycarbonyl, allyloxycarbonyl, fluorenylmethoxycarbonyl (Fmoc), and the like. A variety of protecting groups for the amino group and the synthesis thereof may be found in "Protective Groups in Organic Synthesis" by T. W. Greene and P. G. M. Wuts, John Wiley & Sons, 1999.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. For example, the term "aryl," may represent a phenyl group or a bicyclic or tricyclic fused ring system wherein one or more of the fused rings is a phenyl group. Bicyclic fused ring systems are exemplified by a phenyl group fused to a cycloalkyl group as defined herein, a cycloalkenyl group as defined herein, or another phenyl group. Tricyclic fused ring systems are exemplified by a bicyclic fused ring system fused to a cycloalkyl group as defined herein, a cycloalkenyl group as defined herein, or another phenyl group. Representative examples of aryl include, but are not limited to, anthracenyl, azulenyl, fluorenyl, indanyl, indenyl, naphthyl, phenyl, and tetrahydronaphthyl. Aryl groups having an unsaturated or partially saturated ring fused to an aromatic ring can be attached through the saturated or the unsaturated part of the group. The aryl groups of this invention can be optionally substituted with one, two, three, four, or five substituents independently selected from the group consisting of alkanoyl, alkenyl, alkoxy, alkoxyalkanoyl, alkoxyalkyl, alkoxycarbonyl, alkoxycarbonylalkyl, alkyl, alkynyl, amino, aminoalkyl, aminocarbonyl, aminocarbonylalkyl, aminosulfonyl, aryl, aryloxy, arylsulfanyl, carbonyloxy, cyano, halo, haloalkoxy, haloalkyl, heterocycle, (heterocycle)alkyl, heterocyclecarbonylalkenyl, heterocyclecarbonylalkyl, hydroxy, hydroxyalkyl, nitro, oxo, and —C(NH)NH$_2$, wherein the aryl; the aryl part of the aryloxy and the arylsulfanyl; the heterocycle; and the heterocycle part of the (heterocycle)alkyl, the heterocyclecarbonylalkenyl, and the heterocyclecarbonylalkyl can be further optionally substituted with one, two, or three substituents independently selected from the group consisting of alkoxyalkanoyl, alkoxycarbonyl, alkyl, alkylsulfonyl, aminocarbonyl, aminosulfonyl, cyano, halo, haloalkoxy, haloalkyl, hydroxy, nitro, oxo, and —C(NH)NH$_2$. In addition, the heterocycle and the heterocycle part of the (heterocycle)alkyl, the heterocyclecarbonylalkenyl, and the heterocyclecarbonylalkyl can be further optionally substituted with an additional aryl group, wherein the aryl can be optionally substituted with one, two, or three substituents independently selected from the group consisting of alkoxy, alkyl, cyano, halo, hydroxy, and nitro.

The term "arylalkenyl," as used herein, represents an aryl group attached to the parent molecular moiety through an alkenyl group.

The term "arylalkoxy," as used herein, represents an aryl group attached to the parent molecular moiety through an alkoxy group.

The term "arylalkoxyalkanoyl," as used herein, represents an arylalkoxy group attached to the parent molecular moiety through an alkanoyl group.

The term "arylalkoxycarbonyl," as used herein, represents an arylalkoxy group attached to the parent molecular moiety through a carbonyl group.

The term "arylalkylsulfanyl," as used herein, represents an arylalkyl group attached to the parent molecular moiety through a sulfur atom.

The term "arylalkylsulfanylalkyl," as used herein, represents an arylalkylsulfanyl group attached to the parent molecular moiety through an alkyl group.

The term "arylalkylsulfonyl," as used herein, represents an arylalkyl group attached to the parent molecular moiety through a sulfonyl group.

The term "arylcarbonyl," as used herein, represents an aryl group attached to the parent molecular moiety through a carbonyl group.

The term "aryloxy," as used herein, represents an aryl group attached to the parent molecular moiety through an oxygen atom.

The term "aryloxyalkoxy," as used herein, represents an aryloxy group attached to the parent molecular moiety through an alkoxy group.

The term "aryloxyalkyl," as used herein, represents an aryloxy group attached to the parent molecular moiety through an alkyl group.

The term "arylsulfanyl," as used herein, represents an aryl group attached to the parent molecular moiety through a sulfur atom.

The term "arylsulfanylalkoxy," as used herein, represents an arylsulfanyl group attached to the parent molecular moiety through an alkoxy group.

The term "arylsulfanylalkyl," as used herein, represents an arylsulfanyl group attached to the parent molecular moiety through an alkyl group. The alkyl part of the arylsulfanylalkyl can be optionally substituted with one or two substituents independently selected from the group consisting of alkoxy, alkoxycarbonyl, amino, aminocarbonyl, arylalkoxy, azido, carboxy, cycloalkyl, halo, heterocycle, (heterocycle)alkoxy, (heterocycle)carbonyl, and hydroxy.

The term "arylsulfinyl," as used herein, represents an aryl group attached to the parent molecular moiety through a sulfinyl group.

The term "arylsulfinylalkyl," as used herein, represents an arylsulfinyl group attached to the parent molecular moiety through an alkyl group. The alkyl part of the arylsulfinylalkyl can be optionally substituted with one or two amino groups.

The term "arylsulfonyl," as used herein, represents an aryl group attached to the parent molecular moiety through a sulfonyl group.

The term "arylsulfonylalkyl," as used herein, represents an arylsulfonyl group attached to the parent molecular moiety through an alkyl group. The alkyl part of the arylsulfonylalkyl can be optionally substituted with one or two amino groups.

The term "arylene", as used herein alone or part of another group refers to a divalent aryl radical of one to twelve carbon atoms. Non-limiting examples of "arylene" include phenylene, pyridinylene, pyrimidinylene and thiophenylene.

The terms "aralkyl," "arylalkyl," or "alkylene aryl," as used herein alone or as part of another group, denotes an -(alkylene)-X$_{11}$ radical, wherein X$_{11}$ is as defined in connection with the term "aryl." Non-limiting examples of "aralkyl" or "alkylene aryl" moieties include benzyl, —(CH$_2$)$_n$-phenyl where n is 2 to 6, or —CH-(phenyl)$_2$.

The terms "alkaryl" or "alkylaryl," as used herein alone or as part of another group, denotes an -(arylene)-$X_{11}$ radical, wherein $X_{11}$ is as defined in connection with the term "alkyl."

The term "azido," as used herein, represents a —$N_3$ moiety.

The term "carbocyclic," as used herein alone or as part of another group, denotes a ring wherein the atoms forming the ring backbone are selected from only carbon atoms. The carbocyclic rings may be optionally substituted, fully saturated or unsaturated, monocyclic or bicyclic, aromatic or nonaromatic, and generally include 3 to 20 carbon atoms.

The term "carbonyl," as used herein, represents a —C(O)— moiety.

The term "carbonyloxy," as used herein, represents an alkanoyl group attached to the parent molecular moiety through an oxygen atom.

The term "carboxy," as used herein, represents a —$CO_2H$ moiety.

The term "carboxyalkyl," as used herein, represents a carboxy group attached to the parent molecular moiety through an alkyl group.

The term "cyano," as used herein alone or as part of another group, denotes a group of formula —CN.

The term "cyanoalkyl," as used herein, represents a cyano group attached to the parent molecular moiety through an alkyl group.

The term "cycloalkyl," as used herein alone or as part of another group, denotes a cyclic saturated monovalent bridged or non-bridged hydrocarbon radical of three to twelve carbon atoms. Exemplary cycloalkyl moieties include cyclopropyl, cyclobutyl, cyclopentyl, cyclohexyl, or adamantyl. By way of example, the term "cycloalkyl" may represent a saturated ring system having three to twelve carbon atoms and one to three rings. Examples of cycloalkyl groups include cyclopropyl, cyclopentyl, bicyclo(3.1.1)heptyl, adamantyl, and the like. The cycloalkyl groups of this invention can be optionally substituted with one, two, three, four, or five substituents independently selected from the group consisting of alkoxy, alkoxycarbonyl, alkyl, aminoalkyl, arylalkoxy, aryloxy, arylsulfanyl, halo, haloalkoxy, haloalkyl, and hydroxy, wherein the aryl part of the arylalkoxy, the aryloxy, and the arylsulfanyl can be further optionally substituted with one, two, or three substituents independently selected from the group consisting of alkoxy, alkyl, halo, haloalkoxy, haloalkyl, and hydroxy.

The term "cycloalkylalkoxy," as used herein, represents a cycloalkyl group attached to the parent molecular moiety through an alkoxy group.

The term "(cycloalkyl)alkyl," as used herein, represents a cycloalkyl group attached to the parent molecular moiety through an alkyl group.

The term "cycloalkylcarbonyl," as used herein, represents a cycloalkyl group attached to the parent molecular moiety through a carbonyl group.

The term "cycloalkyloxy," as used herein, represents a cycloalkyl group attached to the parent molecular moiety through an oxygen atom.

The term "cycloalkenyl," as used herein, represents a nonaromatic ring system having three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Examples of cycloalkenyl groups include cyclohexenyl, octahydronaphthalenyl, norbornylenyl, and the like. The cycloalkenyl groups of this invention can be optionally substituted with one, two, three, four, or five substituents independently selected from the group consisting of alkoxy, alkoxycarbonyl, alkyl, aminoalkyl, arylalkoxy, aryloxy, arylsulfanyl, halo, haloalkoxy, haloalkyl, and hydroxy, wherein the aryl part of the arylalkoxy, the aryloxy, and the arylsulfanyl can be further optionally substituted with one, two, or three substituents independently selected from the group consisting of alkoxy, alkyl, halo, haloalkoxy, haloalkyl, and hydroxy.

The term "cycloalkenylalkyl," as used herein, represents a cycloalkenyl group attached to the parent molecular moiety through an alkyl group.

The term "ester," as used herein alone or as part of another group, denotes a group of formula —$COOX_{12}$ wherein $X_{12}$ is alkyl or aryl, each as defined in connection with such term.

The term "ether," as used herein alone or as part of another group, includes compounds or moieties which contain an oxygen atom bonded to two carbon atoms. For example, ether includes "alkoxyalkyl" which refers to an alkyl, alkenyl, or alkynyl group substituted with an alkoxy group.

The term "formyl," as used herein, represents a —CHO moiety.

The term "formylalkyl," as used herein, represents a formyl group attached to the parent molecular moiety through an alkyl group.

The terms "halide," "halogen" or "halo" as used herein alone or as part of another group refer to chlorine, bromine, fluorine, and iodine.

The term "haloalkyl," as used herein, represents an alkyl group substituted by one, two, three, or four halogen atoms.

The term "haloalkanoyl," as used herein, represents a haloalkyl group attached to the parent molecular moiety through a carbonyl group.

The term "haloalkoxy," as used herein, represents a haloalkyl group attached to the parent molecular moiety through an oxygen atom.

The term "heteroatom" shall mean atoms other than carbon and hydrogen.

The terms "heteroaralkyl" and "alkylene heteroaryl," as used herein alone or as part of another group, denotes an -(alkylene)-$X_{13}$ radical, wherein $X_{13}$ is as defined in connection with the term "heteroaryl." Non-limiting examples of "heteroaralkyl" or "alkylene heteroaryl" moieties include —$(CH_2)_n$-indolyl where n is 1 to 6.

The term "heteroalkylene," as used herein, represents a divalent group of two to eight atoms derived from a saturated straight or branched chain containing one or two heteroatoms independently selected from the group consisting of nitrogen, oxygen, and sulfur, wherein the remaining atoms are carbon. The heteroalkylene groups of the present invention can be attached to the parent molecular moiety through the carbon atoms or the heteroatoms in the chain.

The term "heteroalkenylene," as used herein, represents a divalent group of three to eight atoms derived from a straight or branched chain containing at least one carbon-carbon double bond that contains one or two heteroatoms independently selected from the group consisting of nitrogen, oxygen, and sulfur, wherein the remaining atoms are carbon. The heteroalkenylene groups of the present invention can be attached to the parent molecular moiety through the carbon atoms or the heteroatoms in the chain.

The term "heterocyclo" or "heterocycle," as used herein, represents a monocyclic, bicyclic, or tricyclic ring system wherein one or more rings is a four-, five-, six-, or seven-membered ring containing one, two, or three heteroatoms independently selected from the group consisting of nitrogen, oxygen, and sulfur. Monocyclic ring systems are exemplified by any 3- or 4-membered ring containing a heteroatom independently selected from the group consisting of oxygen, nitrogen and sulfur; or a 5-, 6- or 7-membered ring containing one, two or three heteroatoms wherein the heteroatoms are independently selected from the group consisting of nitrogen, oxygen and sulfur. The 3- and 4-membered rings have no double bonds, the 5-membered ring has from 0-2 double bonds and the 6- and 7-membered rings have from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, a cycloalkenyl group, as defined herein, or another monocyclic heterocycle ring system. Representative examples of bicyclic ring system include but are not limited to, benzimidazole, benzothiazole, benzothiophene, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. Tricyclic rings systems are exemplified by any of the above bicyclic ring systems fused to an aryl group as defined herein, a cycloalkyl group as defined herein, a cycloalkenyl group as defined herein, or another monocyclic heterocycle ring system. Representative examples of tricyclic ring systems include, but are not limited to, acridine, carbazole, carboline, dibenzofuran, dibenzothiophene, naphthofuran, naphthothiophene, oxanthrene, phenazine, phenoxathiin, phenoxazine, phenothiazine, thianthrene, thioxanthene, xanthene, and the like. Heterocycle groups can be attached to the parent molecular moiety through a carbon atom or a nitrogen atom in the group.

The heterocyclo groups of the present invention can be optionally substituted with one, two, three, four, or five substituents independently selected from the group consisting of alkanoyl, alkanoylalkyl, alkenyl, alkoxy, alkoxyalkoxycarbonyl, alkoxyalkyl, alkoxycarbonyl, alkoxycarbonylalkyl, alkyl, alkylsulfanylalkyl, alkynyl, amino, aminoalkanoyl, aminoalkyl, aminocarbonyl, aminocarbonylalkyl, aminosulfonyl, aryl, arylalkoxyalkanoyl, arylalkoxycarbonyl, arylalkyl, arylalkylsulfonyl, arylcarbonyl, aryloxy, arylsulfanyl, arylsulfanylalkyl, arylsulfonyl, carbonyloxy, carboxy, cyano, cyanoalkyl, cycloalkyl, (cycloalkyl)alkyl, cycloalkylcarbonyl, formyl, formylalkyl, halo, haloalkoxy, haloalkyl, heterocycle, (heterocycle)alkyl, (heterocycle)alkylidene, heterocyclecarbonyl, heterocyclecarbonylalkyl, hydroxy, hydroxyalkyl, nitro, oxo, spirocycle, spiroheterocycle, and —C(NH)NH$_2$; wherein the aryl; the aryl part of the arylalkylsulfonyl, the arylcarbonyl, the aryloxy, the arylalkoxyalkanoyl, the arylalkoxycarbonyl, the arylalkyl, the arylsulfanyl, the arylsulfanylalkyl, and the arylsulfonyl; the heterocycle; and the heterocycle part of the (heterocycle)alkyl, the (heterocycle)alkylidene, the heterocyclecarbonyl, and the heterocyclecarbonylalkyl can be further optionally substituted with one, two, three, four, or five substituents independently selected from the group consisting of alkanoyl, alkoxy, alkoxyalkoxycarbonyl, alkoxycarbonyl, alkyl, halo, haloalkoxy, haloalkyl, hydroxy, hydroxyalkyl, and nitro.

The term "(heterocyclo)alkoxy," as used herein, represents a heterocyclo group attached to the parent molecular moiety through an alkoxy group.

The term "(heterocyclo)alkyl," as used herein, represents a heterocyclo group attached to the parent molecular moiety through an alkyl group.

The term "(heterocyclo)alkylidene," as used herein, represents a heterocyclo group attached to the parent molecular moiety through an alkylidene group.

The term "heterocyclocarbonyl," as used herein, represents a heterocyclo group attached to the parent molecular moiety through a carbonyl group.

The term "heterocyclocarbonylalkenyl," as used herein, represents a heterocyclecarbonyl group attached to the parent molecular moiety through an alkenyl group.

The term "heterocyclocarbonylalkyl," as used herein, represents a heterocyclocarbonyl group attached to the parent molecular moiety through an alkyl group.

The term "(heterocyclo)oxy," as used herein, represents a heterocyclo group attached to the parent molecular moiety through an oxygen atom.

The term "(heterocyclo)sulfanyl," as used herein, represents a heterocyclo group attached to the parent molecular moiety through a sulfur atom.

The term "(heterocyclo)sulfanylalkyl," as used herein, represents a heterocyclosulfanyl group attached to the parent molecular moiety through an alkyl group.

The term "heteroaromatic" or "heteroaryl" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxyl, protected hydroxyl, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "hydroxy" or "hydroxyl," as used herein alone or as part of another group, denotes a group of formula —OH.

The term "hydroxyalkyl," as used herein, represents a hydroxy group attached to the parent molecular moiety through an alkyl group.

The term "hydroxyl protecting group," as used herein alone or as part of another group, denote a group capable of protecting a free hydroxyl group ("protected hydroxyl") which, subsequent to the reaction for which protection is employed, may be removed without disturbing the remainder of the molecule. Exemplary hydroxylprotecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxyl group and the synthesis thereof may be found in "Protective Groups in Organic Synthesis" by T. W. Greene and P. G. M. Wuts, John Wiley & Sons, 1999.

The term "keto," as used herein alone or as part of another group, denotes a double bonded oxygen moiety (i.e., =O).

The term "nitro," as used herein alone or as part of another group, denotes a group of formula —NO$_2$.

The term "oxo," as used herein, represents a (=O) moiety.

The term "spirocycle," as used herein, represents an alkyl diradical of two to eight atoms, each end of which is attached to the same carbon atom of the parent molecular moiety.

The term "spiroheterocycle," as used herein, represents a heteroalkylene diradical, each end of which is attached to the same carbon atom of the parent molecular moiety. Examples of spiroheterocycles include dioxolanyl, tetrahydrofuranyl, pyrrolidinyl, and the like.

The term "sulfinyl," as used herein, represents a —S(=O)— moiety.

The term "sulfonyl," as used herein, represents —S(=O)$_2$— moiety

Unless otherwise indicated, the "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxyl, protected hydroxyl, keto, acyl, acyloxy, nitro, amino, amido, nitro, cyano, thiol, ketals, acetals, esters, ethers, and thioethers.

The term "thioester," as used herein alone or as part of another group, denotes a group of formula —C(O)—S—X$_{14}$, wherein X$_{14}$ is alkyl or aryl as defined in connection with such term.

The term "thioether," as used herein alone or as part of another group, denotes compounds and moieties that contain a sulfur atom bonded to two different carbon or hetero atoms (i.e., —S—), and also includes compounds and moieties containing two sulfur atoms bonded to each other, each of which is also bonded to a carbon or hetero atom (i.e., dithioethers (—S—S—)). Examples of thioethers include, but are not limited to, alkylthioalkyls, alkylthioalkenyls, and alkylthioalkynyls. The term "alkylthioalkyls" includes compounds with an alkyl, alkenyl, or alkynyl group bonded to a sulfur atom that is bonded to an alkyl group. Similarly, the term "alkylthioalkenyls" and alkylthioalkynyls" refer to compounds or moieties where an alkyl, alkenyl, or alkynyl group is bonded to a sulfur atom that is covalently bonded to an alkynyl group.

The term "thiol," as used herein alone or as part of another group, denotes a group of formula —SH.

Having described the invention in detail, it will be apparent that modifications and variations are possible without departing the scope of the invention defined in the appended claims. Furthermore, it should be appreciated that all examples in the present disclosure are provided as non-limiting examples.

In general, all reactions were run under an atmosphere of nitrogen unless otherwise indicated. Prior to use of solvents in reactions, they were purified by passing the degassed solvents through a column of activated alumina and transferred by an oven-dried syringe or cannula. Thin layer chromatography was performed on Merck TLC plates (silica gel 60 F$_{254}$). $^1$H-NMR and $^{13}$C-NMR were recorded on a Varian Inova 400 (400 MHz) or a Bruker Avance DPX-250 (250 MHz) instrument. The HRMS data were measured on an Agilent 1100 Series MSD/TOF with electrospray ionization. LC/MS data were measured on an Agilent 1100 LC/MSD-VL with electrospray ionization. Sulfonyl azide (SZ8) prepared as reported procedure.

EXAMPLE 1

Preparation of Building Blocks 1.1 Sulfonylazide (SZ8)

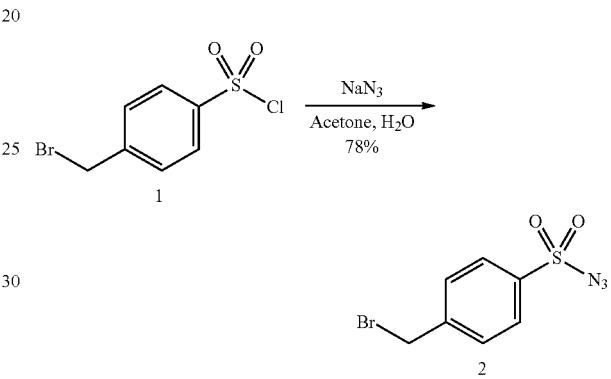

A saturated solution of sodium azide (1.2 g, 18.5 mmol) in water was added slowly to a saturated solution of 1 (5 g, 18.5 mmol) in acetone at room temperature. The mixture was stirred at room temperature for 3 hours. Ethyl acetate (50 mL) and saturated aqueous potassium carbonate solution (50 mL) were added. After extraction with ethyl acetate (50 mL×3), the combined organic phases were dried over anhydrous sodium sulfate and concentrated. The product 2 (SZ8) (4.0 g, 78%) was obtained by flash chromatography (hexanes:EtOAc=24:1). Rf=0.4 (hexanes:EtOAc=8:1). $^1$H-NMR (400 MHz, CDCl$_3$) δ: 7.91 (d, J=8.3 Hz, 2H), 7.60 (d, J=8.3 Hz, 2H), 4.50 (s, 2H) ppm. $^{13}$C-NMR (100 MHz, CDCl$_3$) δ: 145.2, 138.4, 130.4, 128.2, 31.1 ppm. HRMS (ESI$^+$) for [M+NH$_4$]$^+$; calculated: 292.97024. found: 292.96949 (error m/z=−2.54 ppm).

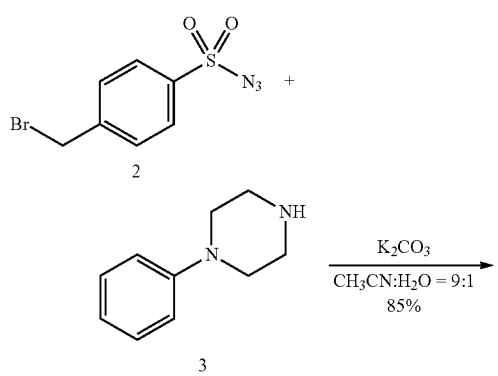

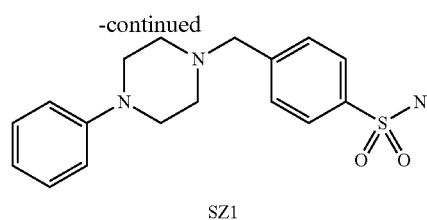

SZ1

A mixture of (SZ8) (100 mg, 0.36 mmol), 3 (60 mg, 0.36 mmol) and potassium carbonate (100 mg, 0.72 mmol) in acetonitrile and water (9:1) was stirred at room temperature for 12 hours. The reaction mixture was then mixed with ethyl acetate (20 mL) and water (20 mL), and extracted with ethyl acetate (20 mL×3). The combined organic phases were dried over anhydrous sodium sulfate and concentrated. Product (SZ1) (110 mg, 85%) was obtained by flash chromatography (hexane:EtOAc=12:1). Rf=0.45 (hexanes: EtOAc=4:1). $^1$H-NMR (400 MHz, CDCl$_3$) δ: 7.91 (d, J=8.2 Hz, 2H), 7.62 (d, J=8.2 Hz, 2H), 7.26-7.24 (m, 2H), 6.94-6.84 (m, 3H), 3.66 (s, 2H), 3.23-3.20 (m, 4H), 2.64-2.61 (m, 4H) ppm. $^{13}$C-NMR (100 MHz, CDCl$_3$) δ: 151.2, 146.5, 137.1, 129.9, 129.1, 127.5, 119.8, 116.1, 62.2, 53.2, 49.1 ppm. HRMS (ESI$^+$) for [M+H]$^+$; calculated: 358.13322. found: 358.13320 (error m/z=−0.07 ppm).

1.2 Sulfonylazide (SZ2)

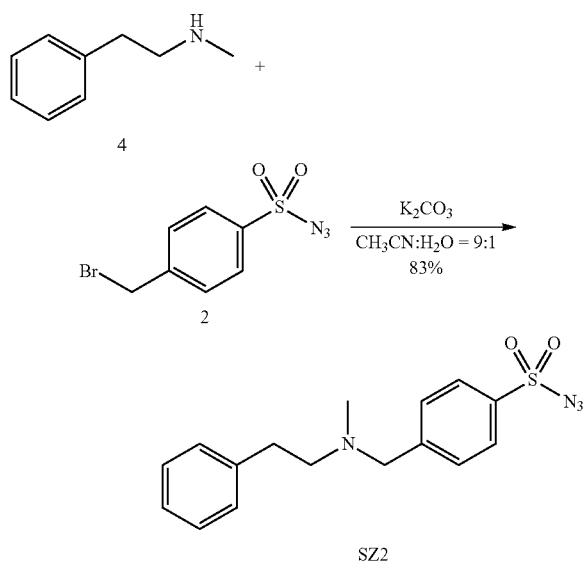

SZ2

The mixture of (SZ8) (100 mg, 0.36 mmol), 4 (50 mg, 0.36 mmol) and potassium carbonate (100 mg, 0.72 mmol) in acetonitrile and water (9:1), was stirred at room temperature for 12 hours. After mixed with ethyl acetate (20 mL) and water (20 mL), the system was extracted by ethyl acetate (20 mL×3). The combined organic phase was dried by anhydrous sodium sulfate and concentrated. Product (SZ2) (100 mg, 83%) was obtained by flash chromatography (hexane: EtOAc=14:1; Rf=0.5 in hexane:EtOAc=4:1). $^1$H-NMR (400 MHz, CDCl$_3$) δ: 7.84 (d, J=8.2 Hz, 2H), 7.48 (d, J=8.1 Hz, 2H), 7.30-7.16 (m, 5H), 3.63 (s, 2H), 2.82 (t, J=8.0 Hz, 2H), 2.66 (t, J=8.0 Hz, 2H), 2.30 (s, 3H) ppm. $^{13}$C-NMR (100 MHz, CDCl$_3$) δ: 147.7, 140.2, 136.7, 129.7, 128.7, 128.3, 127.4, 126.1, 61.6, 59.2, 42.2, 33.9 ppm. HRMS (ESI$^+$) for [M+H]$^+$; calculated: 331.12232. found: 331.12269 (error m/z=1.11 ppm).

1.3 Sulfonylazide (SZ3)

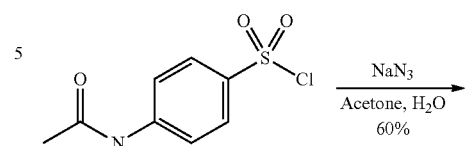

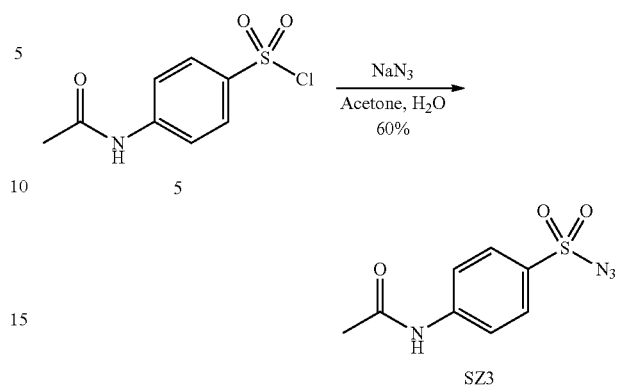

SZ3

(SZ3) was prepared starting from 5 using the procedure described for the preparation of 2 with 60% yield (hexane: EtOAc=2:1; Rf=0.25 in hexane:EtOAc=1:1). $^1$H-NMR (400 MHz, CDCl$_3$) δ: 8.10 (s, 1H), 7.84 (d, J=8.2 Hz, 2H), 7.74 (d, J=8.2 Hz, 2H), 2.21 (s, 3H) ppm. $^{13}$C-NMR (100 MHz, CDCl$_3$) δ: 169.0, 143.8, 132.2, 128.7, 119.4, 24.5 ppm. HRMS (ESI$^+$) for [M+NH$_4$]$^+$; calculated: 258.06554. found: 258.06476 (error m/z=−3.02 ppm).

1.4 Sulfonylazide (SZ4)

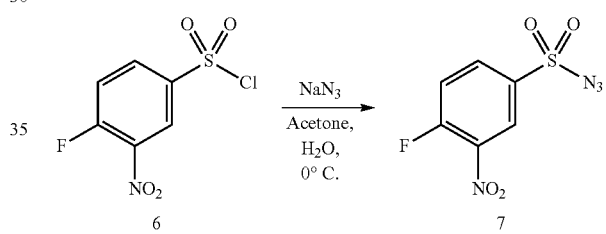

A saturated solution of sodium azide (280 mg, 4.30 mmol) in water was added slowly to a saturated solution of 6 (see Wendt et al., J. Med. Chem. 2006, 49, 1165-1181) (500 mg, 2.1 mmol) in acetone at 0° C. The mixture was stirred at 0° C. for 3 hours. Ethyl acetate (20 mL) and saturated aqueous potassium carbonate solution (20 mL) were added to the mixture and after extraction with ethyl acetate (20 mL×3), the combined organic phases were dried over anhydrous sodium sulfate and concentrated. Product 7 was used without further purification in the next reaction.

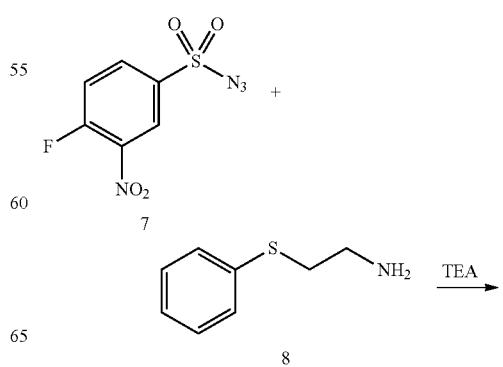

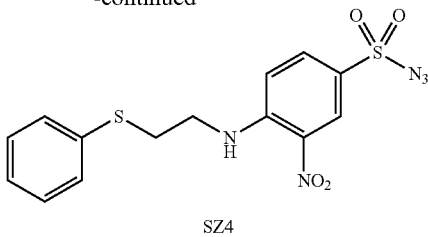

SZ4

A mixture of compounds 7 (see Wendt et al., supra) (280 mg, more than 0.91 mmol) and 8 (224 mg, 0.91 mmol) in triethylamine (5 mL) was stirred overnight at room temperature. To the reaction mixture was added silica (600 mg) and the solvent was removed under reduced pressure. Product (SZ4) (260 mg, 68.5% over two steps) was obtained by flash chromatography (hexane:EtOAc=8:1-2:1; Rf=0.4 in hexane:EtOAc=2:1). $^1$H-NMR (400 MHz, CDCl$_3$) δ: 8.77 (d, J=2.4 Hz, 1H), 8.71 (d, J=2.4 Hz, 1H), 7.79 (dd, J=9.2, 2.4 Hz, 1H), 7.39 (dd, J=8.4, 1.2 Hz, 2H), 7.30-7.24 (m, 3H), 6.85 (d, J=9.2 Hz, 1H), 3.60 (dd, J=9.0, 6.4 Hz, 2H), 3.22 (t, J=6.8 Hz, 2H) ppm. $^{13}$C-NMR (100 MHz, CDCl$_3$) δ: 148.1, 134.2, 133.6, 131.1, 129.8, 129.5, 128.5, 127.7, 124.5, 115.0, 42.3, 33.3 ppm. HRMS (ESI$^+$) for [M+H]$^+$; calculated: 380.04817. found: 380.04795 (error m/z=−0.59 ppm).

1.5 Sulfonylazide (SZ5)

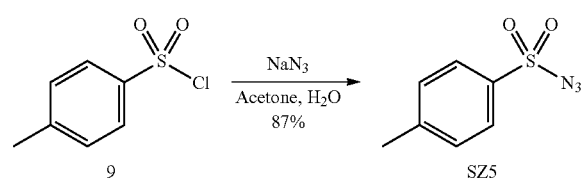

The known (SZ5) (Waser et al., J. Am. Chem. Soc. 2006, 128(35), 11693-11712) was prepared starting from 9 using the procedure described for the preparation of 2 in 87% yield. (DCM: MeOH=60:1; Rf=0.4 in DCM: MeOH=20:1) $^1$H-NMR (250 MHz, CDCl$_3$) δ: 7.84 (d, J=8.4 Hz, 2H), 7.41 (d, J=8.1 Hz, 2H), 2.48 (s, 3H) ppm.

1.6 Sulfonylazide (SZ6)

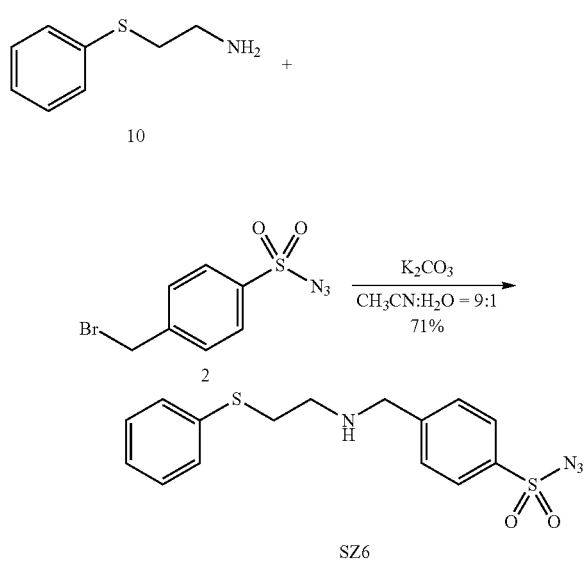

The mixture of (SZ8) (100 mg, 0.36 mmol), 10 (55 mg, 0.36 mmol) and potassium carbonate (100 mg, 0.72 mmol) in acetonitrile and water (9:1), was stirred at room temperature for 12 hours. The reaction mixture was then mixed with ethyl acetate (20 mL) and water (20 mL), and extracted by ethyl acetate (20 mL×3). The combined organic phases were dried over anhydrous sodium sulfate and concentrated. Product (SZ6) (89 mg, 71%) was obtained by flash chromatography (hexane:EtOAc=3:1). Rf=0.45 (hexanes:EtOAc=1:1). $^1$H-NMR (400 MHz, CDCl$_3$) δ: 7.86 (d, J=8.4 Hz, 2H), 7.53 (d, J=8.4 Hz, 2H), 7.33-7.18 (m, 5H), 3.88 (s, 3H), 3.08 (t, J=6.0 Hz, 2H), 2.83 (t, J=6.0 Hz, 2H) ppm. $^{13}$C-NMR (100 MHz, CDCl$_3$) δ: 148.2, 136.8, 135.5, 129.8, 129.0, 127.6, 126.4, 52.6, 47.5, 34.2 ppm. HRMS (ESI$^+$) for [M+H]$^+$; calculated: 349.07874. found: 349.07937 (error m/z=1.79 ppm).

1.7 Sulfonyl Azide (SZ7)

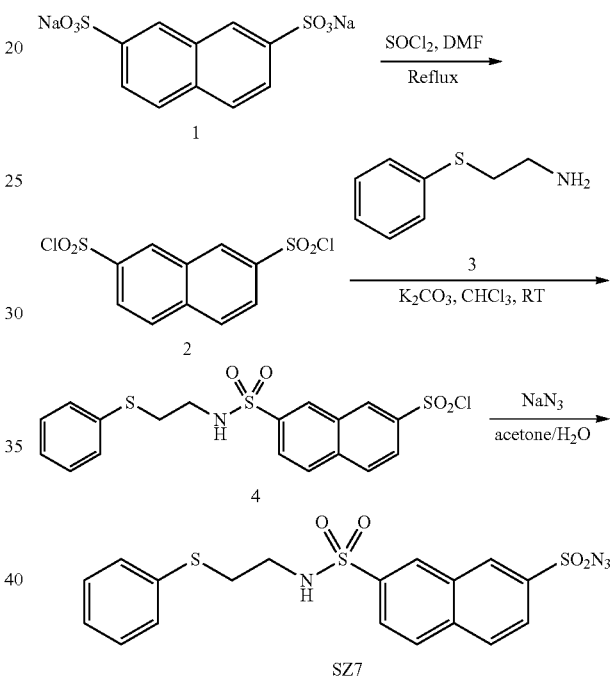

The mixture of compound 1 (664 mg, 2 mmol), SOCl$_2$ (4 mL), and DMF (0.1 mL) were refluxed for 2 h. Cold water (15 mL) was added, the mixture was extracted with DCM (4×15 mL), and the combined organic extracts were dried over Na$_2$SO$_4$. A quick filtration through a pad of silica gel, evaporation, and vacuum-drying gave the crude product 2 according to similar procedure (see Paruch et al., J. Org. Chem.; 2000; 65, 8774-8782). And compound 2 was used directly for next step.

A solution of compounds 2 and 3 (155 mg, 1 mmol) and potassium carbonate (200 mg, 1.44 mmol) in CHCl$_3$, was stirred at room temperature for 12 hours. The reaction mixture was then concentrated, mixed with ethyl acetate (20 mL) and water (20 mL), and extracted by ethyl acetate (20 mL×3). The combined organic phases were dried over anhydrous sodium sulfate and concentrated. The obtained crude product 4 was dissolved in acetone and added a solution of sodium azide (70 mg, 1 mmol) in water dropwise at 0° C. The mixture was stirred at 0° C. for 3 hours. Ethyl acetate (20 mL) and saturated aqueous potassium carbonate solution (20 mL) were added to the mixture and after extraction with ethyl acetate (20 mL×3), the combined organic phases were dried over anhydrous sodium sulfate and concentrated. Product (SZ7) (315 mg, 70%) was obtained by flash chromatography (hexane:EtOAc=4:1; Rf=0.6 in hexane:EtOAc=1:1).

1.8 Sulfonyl Azide (SZ9)

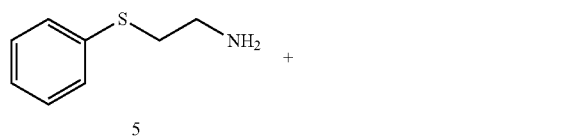

The mixture of 5 (276 mg, 1 mmol), (SZ8) (77 mg, 0.5 mmol) and potassium carbonate (200 mg, 1.44 mmol) in acetonitrile and water (9:1), was stirred at room temperature for 12 hours. After mixed with ethyl acetate (20 mL) and water (20 mL), the system was extracted by ethyl acetate (20 mL×3). The combined organic phase was dried by anhydrous sodium sulfate and concentrated. Product (SZ9) (154 mg, 60%) was obtained by flash chromatography (hexane: EtOAc=6:1; Rf=0.2 in hexane:EtOAc=4:1). $^1$H-NMR (400 MHz, CDCl$_3$) δ: 7.87 (d, J=8.3 Hz, 4H), 7.57 (d, J=8.3 Hz, 4H), 7.24-7.15 (m, 5H), 3.72 (s, 4H), 3.07 (t, J=7.2 Hz, 2H), 2.76 (t, J=7.1 Hz, 2H) ppm. $^{13}$C-NMR (100 MHz, CDCl$_3$) δ: 146.6, 137.4, 129.6, 129.2, 129.0, 127.9, 127.6, 126.3, 57.9, 52.7, 31.5 ppm. HRMS (ESI$^+$) for [M+H]$^+$; calculated: 544.08899. found: 544.08874 (error m/z=−0.46 ppm).

1.9 Sulfonyl Azide (SZ10)

The solution of commercially available compound 6 (1 g, 3.74 mmol) in DCM was bubbled by ammonia gas at 0° C. for 10 min. After mixed with DCM (20 mL) and water (20 mL), the system was extracted by DCM (20 mL×3). The combined organic phase was dried by anhydrous sodium sulfate and concentrated. Product 7 (900 mg, 96%) was obtained by flash chromatography (hexane:EtOAc=3:1; Rf=0.5 in hexane:E-tOAc=1:1). $^1$H-NMR (400 MHz, DMSO-d6) δ: 7.81 (d, J=8.4 Hz, 2H), 7.63 (d, J=8.4 Hz, 2H), 7.39 (s, 2H), 4.76 (s, 2H) ppm. $^{13}$C-NMR (100 MHz, DMSO-d6) δ: 143.8, 141.9, 129.8, 126.0, 32.9 ppm.

The compound 7 (900 mg, 3.6 mmol), benzylaldehyde (381 mg, 3.6 mmol) and para-methylbenzylsulfonic acid (10 mg) in benzene had been refluxed for 10 h with Dean-stack condenser. The system was cooled down and extracted by ethyl acetate (20 mL×3). The combined organic phase was dried by anhydrous sodium sulfate, concentrated, and gave the product 8, which was used for next step directly. The mixture of 8, the known (SZ6) (1.25 g, 3.6 mmol) and potassium carbonate (1.0 g, 7.2 mmol) in acetonitrile and water (9:1), was refluxing for 24 hours. After cooled down and mixed with ethyl acetate (20 mL) and water (20 mL), the system was extracted by ethyl acetate (20 mL×3). The combined organic phase was dried by anhydrous sodium sulfate and concentrated. The interesting thing here is the hydrolyzation of the imine happened smoothly under this basic condition. And product (SZ10) (930 mg, 50%) was obtained by flash chromatography (hexane:EtOAc=2:1; Rf=0.2 in hexane:EtOAc=2:1). $^1$H-NMR (400 MHz, CDCl$_3$) δ: 7.83 (d, J=8.4 Hz, 4H), 7.55 (d, J=8.4 Hz, 2H), 7.47 (d, J=8.4 Hz, 2H), 7.24-7.14 (m, 5H), 5.00 (bs, 2H), 3.68 (s, 2H), 3.67 (s, 2H), 3.06 (t, J=6.8 Hz, 2H), 2.75 (t, J=6.8 Hz, 2H) ppm. $^{13}$C-NMR (100 MHz, CDCl$_3$) δ: 147.0, 144.1, 140.9, 137.1, 135.8, 129.6, 129.2, 129.1, 128.9, 127.5, 126.5, 126.2, 58.1, 58.0, 53.0, 31.6 ppm. HRMS (ESI$^+$) for [M+H]$^+$; calculated: 518.09849. found: 518.09993 (error m/z=2.76 ppm).

1.10 Sulfonyl Azide (SZ11)

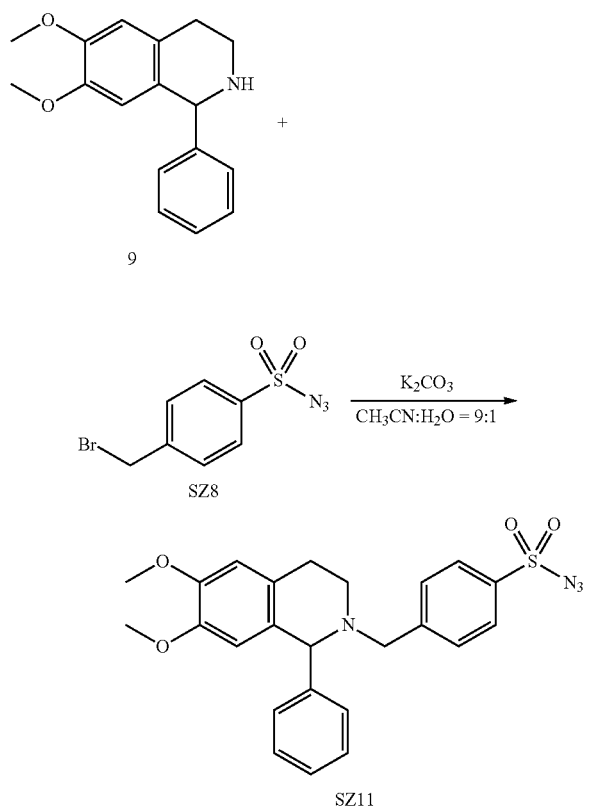

(SZ11) was prepared through the procedure described for the preparation of (SZ9) in 87% yield by using (SZ8) and known compound 9, which is prepared according to the reported method. $^1$H-NMR (400 MHz, CDCl$_3$) δ: 7.82 (d, J=8.4 Hz, 2H), 7.53 (d, J=8.0 Hz, 2H), 7.36-7.22 (m, 5H), 6.62 (s, 1H), 6.20 (s, 1H), 4.57 (s, 1H), 3.83 (d, J=14.8 Hz, 1H), 3.80 (s, 3H), 3.56 (s, 3H), 3.39 (d, J=14.8 Hz, 1H), 3.00-2.98 (m, 2H), 2.71 (d, J=15.2 Hz, 1H), 2.52 (d, J=15.2 Hz, 1H) ppm. $^{13}$C-NMR (100 MHz, CDCl$_3$) δ: 147.8, 147.2, 146.8, 143.4, 136.3, 129.5, 129.2, 129.1, 128.1, 127.2, 127.0, 126.2, 111.4, 110.6, 68.1, 57.9, 55.4, 47.3, 28.2 ppm. HRMS (ESI$^+$) for [M+H]$^+$; calculated: 465.15965. found: 465.15970 (error m/z=0.1 ppm).

1.11 Sulfonyl Azide (SZ12)

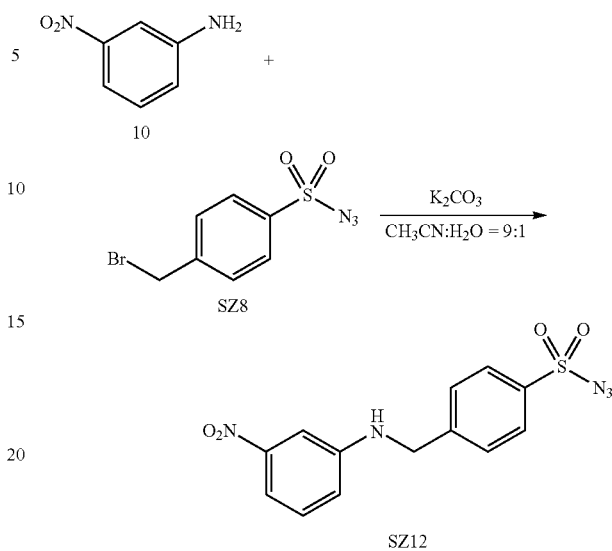

(SZ12) was prepared starting from 10 and (SZ8) using the procedure described for the preparation of (SZ9) in 67% yield. $^1$H-NMR (400 MHz, CDCl$_3$) δ: 7.90 (d, J=6.8 Hz, 2H), 7.59-7.25 (m, 5H), 6.84 (d, J=7.6 Hz, 1H), 4.53 (s, 2H) ppm. $^{13}$C-NMR (100 MHz, CDCl$_3$) δ: 148.0, 146.2, 130.0, 128.3, 128.1, 128.0, 127.6, 118.7, 112.8, 106.7, 47.3 ppm. HRMS (ESI$^+$) for [M+K]$^+$; calculated: 372.01633. found: 372.01449 (error m/z=−4.94 ppm).

1.12 Sulfonyl Azide (SZ13)

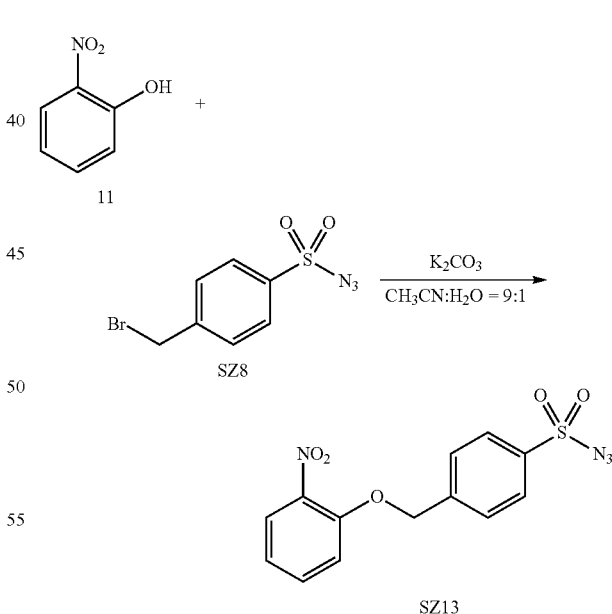

(SZ13) was prepared starting from 11 and (SZ8) using the procedure described for the preparation of (SZ9) in 40% yield. $^1$H-NMR (400 MHz, CDCl$_3$) δ: 7.89-7.84 (m, 3H), 7.61-7.33 (m, 5H), 4.48 (s, 2H) ppm. $^{13}$C-NMR (100 MHz, CDCl$_3$) δ: 143.2, 141.1, 134.3, 134.0, 129.0, 128.5, 127.7, 125.8, 125.1, 53.6 ppm. HRMS (ESI$^+$) for [M+NH$_4$]$^+$; calculated: 352.0716. found: 352.0719 (error m/z=0.8 ppm).

1.13 Sulfonyl Azide (SZ14)

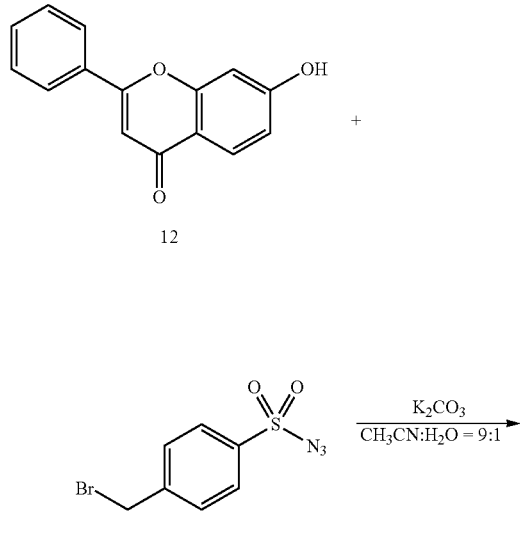

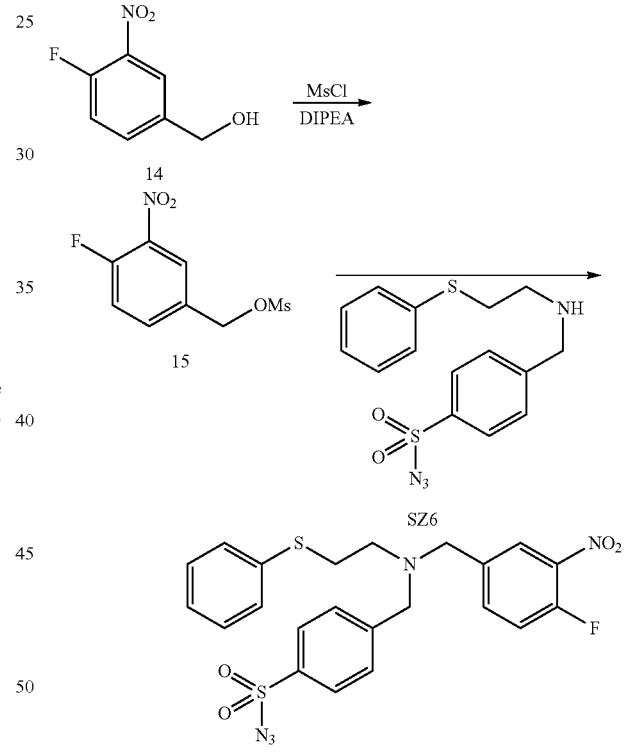

(SZ14) was prepared starting from 12 and (SZ8) using the procedure described for the preparation of (SZ9) in 45% yield. $^1$H-NMR (400 MHz, CDCl$_3$) δ: 8.08 (dd, J=8.8, 3.6 Hz, 1H), 7.87-7.82 (m, 4H), 7.50-7.48 (m, 5H), 7.36 (d, J=2.0 Hz, 1H), 6.91 (dd, J=8.8, 2.0 Hz, 1H), 6.75 (d, J=4.0 Hz, 1H) 4.47 (s, 2H) ppm. $^{13}$C-NMR (100 MHz, CDCl$_3$) δ: 177.1, 163.8, 156.3, 152.7, 142.8, 134.4, 131.8, 131.0, 129.0, 128.9, 128.6, 127.4, 126.2, 122.6, 119.4, 112.0, 107.6, 53.6 ppm. HRMS (ESI$^+$) for [M+H]$^+$; calculated: 434.08052. found: 434.07955 (error m/z=−2.24 ppm).

1.14 Sulfonyl Azide (SZ15)

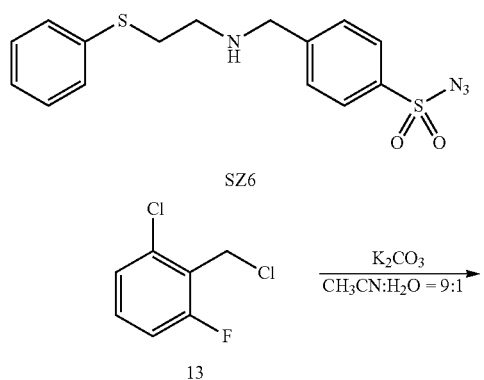

(SZ15) was prepared starting from 13 and known (SZ6) using the procedure described for the preparation of (SZ9) in 54% yield. $^1$H-NMR (400 MHz, CDCl$_3$) δ: 7.78 (d, J=8.0 Hz, 2H), 7.51 (d, J=8.0 Hz, 2H), 7.18-7.11 (m, 7H), 6.94-6.90 (m, 1H), 3.85 (s, 2H), 3.73 (s, 2H), 3.05 (t, J=7.6 Hz, 2H), 2.77 (t, J=7.6 Hz, 2H) ppm. $^{13}$C-NMR (100 MHz, CDCl$_3$) δ: 161.9 (d, $^1J_{CF}$=247 Hz), 147.8, 136.6, 136.3, 135.8, 129.5, 129.4, 128.9 (d, $^2J_{CF}$=26 Hz), 127.1, 126.0, 125.5, 124.1 (d, $^3J_{CF}$=16.8 Hz), 113.9 (d, $^2J_{CF}$=23.3 Hz), 57.8, 53.6, 49.4, 31.1 ppm.

1.15 Sulfonyl Azide (SZ16)

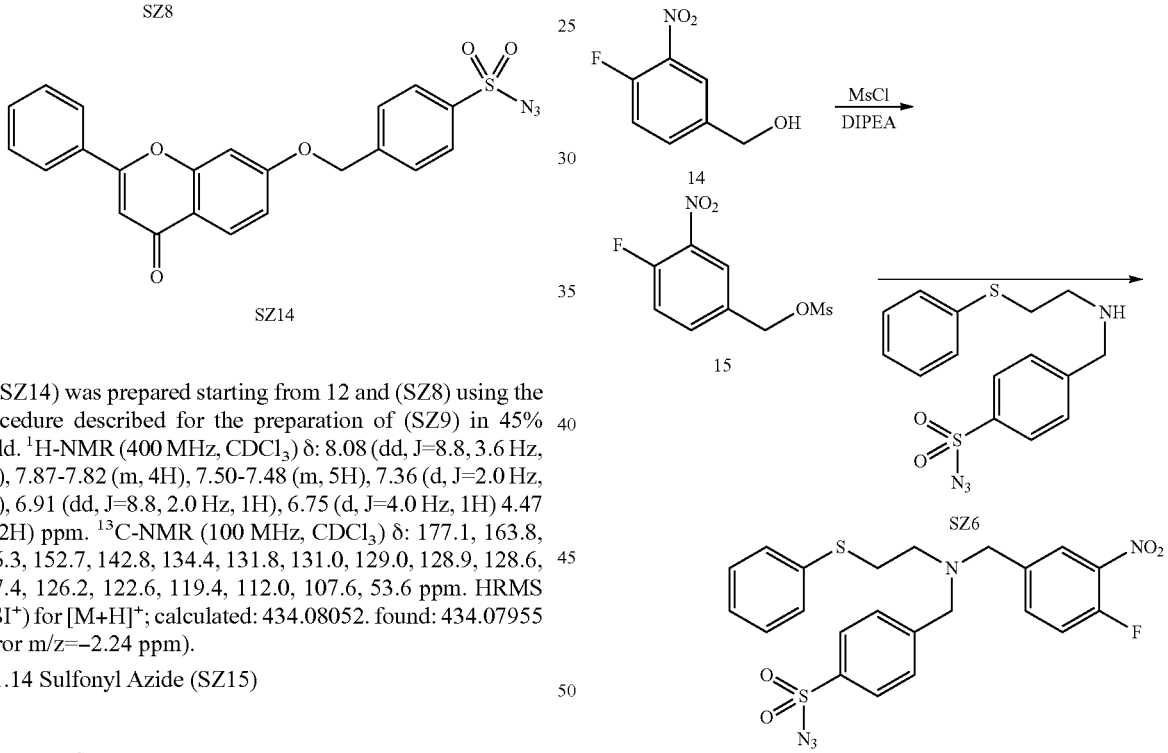

(SZ16) was prepared by two steps. First, the mixture of 14 (570 mg, 3.3 mmol) and mesyl chloride (0.45 ml, 5.2 mmol) in N,N-Diisopropylethylamine (10 ml) was stirred for 3 hours and then (SZ6) (1.15 g, 3.3 mmol) was added. After stirring for another 3 hours, 30 ml ethyl acetate and 30 ml CuSO$_4$ aqueous solution were added. The aqueous phase was extracted twice with 30 ml ethyl acetate and the combined organic phase is dried over Na$_2$SO$_4$ and concentrated down. (SZ16) (310 mg, 19% over two steps) was obtained by flash chromatography (hexane:EtOAc=6:1; Rf=0.3 in hexane:EtOAc=2:1). $^1$H-NMR (400 MHz, CDCl$_3$) δ: 8.01 (d, J=6.0 Hz, 1H), C 7.58-7.56 (m, 3H), 7.23-7.14 (m, 6H), 3.70 (s, 2H), 3.63 (s, 2H), 3.05 (t, J=7.3 Hz, 2H), 2.74 (t, J=7.6 Hz, 2H) ppm. $^{13}$C-NMR (100 MHz, CDCl$_3$) δ: 154.6 ($^1J_{CF}$=263.5 Hz), 146.6, 137.3, 135.7 ($^2J_{CF}$=24.4 Hz), 135.3 ($^3J_{CF}$=8.4 Hz), 129.6, 129.2, 128.9, 127.6, 126.3, 125.8, 118.4 ($^2J_{CF}$=20.6 Hz) ppm. HRMS (ESI$^+$) for [M+H]$^+$; calculated: 502.10135. found: 502.09963 (error m/z=−3.42 ppm).

1.16 Sulfonyl Azide (SZ17)

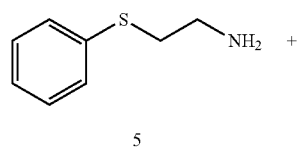

5

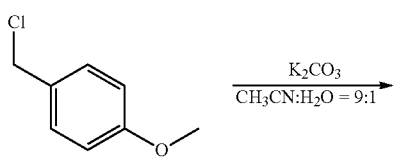

16

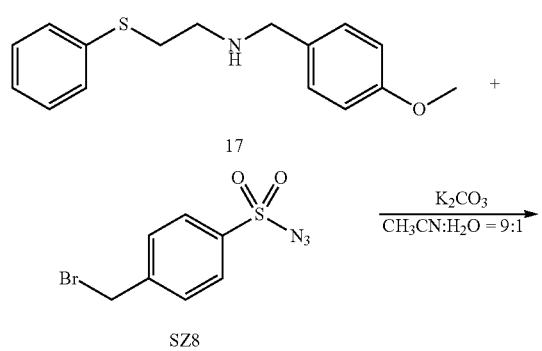

17

(SZ17) was prepared by two steps. First, the mixture of 5 (500 mg, 3.3 mmol), 16 (5.20 mmol) and potassium carbonate (1.0 g, 7.2 mmol) in acetonitrile and water (9:1, mL), was stirred at room temperature for 12 hours. After mixed with ethyl acetate (20 mL) and water (20 mL), the system was extracted by ethyl acetate (20 mL×3). The combined organic phase was dried by anhydrous sodium sulfate and concentrated. Intermediate 17 (330 mg, 37%) was obtained by flash chromatography (hexane:EtOAc=1:1-1:3; Rf=0.2 in hexane:EtOAc=1:1). $^1$H-NMR (400 MHz, CDCl$_3$) δ: 7.37-7.16 (m, 6H), 6.91-6.89 (m, 2H), 6.81 (d, J=8.4 Hz, 1H), 3.7-3.77 (m, 5H), 3.09 (t, J=6.4 Hz, 2H), 2.87 (t, J=6.0 Hz, 2H), 1.72 (s, 1H) ppm. $^{13}$C-NMR (100 MHz, CDCl$_3$) δ: 159.5, 141.6, 135.6, 129.3, 129.1, 128.6, 125.8, 120.1, 113.2, 112.2, 54.8, 53.1, 47.3, 33.9 ppm.

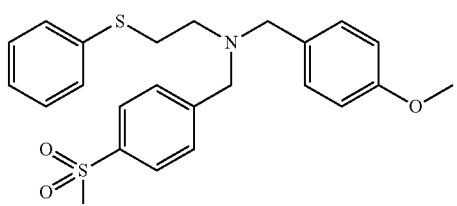

SZ17

(SZ17) was prepared starting from 17 and known (SZ8) using the procedure described for the preparation of (SZ9) in 54% yield. $^1$H-NMR (400 MHz, CDCl$_3$) δ: 7.86 (d, J=8.0 Hz, 2H), 7.60 (d, J=8.0 Hz, 2H), 7.27-7.13 (m, 6H), 6.99-6.95 (m, 2H), 6.81 (dd, J=8.0, 2.0 Hz, 1H), 3.81 (s, 3H), 3.69 (s, 2H), 3.63 (s, 2H), 3.07 (t, J=7.2 Hz, 2H), 2.76 (t, J=7.2 Hz, 2H) ppm. $^{13}$C-NMR (100 MHz, CDCl$_3$) δ: 159.5, 147.6, 140.1, 136.6, 136.0, 129.4, 129.2, 128.7, 128.5, 127.7, 127.2, 125.7, 120.8, 114.2, 112.4, 58.2, 57.5, 54.9, 52.6, 31.1 ppm.

1.17 Thio Acid (TA2)

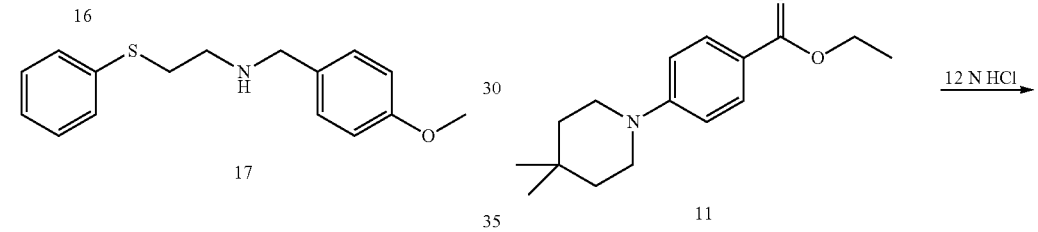

11

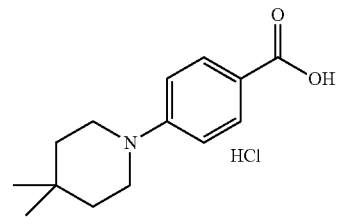

12

A mixture of known 11 (Kobayashi et al., Synthesis 1985, 6-7, 671-2) (6.0 g, 23 mmol) and 12 N HCl (40 mL) was kept at refluxing temperature overnight. The reaction mixture was slowly cooled down and white crystals precipitated. The flask was then cooled to 0° C. for 10 minutes and the mixture was quickly filtrated. The crystals were washed with dichloromethane yielding the known product 12 (4.5 g, 73.2%). $^1$H-NMR (250 MHz, CDCl$_3$) δ: 7.94 (d, J=6.2 Hz, 2H), 7.67 (bs, 2H), 3.43 (bs, 4H), 1.69 (bs, 4H), 1.01 (s, 6H) ppm. HRMS (ESI$^+$) for [M+H]$^+$; calculated: 234.14866. found: 234.14797 (error m/z=−3.79 ppm).

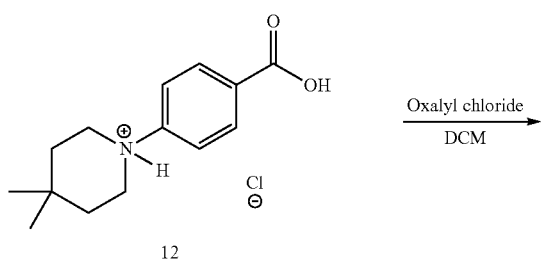

12

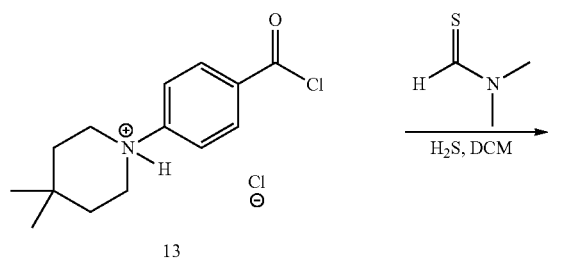

13

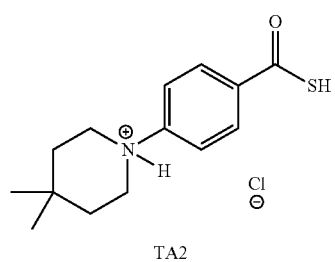

TA2

Oxalyl chloride (740 mg, 0.5 mL, 5.83 mmol) was added dropwise into a solution of 12 (500 mg, 1.86 mmol) in dichloromethane at 0° C. The mixture was then stirred at room temperature for 8 hours. Then, dimethylthioformamide (0.6 mL, 6.7 mmol) was added to the above solution, and hydrogen sulfide was passed through the reaction mixture for 10 minutes at a moderate rate. The course of the reaction was monitored by TLC and once compound 13 completely disappeared, the addition of hydrogen sulfide was stopped. An excess of hexanes was added until a yellow powder precipitated. The powder was collected by filtration and product (TA2) (400 mg, 75% yield) was obtained by quick flash chromatography (DCM:MeOH=30:1). Rf=0.65 (DCM: MeOH=18:1) in the absence of light. $^1$H-NMR (400 MHz, CDCl$_3$) δ: 7.75 (d, J=8.4 Hz, 2H), 6.80 (d, J=8.4 Hz, 2H), 4.32 (bs, 1H), 3.36-3.33 (m, 4H), 1.48-1.45 (m, 4H), 0.98 (s, 6H) ppm. $^{13}$C-NMR (100 MHz, CDCl$_3$) δ: 187.7, 154.6, 130.1, 125.2, 112.7, 43.8, 37.8, 28.6, 27.7 ppm. HRMS (ESI$^+$) for [M+H]$^+$; calculated: 250.12601. found: 250.12593 (error m/z=−0.33 ppm).

1.18 Thio Acid (TA3)

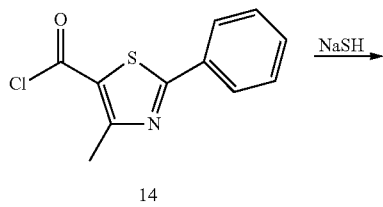

14

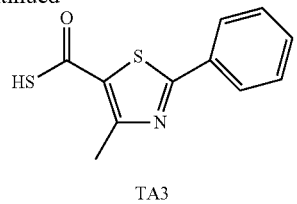

TA3

Compound 14 (300 mg, 1.26 mmol) was added slowly to a saturated solution of sodium hydrogensulfide (211 mg, 3.76 mmol) in water at room temperature. The mixture was stirred at room temperature for 3 hours, ethyl acetate (50 mL) was then added followed by saturated aqueous potassium carbonate solution (50 mL). After extraction by ethyl acetate (50 mL×3), the combined organic phases were dried over anhydrous sodium sulfate and concentrated. The product (TA3) (200 mg, 67%) was obtained by quick flash chromatography (hexanes:EtOAc=1:1). Rf=0.25 in hexane:EtOAc=1:1) in the absence of light. $^1$H-NMR (400 MHz, CD$_3$OD) δ: 6.36 (bs, 2H), 5.90 (bs, 3H), 1.76 (bs, 1H), 1.12 (s, 3H) ppm. $^{13}$C-NMR (100 MHz, CD$_3$OD) δ: 203.6, 168.8, 152.1, 142.4, 134.6, 131.5, 130.1, 127.4, 17.6 ppm. HRMS (ESI$^+$) for [M+H]$^+$; calculated: 236.01983. found: 236.01982 (error m/z=−0.04 ppm).

1.19 Thio Acid (TA4)

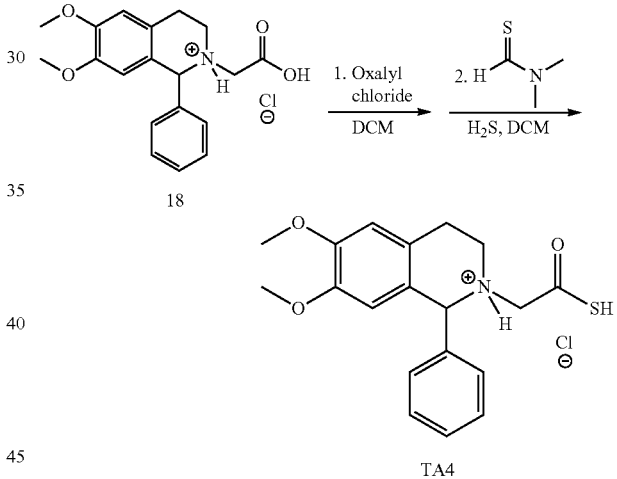

18

TA4

The synthesis of (TA4) was accomplished via the same procedure as described for (TA3). $^1$H-NMR (400 MHz, CDCl$_3$) δ: 7.35-7.15 (m, 5H), 6.66 (s, 1H), 6.25 (s, 1H), 5.53 (s, 1H), 3.85 (s, 3H), 3.81 (bs, 2H), 3.65 (s, 3H), 3.43-3.30 (m, 2H), 3.22-3.00 (m, 2H) ppm. $^{13}$C-NMR (100 MHz, CDCl$_3$) δ: 149.7, 148.8, 136.5, 130.6, 130.1, 129.5, 129.4, 123.6, 111.3, 111.0, 66.3, 63.6, 56.2, 56.0, 45.4, 45.4 ppm. HRMS (ESI$^+$) for [M]$^+$; calculated: 344.13149. found: 344.13149 (error m/z=−0.02 ppm).

1.20 Thio Acid (TA5)

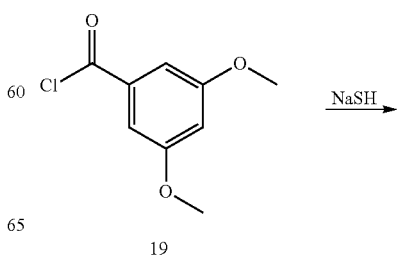

19

-continued

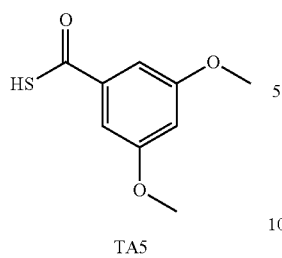

TA5

The synthesis of (TA5) was accomplished via the same procedure as described for (TA2). $^1$H-NMR (400 MHz, CDCl$_3$) δ: 7.08 (s, 1H), 7.07 (s, 1H), 6.72 (s, 1H), 3.88 (s, 3H), 3.88 (s, 3H) ppm. $^{13}$C-NMR (100 MHz, CDCl$_3$) δ: 190.0, 160.7, 138.4, 106.1, 105.6, 55.5 ppm. HRMS (ESI$^+$) for [M]$^+$; calculated: 344.13149. found: 344.13149 (error m/z=−0.02 ppm).

1.21 Thio Acid (TA6)

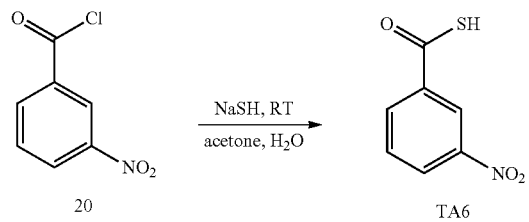

To a solution of NaSH (90 mg, 1.6 mmol) in water (1 ml) was added dropwise a solution of acid chloride in acetone (6 ml). The resulting mixture was stirred for 3 h. The solvent was removed under reduced pressure and resulting crude was basified using 10% NaOH solution (pH=12). The solution was slowly acidified using 2N HCl solution (pH=1). Corresponding thio acid (TA6) crashed out and was filtered, washed with deionized water and dried under vacuum to obtain pale yellow crystals of (TA6). $^1$H-NMR (400 MHz, CDCl$_3$) δ: 8.72-8.71 (m, 1H), 8.46-8.43 (m, 1H), 8.2 (d, J=7.6 Hz, 1H), 7.68 (t, J=8 Hz, 1H) ppm. $^{13}$C-NMR (100 MHz, CDCl$_3$) δ: 188.2, 137.9, 133.4, 130.3, 128.3, 122.9 ppm.

1.22 Thio Acid (TA7)

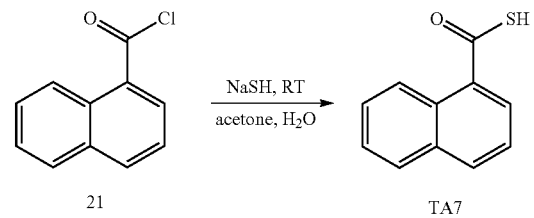

The synthesis of (TA7) was accomplished via the same procedure as described for (TA6). $^1$H-NMR (400 MHz, CDCl$_3$) δ: 8.59-8.52 (m, 1H), 8.34 (d, J=7.2 Hz, 1H), 8.08 (m, 1H), 7.88 (m, 1H), 7.57 (m, 3H) ppm. $^{13}$C-NMR (100 MHz, CDCl$_3$) δ: 188.1, 134.3, 133.4, 129.5, 129.0, 128.8, 128.65, 127.3, 127.0, 125.4, 124.7 ppm.

EXAMPLE 2

Reaction/Incubation Procedures and LC/MS Measurements

2.1 General Procedure for Incubations of Bcl-X$_L$ with Reactive Fragments

In a 96-well plate, one thio acid building block (1 μL of a 2 mM solution in methanol) and one sulfonyl azide building block (1 μL of a 2 mM solution in methanol) were added to a solution of Bcl-X$_L$ (98 μL of a 2 μM Bcl-X$_L$ solution in buffer (58 mM Na$_2$HPO$_4$, 17 mM NaH$_2$PO$_4$, 68 mM NaCl, 1 mM NaN$_3$, pH=7.40)). The 96-well plate was sealed and incubated at 38.5° C. for six hours. The incubation samples were then subjected to liquid chromatography combined with mass spectrometry analysis in the selected ion mode (LC-MS-SIM, Zorbax SB-C18 preceded by a Phenomenex C18 guard column, electrospray ionization and mass spectroscopic detection in the positive selected ion mode, tuned to the expected molecular mass of the product). The TGS hit compound was identified by the mass and retention time. As a control, identical building block combinations were incubated in buffer without Bcl-X$_L$ and subjected to LC/MS-SIM analysis. Comparison of the LC-MS-SIM chromatograms of these control incubations with the chromatograms of the Bcl-X$_L$ containing incubations allows to determine whether the protein is templating the corresponding amidation reactions or not. For the Bcl-X$_L$ containing incubation sample showing acylsulfonamide formation, a second control has been undertaken. Synthetically prepared acylsulfonamide was subjected to LC/MS-SIM analysis and the retention time was compared with the retention time identified in the Bcl-X$_L$ containing incubation.

The gradient used for LC/MS-SIM is shown below:

| Time | B * | Flowrate |
| --- | --- | --- |
| 0 | 10% | 0.7 mL/min |
| 4 | 20% | 0.7 mL/min |
| 12 | 100% | 0.7 mL/min |
| 13 | 100% | 0.7 mL/min |
| 13.01 | 100% | 1.5 mL/min |
| 15.00 | 100% | 1.5 mL/min |
| 15.50 | 20% | 1.5 mL/min |
| 16.50 | 20% | 1.0 mL/min |
| 16.51 | 20% | 0 mL/min |

* eluant A: H$_2$O (0.05% TFA); eluant B: CH$_3$CN 0.05% TFA)

2.2 Incubations at Various Bcl-X$_L$ Concentrations

Different concentrations of Bcl-X$_L$ were explored to determine the ideal protein concentrations for the incubations with building blocks (SZ4) and (TA2). The minimal protein concentration for obtaining a good ratio between templated and non-templated reactions is 2 μM. Incubations at higher concentrations give only slightly better ratios between templated and non-templated reactions. Hence, we determined 2 μM Bcl-X$_L$ to be the most economical with regard to the protein consumption.

Figure 4:
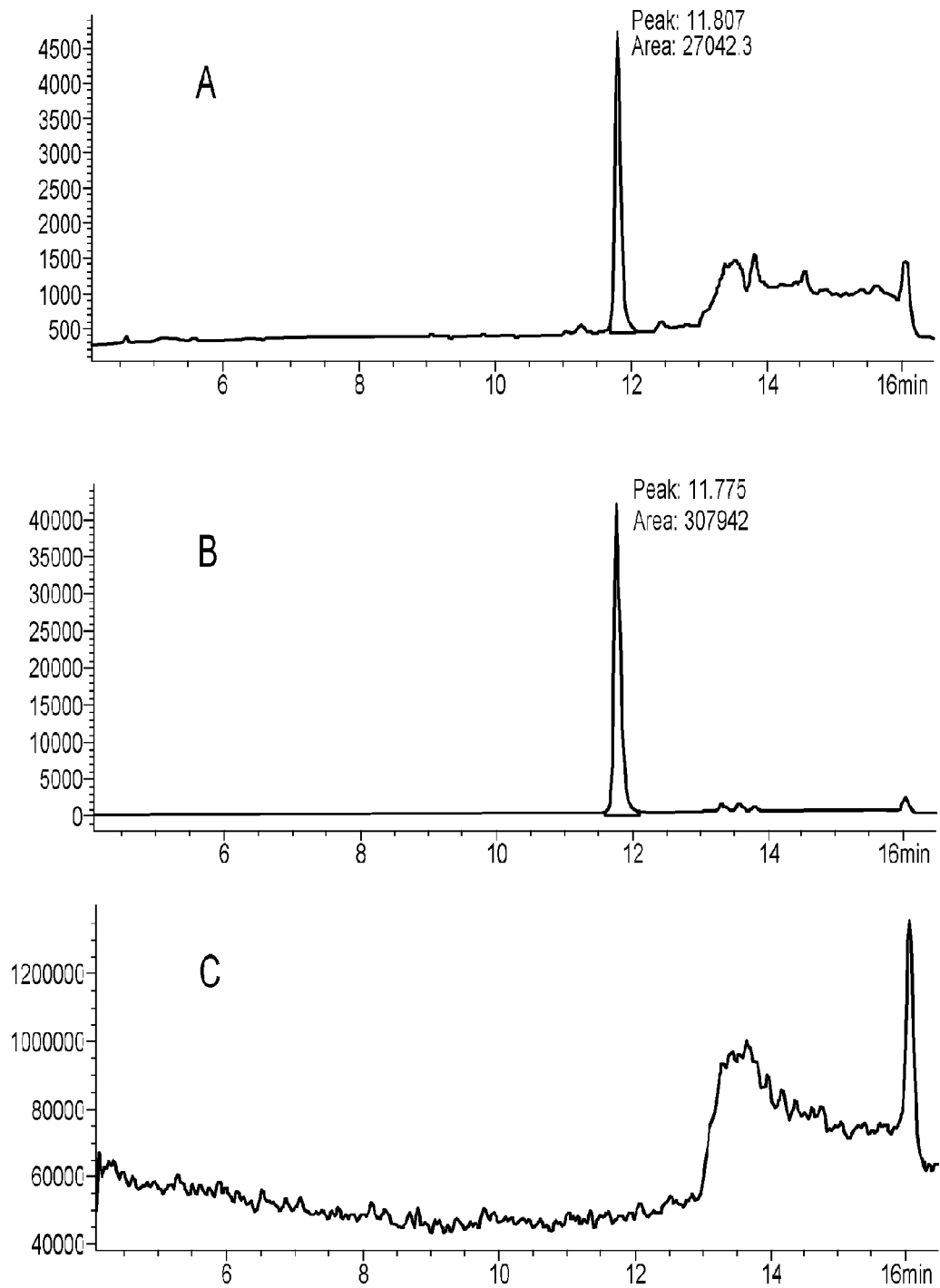
FIG. 4 is an LC/MS trace illustrating the comparison between incubations of (SZ4 and TA2) measured by LC/MS-SIM Mode and LC/MS-Scan Mode. A) Incubation of (SZ4) and (TA2) without Bcl-X$_L$ measured by LC/MS-SIM mode; B) Incubation of (SZ4) and (TA2) with 2 μM Bcl-X$_L$ measured by LC/MS-SIM mode; C) Incubation of (SZ4) and (TA2) with 2 μM Bcl-X$_L$ measured by LC/MS-Scan mode.

2.3 Comparison Between Incubations of SZ4 and TA2 Measured by the LC/MS-SIM and the LC/MS-Scan Mode The sensitivity of the LC/MS can be significantly increased by utilizing the MS instrument in the selected ion monitoring (LC/MS-SIM). The advantage of LC/MS-SIM over LC/MS-Scan for kinetic TGS has been previously reported (Manetsch et al., *J. Am. Chem. Soc.* 2004; 126, 12809-12818). See FIG. 4.

Figure 5:
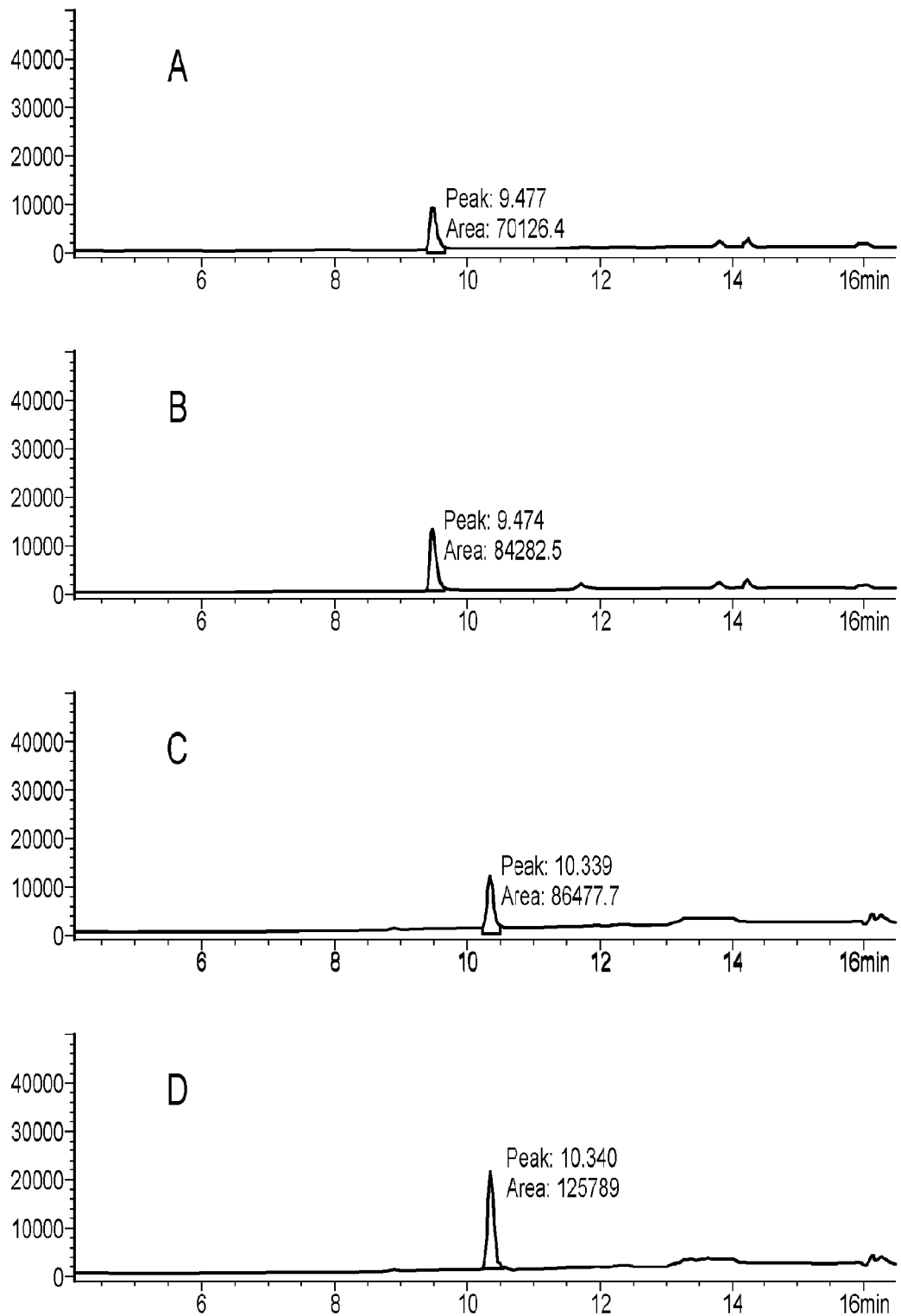
FIG. 5 is an LC/MS trace illustrating the incubations of (SZ1) and (TA2) and incubations of (SZ2) and (TA2). A) Incubation of (SZ1) and (TA2) without Bcl-X$_L$; B) Incubation of (SZ1) and (TA2) with 2 μM Bcl-X$_L$; C) Incubation of (SZ5) and (TA2) without Bcl-X$_L$; D) Incubation of (SZ5) and (TA2) with 2 μM Bcl-X$_L$.
Figure 6:
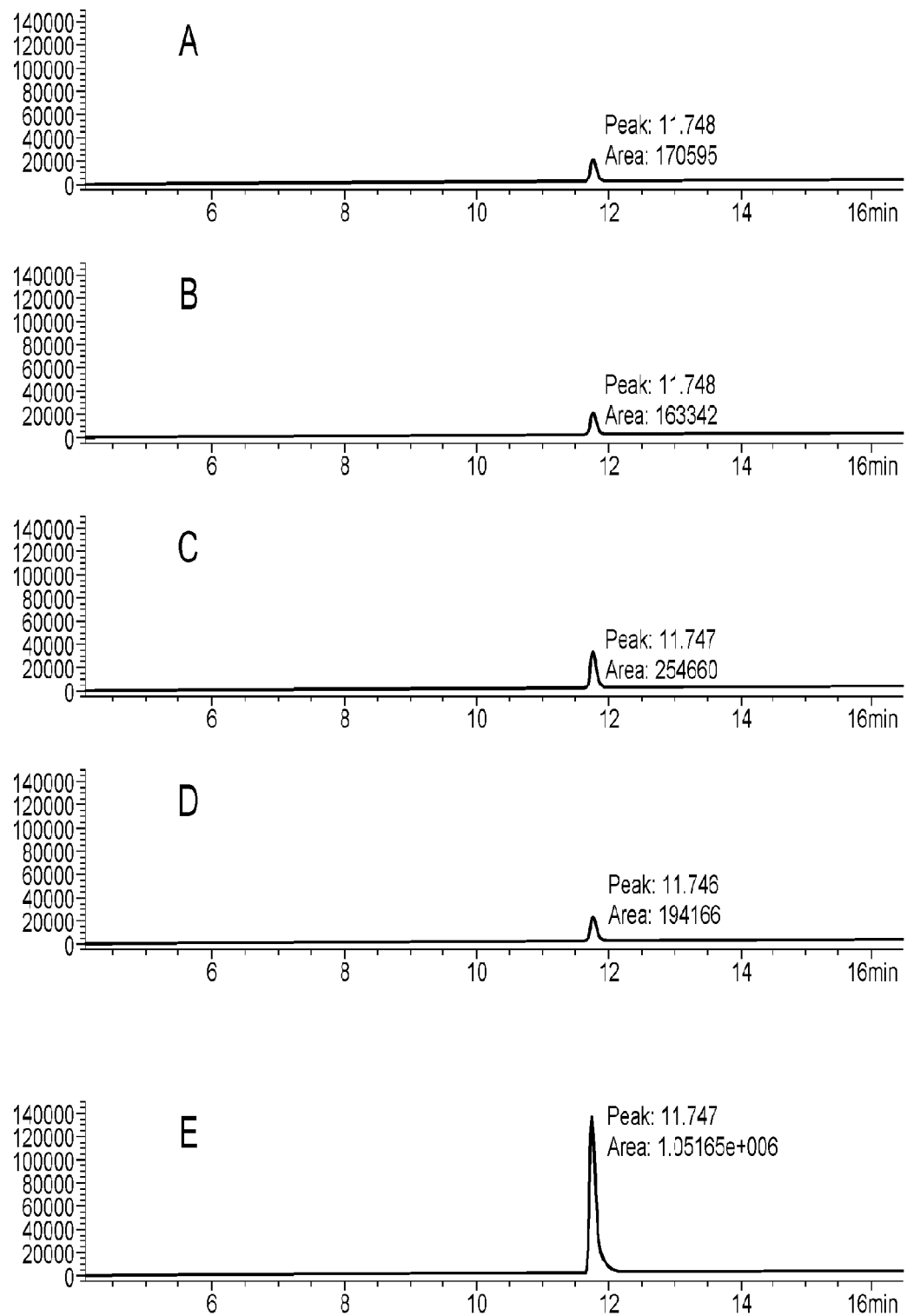
FIG. 6 is an LC/MS trace illustrating the incubations of (SZ4) and (TA2) with bovine erythrocyte carbonic anhydrase II, concanavalin A and mAChE. A) Incubation of (SZ4) and (TA2) without proteins; B) Incubation of (SZ4) and (TA2) with 2 μM of bCAII; C) Incubation of (SZ4) and (TA2) with 2 μM of ConA. D) Incubation of (SZ4) and (TA2) with 2 μM of mAChE. E) Incubation of (SZ4) and (TA2) with 2 μM of Bcl-X$_L$.
Figure 8:
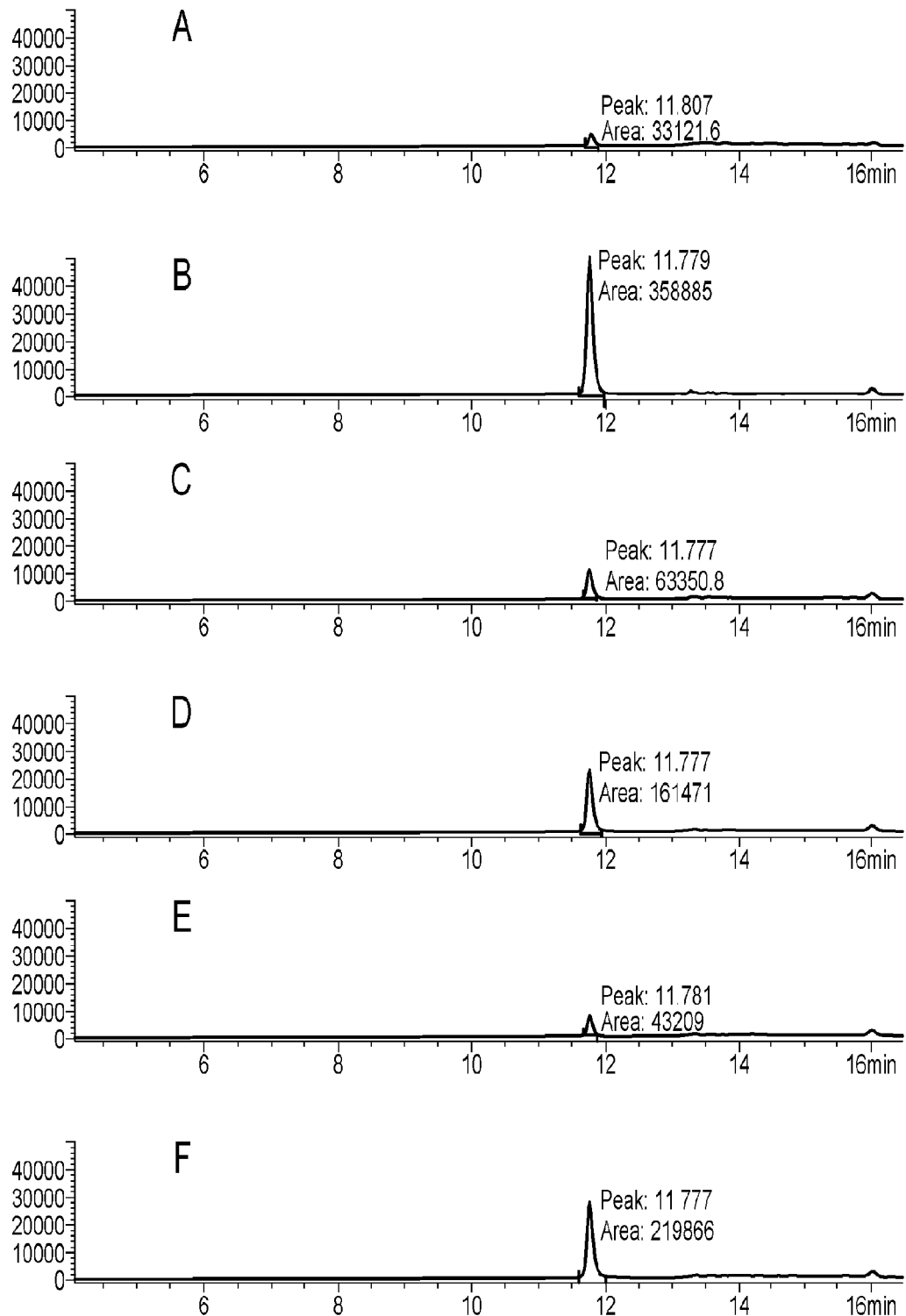
FIG. 8 is an LC/MS trace illustrating Bcl-X$_L$-templated incubations containing Bim, mutant Bim and mutant Bak. A) Incubation of (SZ4) and (TA2) without Bcl-X$_L$; B) Incubation of (SZ4) and (TA2) with 2 μM Bcl-X$_L$; C) Incubation of (SZ4) and (TA2) with 2 μM Bcl-X$_L$ and 20 μM Bak BH3 peptide; D) Incubation of (SZ4) and (TA2) with 2 μM Bcl-X$_L$ and 20 μM of mutant Bak; E) Incubation of (SZ4) and (TA2) with 2 μM Bcl-X$_L$ and 20 μM of Bim; F) Incubation of (SZ4) and (TA2) with 2 μM Bcl-X$_L$ and 20 μM of mutant Bim.
Figure 9:
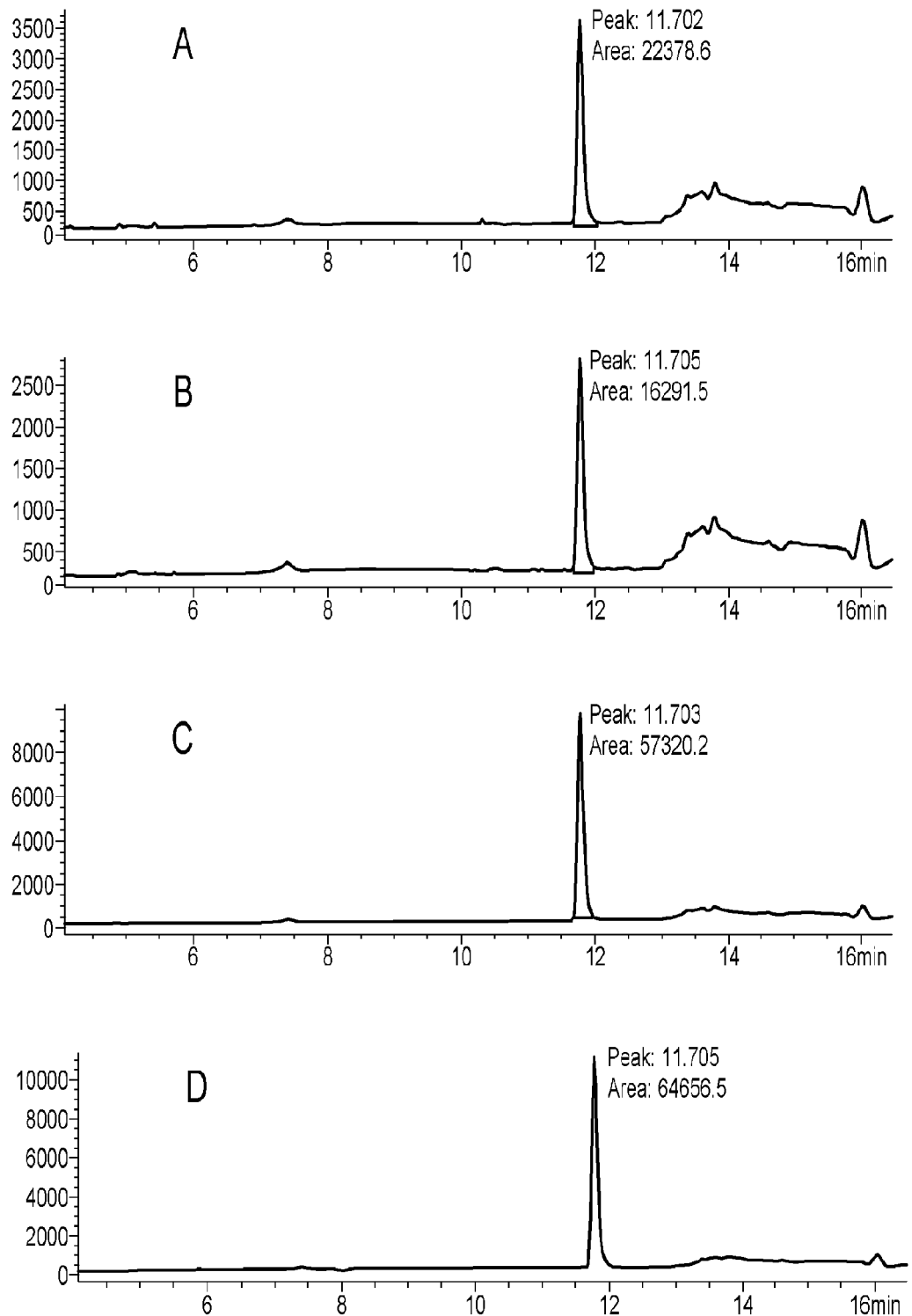
FIG. 9 is an LC/MS trace illustrating incubations of (SZ4) and (TA2) with Bim, mutant Bim and mutant Bak (no Bcl-X$_L$). A) Incubation of (SZ4) and (TA2) without peptides; B) Incubation of (SZ4) and (TA2) with 20 μM Bim; C) Incubation of (SZ4) and (TA2) with 20 μM of mutant Bim; D) Incubation of (SZ4) and (TA2) with 20 μM of mutant Bak.

2.4 TGS Screening Criteria and Two Examples of TGS Incubation Samples Failing at Templating the Formation of Acylsulfonamides Examples of incubation samples failing at templating the formation of acylsulfonamides are depicted in FIG. 5. To determine whether a building block combination is a TGS hit or not, the ratio between the peak areas of the $Bcl-X_L$-templated reaction over the peak area of the incubation without $Bcl-X_L$ is calculated. If this ratio is greater than 4, we consider this particular combination to be a TGS hit combination. Further control incubation experiments (see FIG. 1 in the communication, FIG. 6, FIG. 8, FIG. 9, and FIG. 10) are performed to fully validate this particular TGS hit.

2.5 Incubations of (SZ4) and (TA2) with Bovine Erythrocyte Carbonic Anhydrase II, Concanavalin A and Mouse Acetylcholinesterase.

The building blocks (SZ4) and (TA2) were incubated with proteins (20M) bovine erythrocyte carbonic anhydrase II (bCAII), concanavalin A (ConA) and mouse acetylcholinesterase (mAChE) respectively to test whether these proteins can also template the formation of acylsulfonamide (SZ4TA2). Incubations at 37° C. for 24 hours failed at yielding pronounced amounts of (SZ4TA2).

2.6 Suppressing $Bcl-X_L$-Templated Incubations with Bak BH3 Peptide

Figure 10:
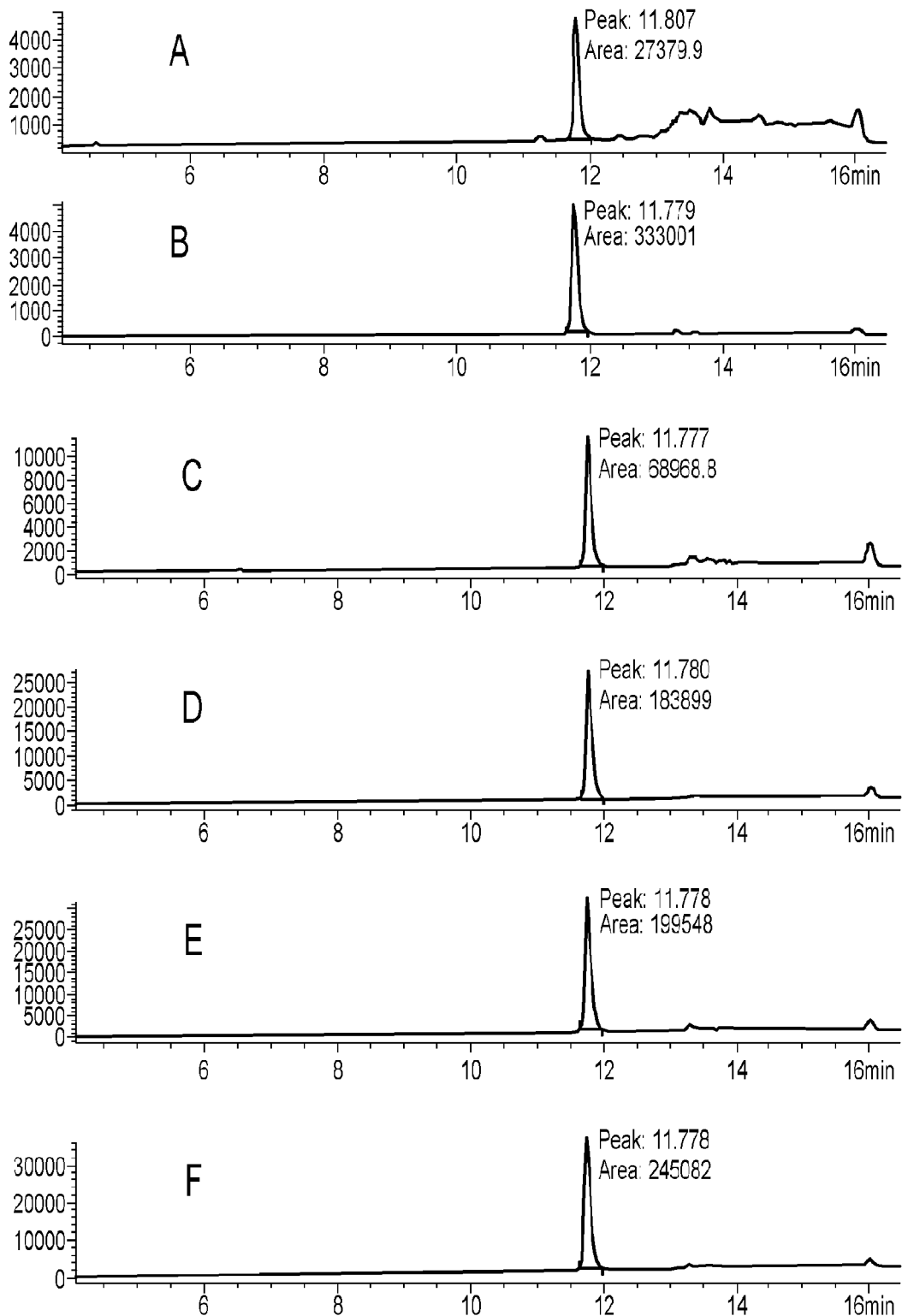
FIG. 10 is an LC/MS trace illustrating the suppression of Bcl-X$_L$-templated incubations with Bak BH3 Peptide. Incubation samples were kept for six hours at 37° C. A) Incubation of (SZ4) and (TA2) without Bcl-X$_L$; B) Incubation of (SZ4) and (TA2) with 2 μM Bcl-X$_L$; C) Incubation of (SZ4) and (TA2) with 2 μM Bcl-X$_L$ and 20 μM Bak BH3 peptide; D) Incubation of (SZ4) and (TA2) with 2 μM Bcl-X$_L$ and 10 μM Bak BH3 peptide; E) Incubation of (SZ4) and (TA2) with 2 μM Bcl-X$_L$ and 5 μM Bak BH3 peptide; F) Incubation of (SZ4) and (TA2) with 2 μM Bcl-X$_L$ and 2 μM Bak BH3 peptide.

Additional control experiments have been performed to test whether the $Bcl-X_L$-templated reaction occurs at the BH3 binding site on $Bcl-X_L$. Reactive building blocks (SZ4) and (TA2) were incubated with $Bcl-X_L$ and pro-apoptotic Bak BH3 peptide. Bak is one of the natural $Bcl-X_L$ ligands and theoretically competes with the reactive building blocks for binding on $Bcl-X_L$ during the incubations. The influence of Bak BH3 peptide on the $Bcl-X_L$-templated reaction was studied at different ratios of Bak BH3 peptide and $Bcl-X_L$ (FIG. 10). At 20 μM Bak BH3 peptide, the templated reaction is significantly suppressed compared to the $Bcl-X_L$ incubation without Bak BH3.

As an additional control experiment, the incubation of (SZ4) and (TA2) with Bak BH3 peptide was carried out for 24 hours (FIG. 7) demonstrating that Bak BH3 can not template the formation of (SZ4TA2).

The sequence of the herein utilized Bak BH3 peptide is the following:

```
BakBH3 (wt):      CMGQVGRQLAIIGDDINRRYDS
```

2.7 Suppressing $Bcl-X_L$-Templated Incubations with Bim, Mutant Bim and Mutant Bak.

Additional control experiments have been performed with Bim, mutant Bim, and mutant Bak. Mutant Bim and mutant Bak are known to bind with lower affinity towards $Bcl-X_L$ compared to wildtype Bak BH3 and Bim peptides. Therefore, the $Bcl-X_L$ incubations containing mutant Bak BH3 and mutant Bim display an increased amount of acylsulfonamide (SZ4TA2) compared to the $Bcl-X_L$ incubations containing wild type Bak BH3 and Bim peptides. The sequences of the various peptides are shown below:

```
BakBH3 (wt):      CMGQVGRQLAIIGDDINRRYDS
                  (see FIG. 7 and FIG. 10)

BakBH3 (mt):      CMGQVGRQAAIIGADINRRYDS

BimBH3 (wt):      CEIWIAQELRRIGDEFNAYYAR

BimBH3 (mt):      CEIWIAQEARRIGAEFNAYYAR
```

2.8 $Bcl-X_L$ Incubations Containing More than Two Reactive Building Blocks.

Figure 11:
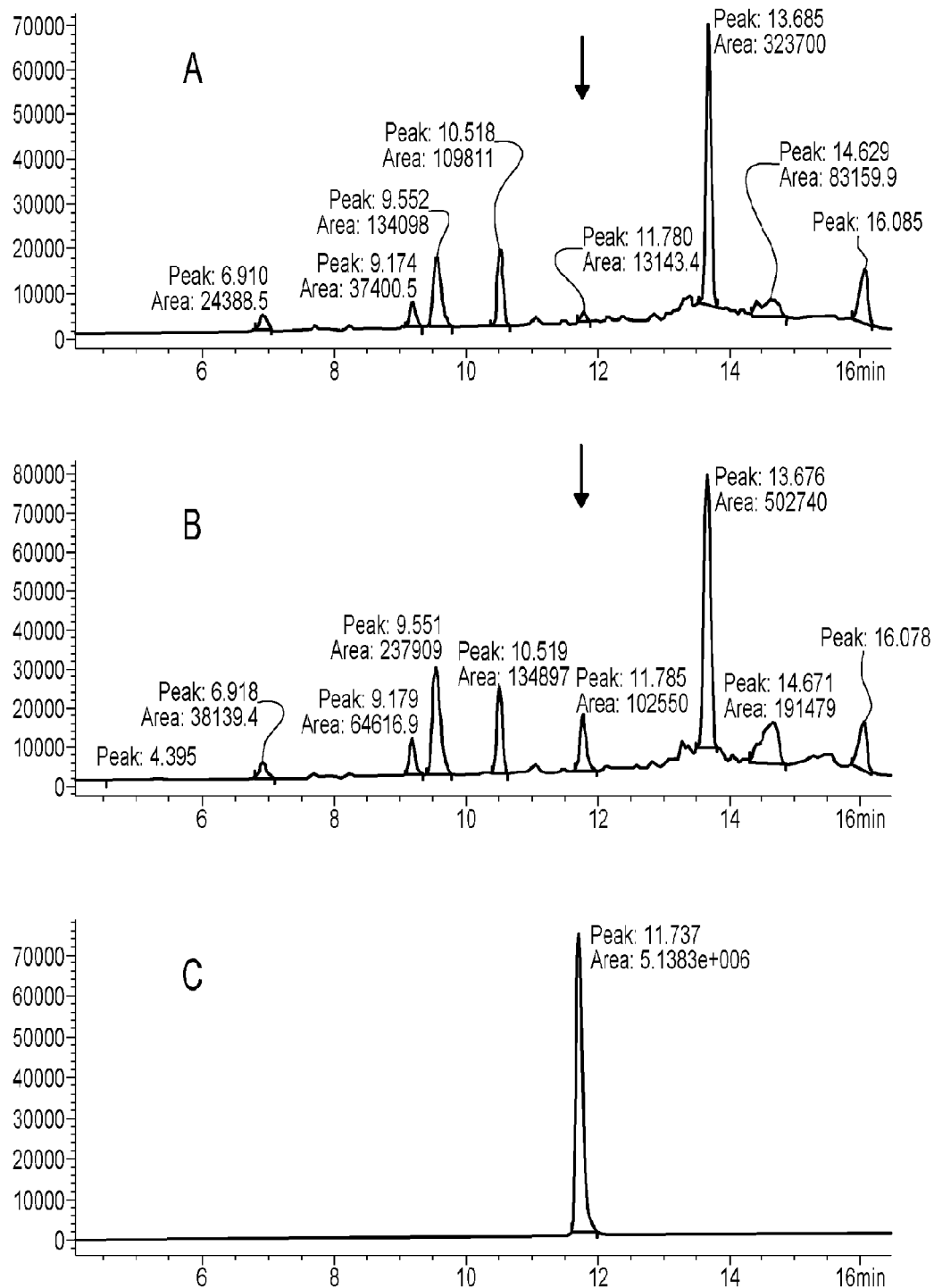
FIG. 11 is an LC/MS trace illustrating Bcl-X$_L$ incubations containing sulfonylazides (SZ1)-(SZ6) and thioacid (TA2). A) Incubation of (SZ1)-(SZ6) and (TA2) without Bcl-X$_L$; B) Incubation of (SZ1)-(SZ6) and (TA2) with 404 Bcl-X$_L$; C) Synthesized compound (SZ4TA2) as reference.
Figure 12:
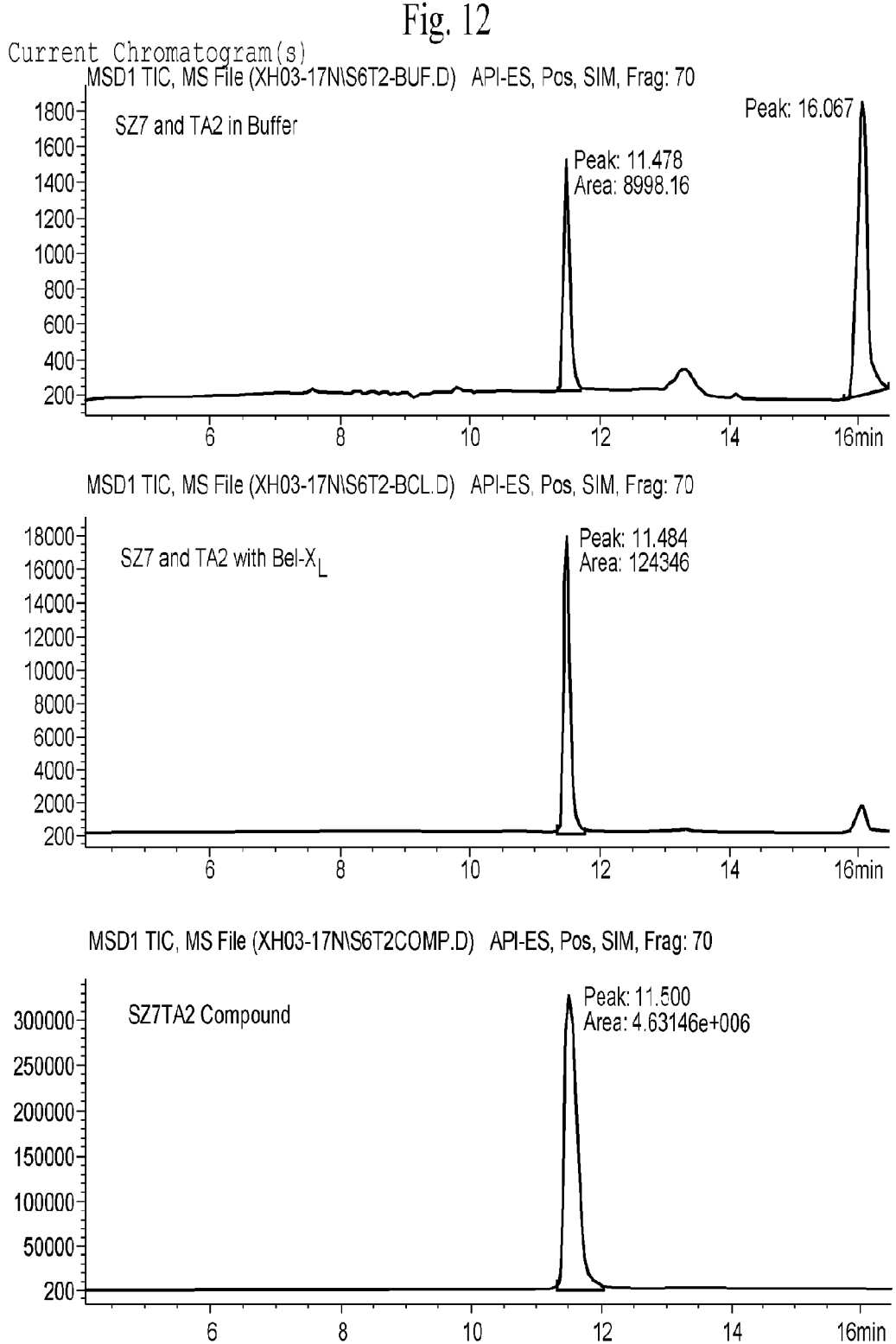
FIGS. 12-19 are LC/MS trace illustrating other sulfonyl azide and thioacid combinations: (SZ7) and (TA2) (FIG. 12); (SZ9) and (TA5) (FIG. 13); (SZ10) and (TA2) (FIG. 14); (SZ15) and (TA3) (FIG. 15); (SZ15) and (TA8) (FIG. 16); (SZ16) and (TA4) (FIG. 17); (SZ16) and (TA8) (FIG. 18); and (SZ17) and (TA7).
Figure 13:
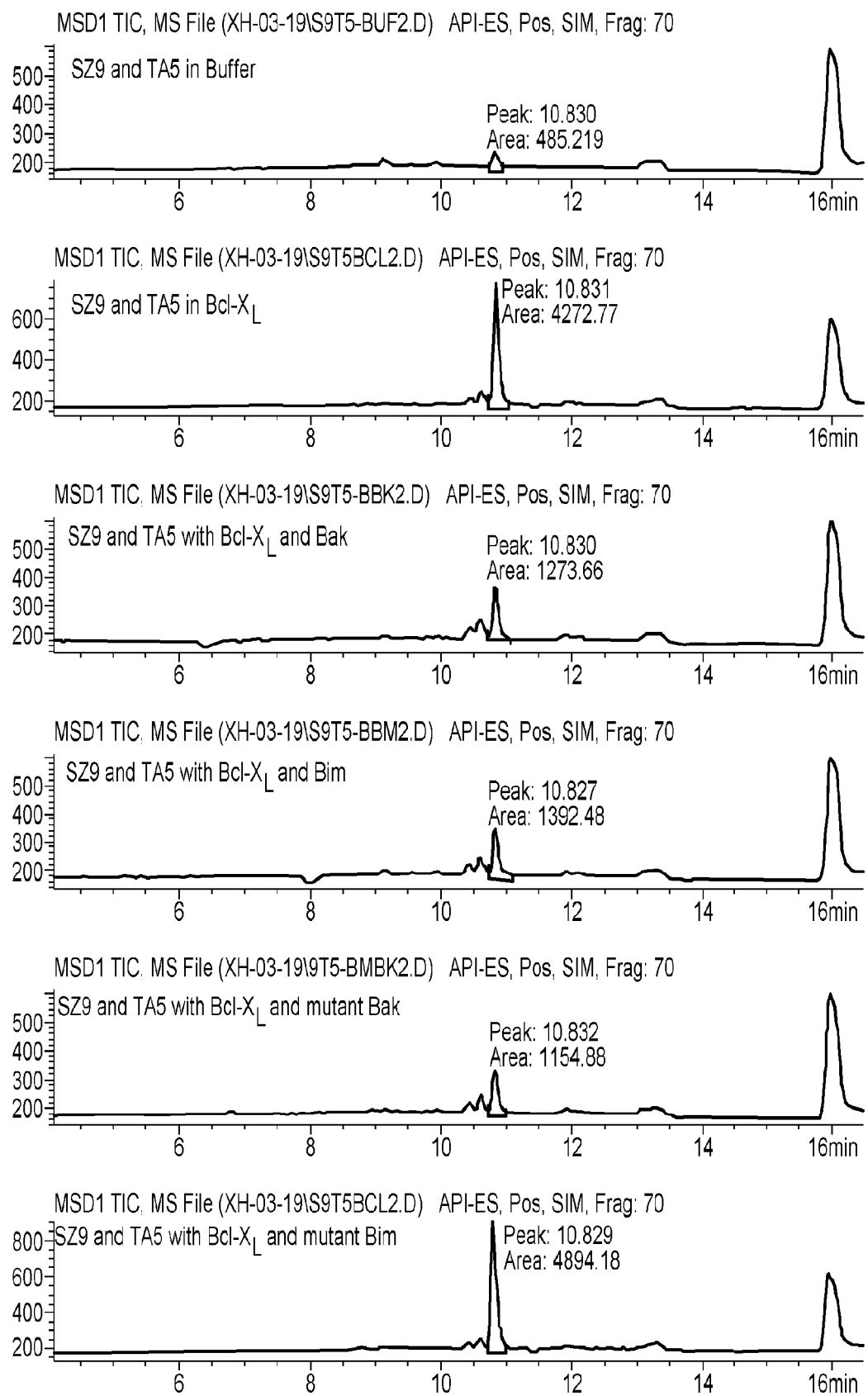
Figure 14:
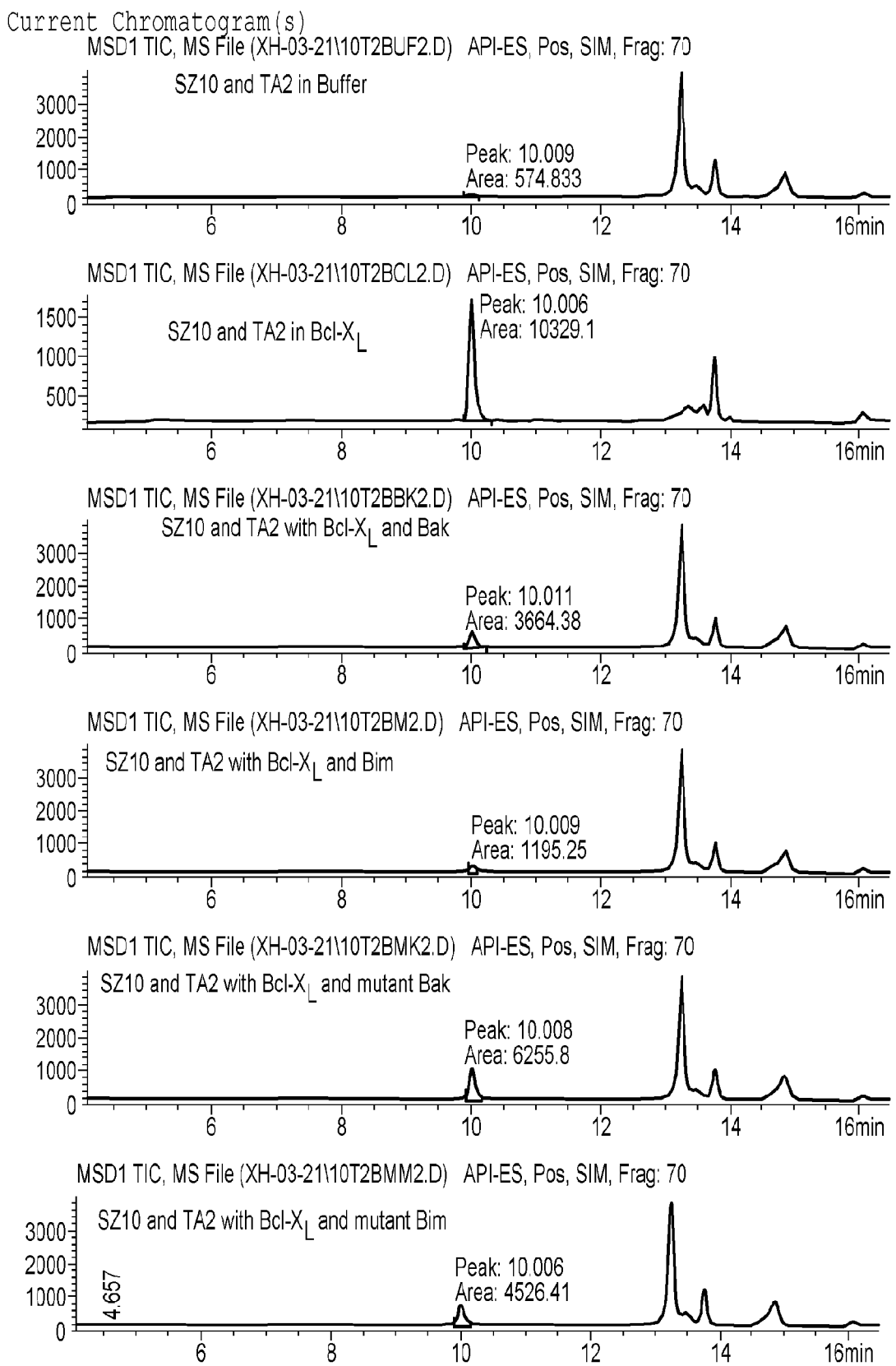
Figure 15:
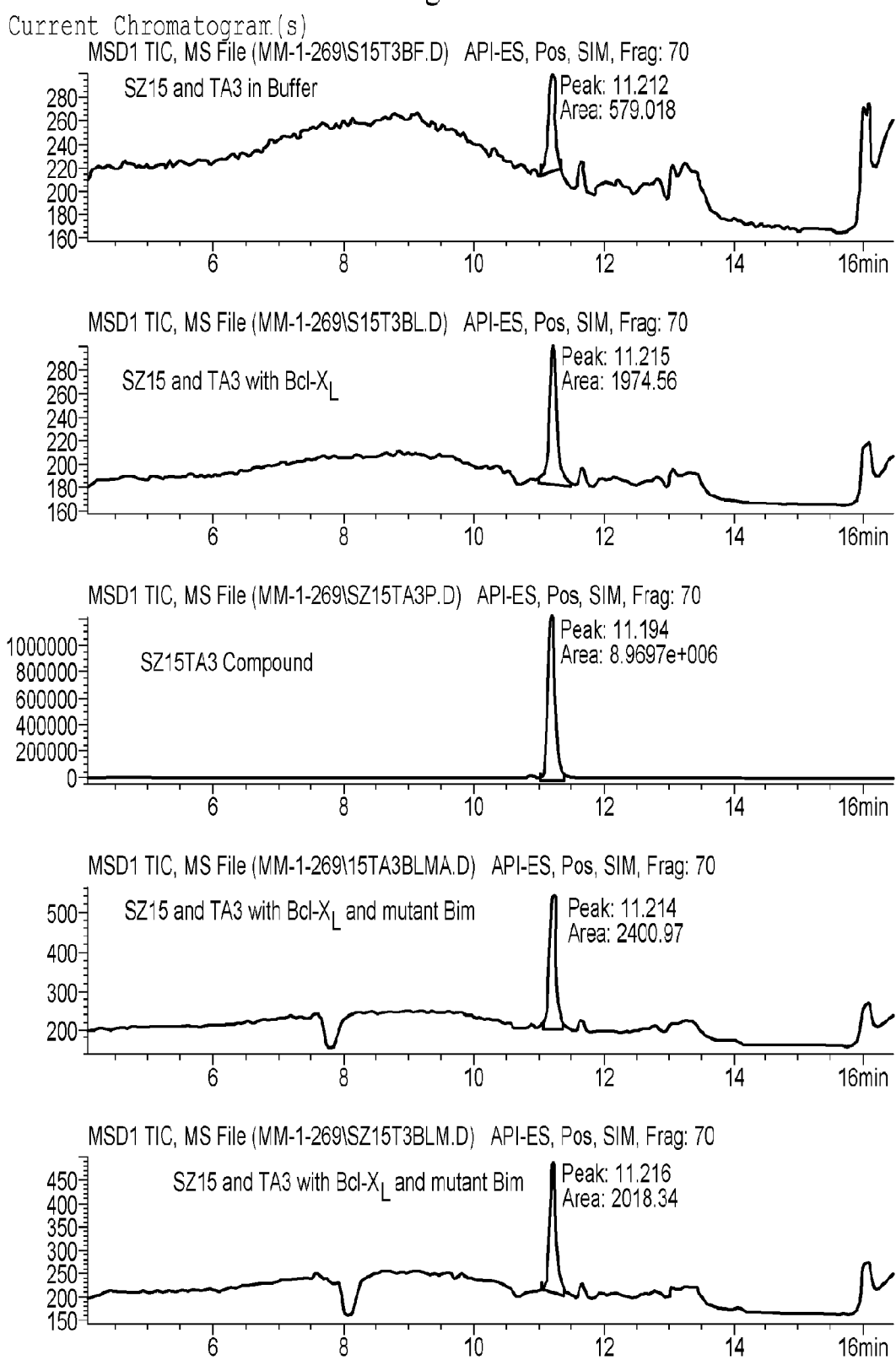
Figure 16:
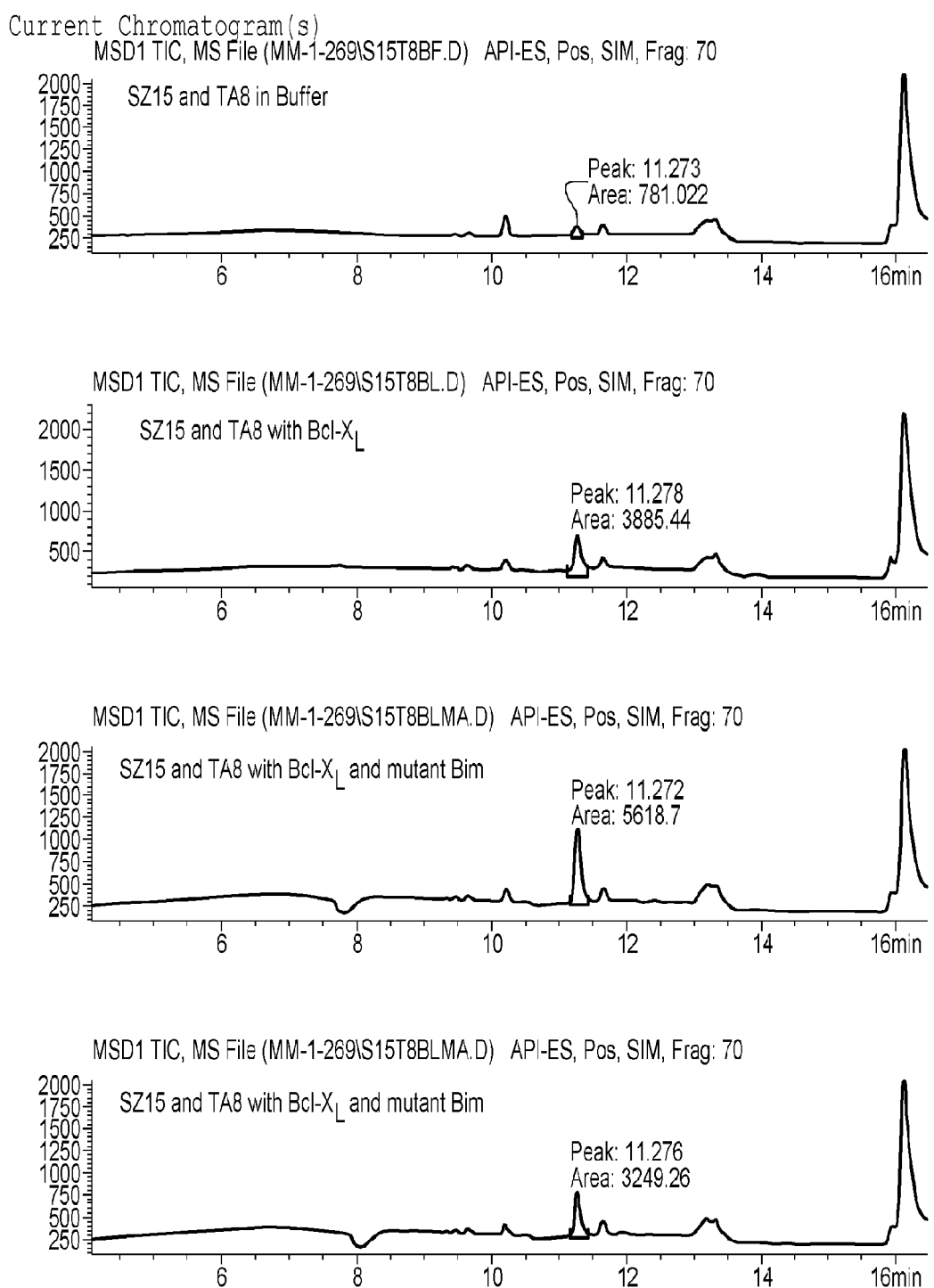
Figure 17:
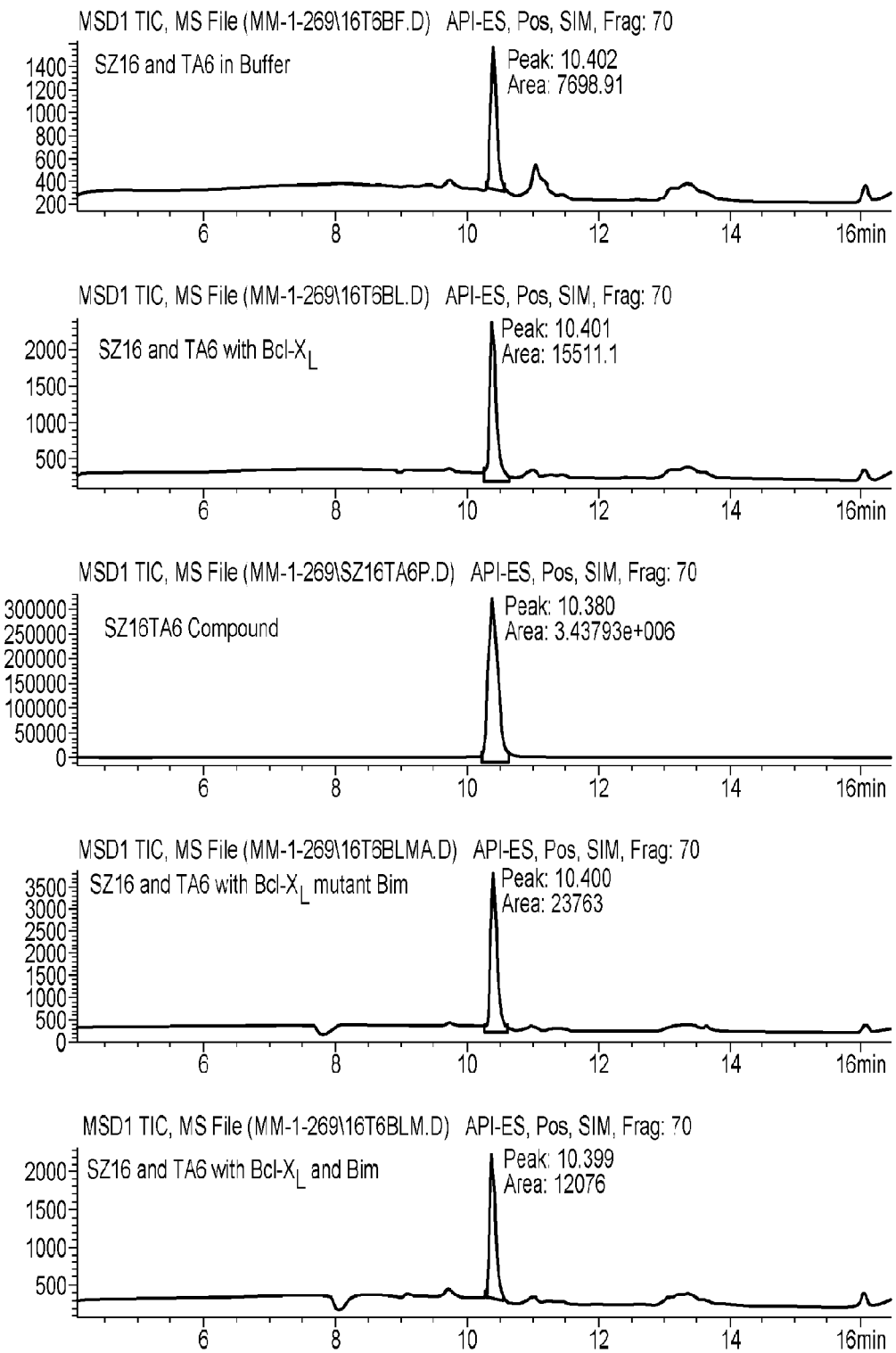
Figure 18:
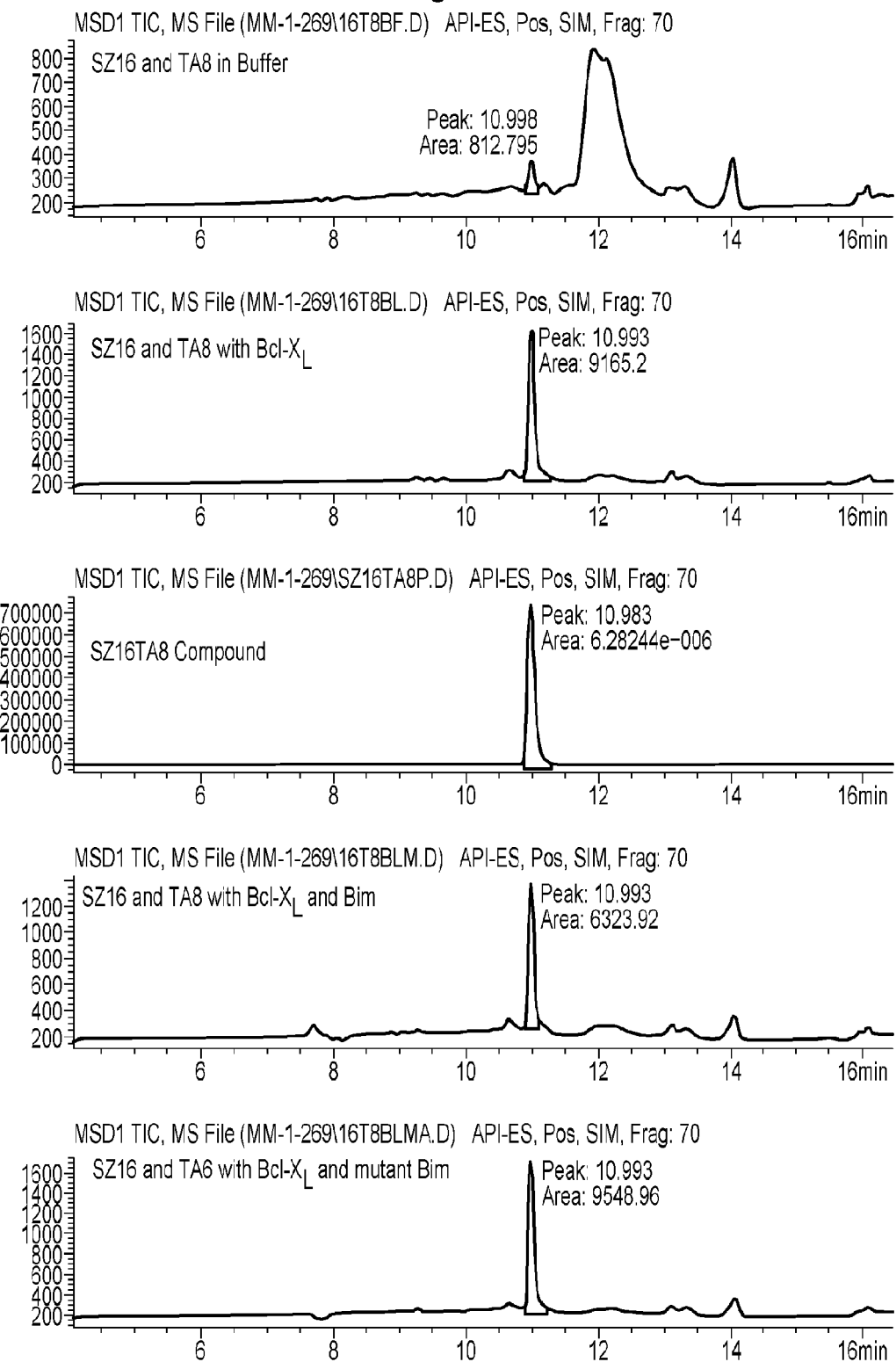
Figure 19:
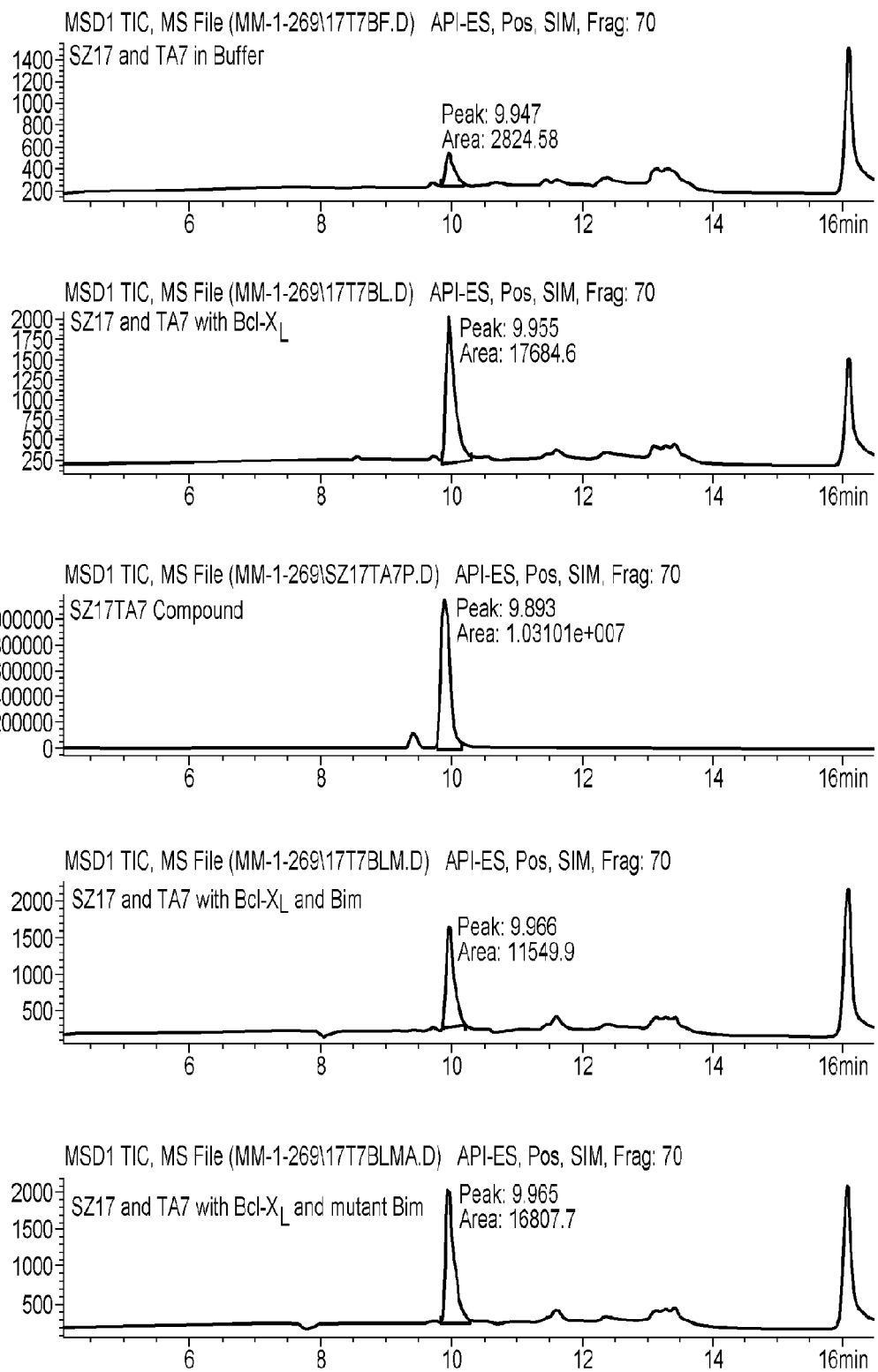

Initial experiments have been performed to investigate whether our TGS screening via the amidation reaction can be performed with incubations containing more than two complimentary reactive building blocks. Previously, this has been shown to be applicable for standard in situ ligation chemistry approaches (Manetsch et al., supra; Krasinski et al., J. Am. Chem. Soc. 2005, 127, 6686-6692). Our study revealed that the incubation sample containing 1 thioacid and 6 sulfonylazides (FIG. 11 with (TA2), (SZ1)-(SZ6)) can give the same results as multiple incubations containing only two complimentary reacting building blocks. Attempts to run an incubation containing simultaneously 3 thioacids (TA1)-(TA3) and 6 azides (SZ1)-(SZ6) failed with 2 μM as well as 10 μM $Bcl-X_L$ concentrations.

Other positive incubations and their LC/MS-SIM measurements can be seen in the Figures. The concentration of active building blocks, proteins and peptides are same as described above. The incubation reaction details are also as same as above. See FIGS. 12-19.

IC50 values for selected acylsulfonamides:

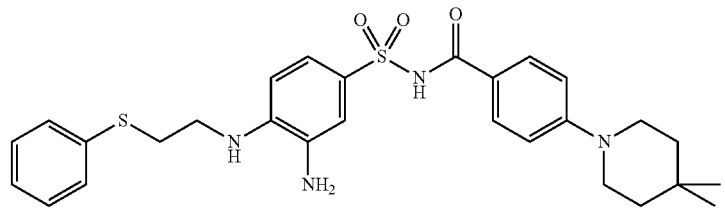

SZ4TA2: $IC_{50}$ = 584 nM

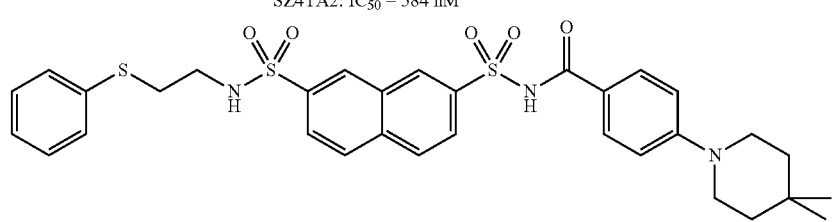

SZ6TA2: $IC_{50}$ = 799 nM

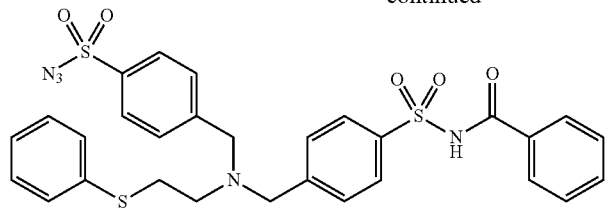
SZ9TA1: IC$_{50}$ = 1.05 µM
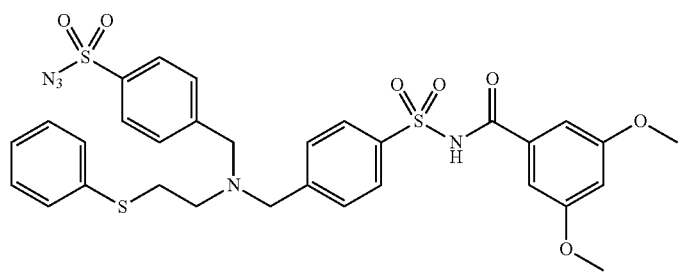
SZ8TA5: IC$_{50}$ = 371 nM
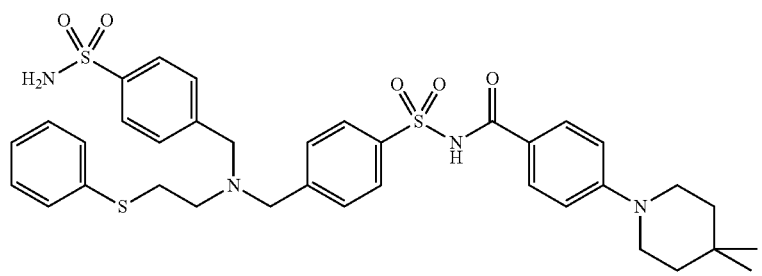
SZ10TA2
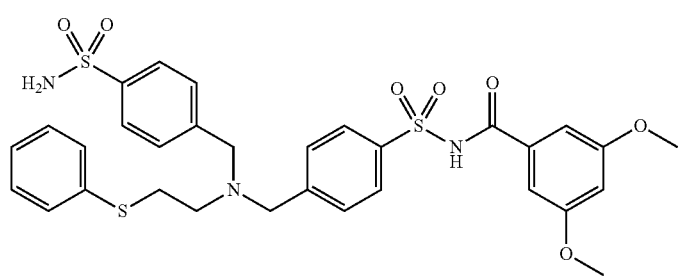
SZ10TA5

EXAMPLE 3

Synthesis of a Cylsulfonamides 3.1 Acylsulfonamide (SZ7TA2) 131.2, 130.9, 130.2, 130.0, 129.5, 129.4, 129.0, 126.9, 126.2, 125.4, 117.9, 113.0, 43.7, 41.7, 37.8, 33.9, 28.6, 27.7 ppm. HRMS (ESI$^+$) for [M+H]$^+$; calculated: 638.18116. found: 638.18097 (error m/z=−0.29 ppm).

3.2 Acylsulfonamide (SZ9TA5)

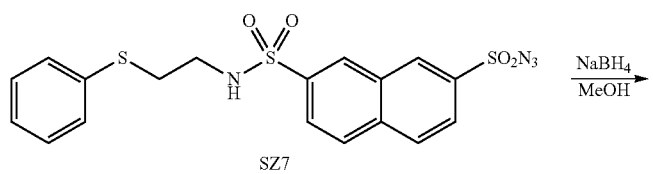

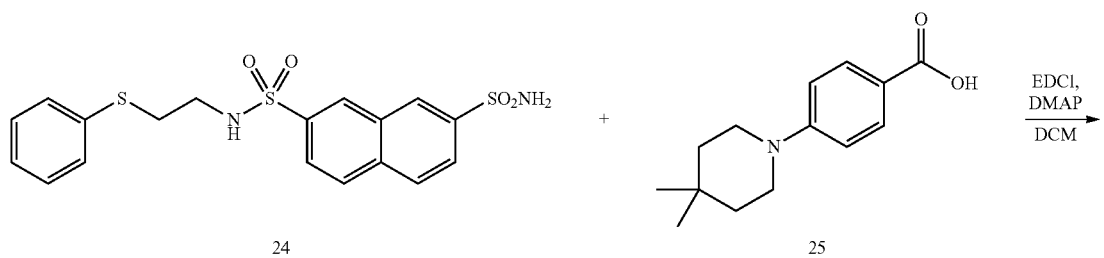

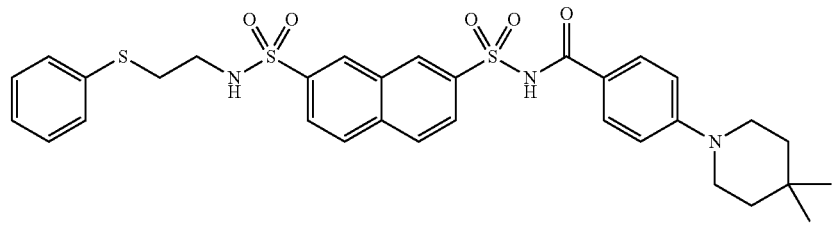

Sodium boron hydride (60 mg, 1.5 mmol) was added slowly to the solution of (SZ7) (450 mg, 1 mmol) in Methanol. The system was stirred for 30 min and removed all the solvent. Intermediate 24 was obtained by flash chromatography and used for next step directly. The solution of 24, 25 (1 mmol), EDCI (2 mmol) and DMAP (0.2 mmol) in DCM was stirred for 12 hours at room temperature, and the system was extracted by ethyl acetate (20 mL×3). The combined organic phase was dried by anhydrous sodium sulfate and concentrated. And product (SZ7TA2) (102 mg, 16%) was obtained by flash chromatography (hexane:EtOAc=1:1; Rf=0.2 in hexane:EtOAc=1:1). $^1$H-NMR (400 MHz, CDCl$_3$) δ: 8.74 (s, 1H), 8.43 (s, 1H), 8.24 (d, J=8.8 Hz, 1H), 7.95-7.89 (m, 3H), 7.67 (d, J=8.4 Hz, 2H), 7.14 (d, J=6.4 Hz, 2H), 7.07 (d, J=6.8 Hz, 2H), 6.72 (d, J=8.8 Hz, 2H), 5.46 (d, J=65.2 Hz, 1H), 3.26-3.25 (m, 4H), 3.13 (d, J=6.0 Hz, 2H), 2.96 (d, J=6.4 Hz, 2H), 1.40-1.39 (m, 4H), 0.93 (s, 6H) ppm. $^{13}$C-NMR (100 MHz, CDCl$_3$) δ: 164.1, 154.4, 138.4, 137.9, 136.5, 133.6, -continued

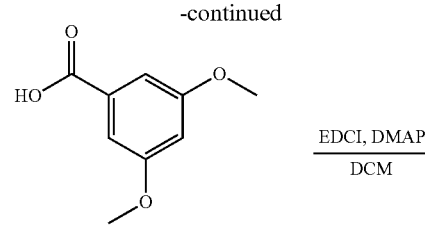

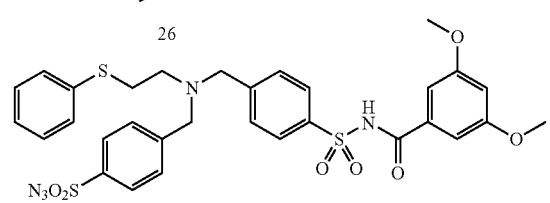

The solution of (SZ10) (1 mmol), 26 (1 mmol), EDCI (2 mmol) and DMAP (0.2 mmol) in DCM was stirred for 12 hours at room temperature, and the system was extracted by ethyl acetate (20 mL×3). The combined organic phase was dried by anhydrous sodium sulfate and concentrated. And product (SZ9TA5) (0.5 mmol, 50%) was obtained by flash chromatography (hexane:EtOAc=1:1; Rf=0.2 in hexane:EtOAc=1:1). $^1$H-NMR (400 MHz, CDCl$_3$) δ: 7.97 (d, J=7.2 Hz, 2H), 7.78 (d, J=8.0 Hz, 2H), 7.46 (d, J=7.6 Hz, 2H), 7.28-6.99 (m, 10H), 6.42 (s, 1H), 3.64-3.56 (m, 10H), 2.98-2.94 (m, 2H), 2.63 (bs, 2H) ppm. $^{13}$C-NMR (100 MHz, CDCl$_3$) δ: 160.7, 147.3, 137.2, 136.0, 129.8, 129.2, 129.0, 127.7, 126.4, 106.6, 105.3, 58.1, 57.9, 55.6, 52.9, 31.5 ppm. HRMS (ESI$^+$) for [M+H]$^+$; calculated: 682.14584. found: 682.14395 (error m/z=−2.77 ppm).

3.3 Acylsulfonamide (SZ10TA2) (and Acylsulfonamide (SZ9TA2))

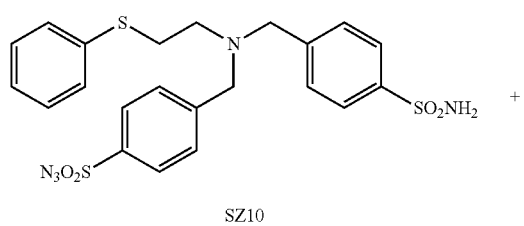
SZ10

+

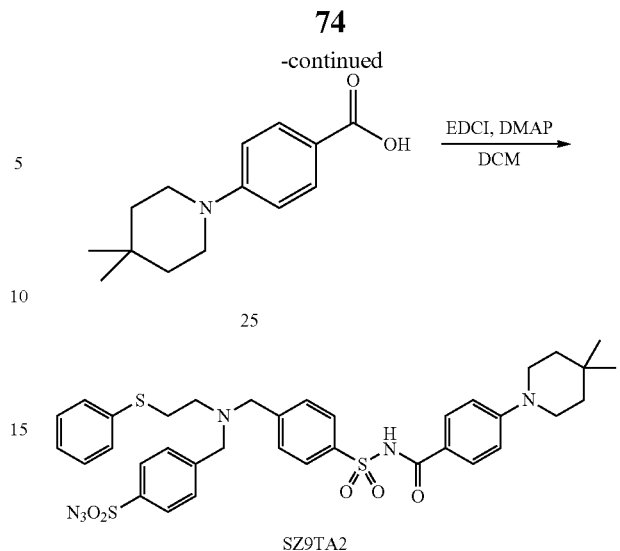
25

(SZ9TA2) was prepared starting from (SZ10) and known 25 using the procedure described for the preparation of (SZ9TA5) in 40% yield. $^1$H-NMR (400 MHz, CDCl$_3$) δ: 8.09 (d, J=8.4 Hz, 2H), 7.85 (d, J=8.0 Hz, 2H), 7.63 (d, J=8.6 Hz, 2H), 7.56 (d, J=8.4 Hz, 2H), 7.51 (d, J=8.0 Hz, 2H), 7.24-7.16 (m, 7H), 6.86 (d, J=9.2 Hz, 2H), 3.77 (d, J=4.8 Hz, 4H), 3.32 (t, J=4.8 Hz, 4H), 3.06 (t, J=7.2 Hz, 2H), 2.79 (t, J=7.2 Hz, 2H), 1.47 (t, J=5.6 Hz, 4H), 0.98 (s, 6H) ppm. $^{13}$C-NMR (100 MHz, CDCl$_3$) δ: 154.1, 147.0, 137.0, 135.7, 130.0, 129.5, 129.0, 128.9, 128.7, 128.3, 127.5, 126.1, 113.1, 57.9, 57.7, 52.7, 43.9, 37.8, 31.3, 28.5, 27.7, 27.6 ppm. HRMS (ESI$^+$) for [M+H]$^+$; calculated: 733.22951. found: 733.22965 (error m/z=0.19 ppm).

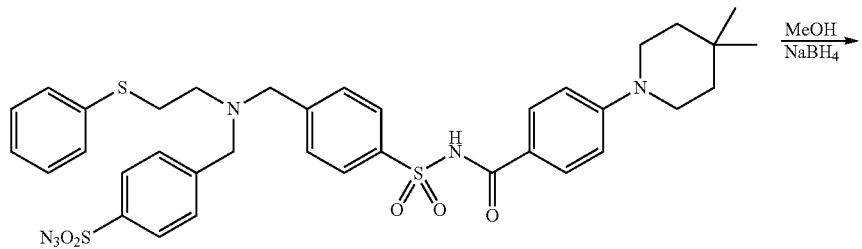
SZ9TA2

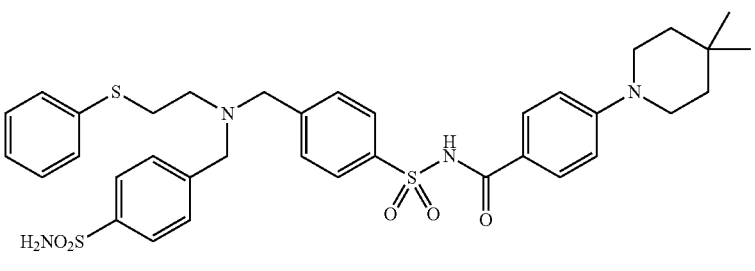
SZ10TA2

(SZ10TA2) was prepared starting from (SZ9TA2) using the procedure described for the preparation of compounds 24 in 86% yield. $^1$H-NMR (400 MHz, CDCl$_3$) δ: 7.92 (d, J=7.2 Hz, 2H), 7.85 (d, J=7.2 Hz, 2H), 7.79 (d, J=7.2 Hz, 2H), 7.46 (d, J=7.6 Hz, 2H), 7.37 (d, J=7.6 Hz, 2H), 7.14-7.02 (m, 5H), 6.81 (d, J=8.0 Hz, 2H), 3.57 (d, J=10.8 Hz, 4H), 3.34-3.30 (m, 4H), 3.00 (t, J=7.2 Hz, 2H), 2.62 (t, J=7.2 Hz, 2H), 1.44 (t, J=5.2 Hz, 4H), 0.95 (s, 6H) ppm. $^{13}$C-NMR (100 MHz, CDCl$_3$) δ: 155.3, 145.6, 144.6, 143.6, 137.5, 130.4, 130.0, 129.8, 129.7, 128.3, 127.2, 126.9, 114.8, 62.9, 58.9, 54.0, 45.8, 39.2, 29.5, 28.3 ppm. HRMS (ESI$^+$) for [M+H]$^+$; calculated: 707.23901. found: 707.23934 (error m/z=0.46 ppm).

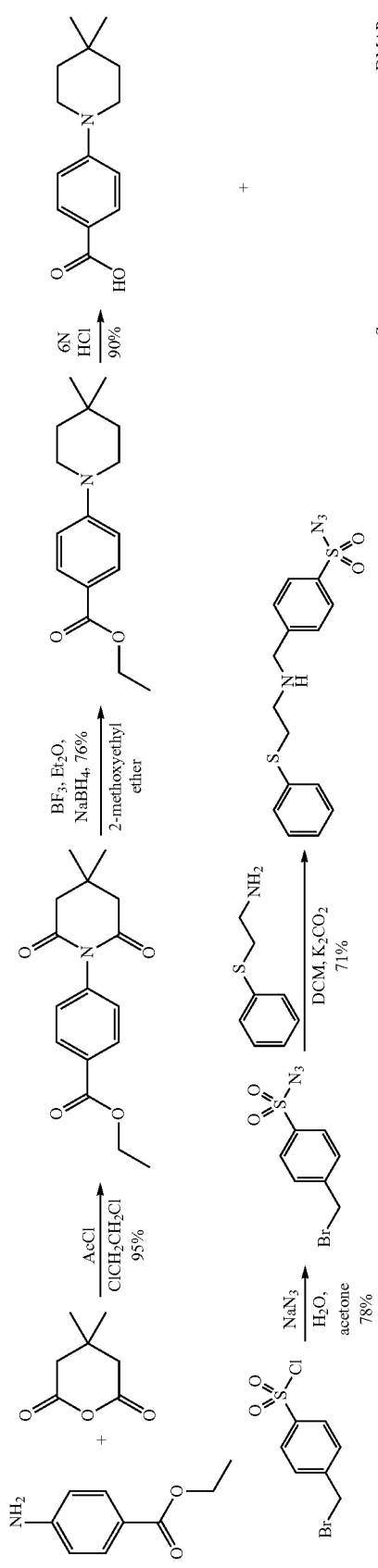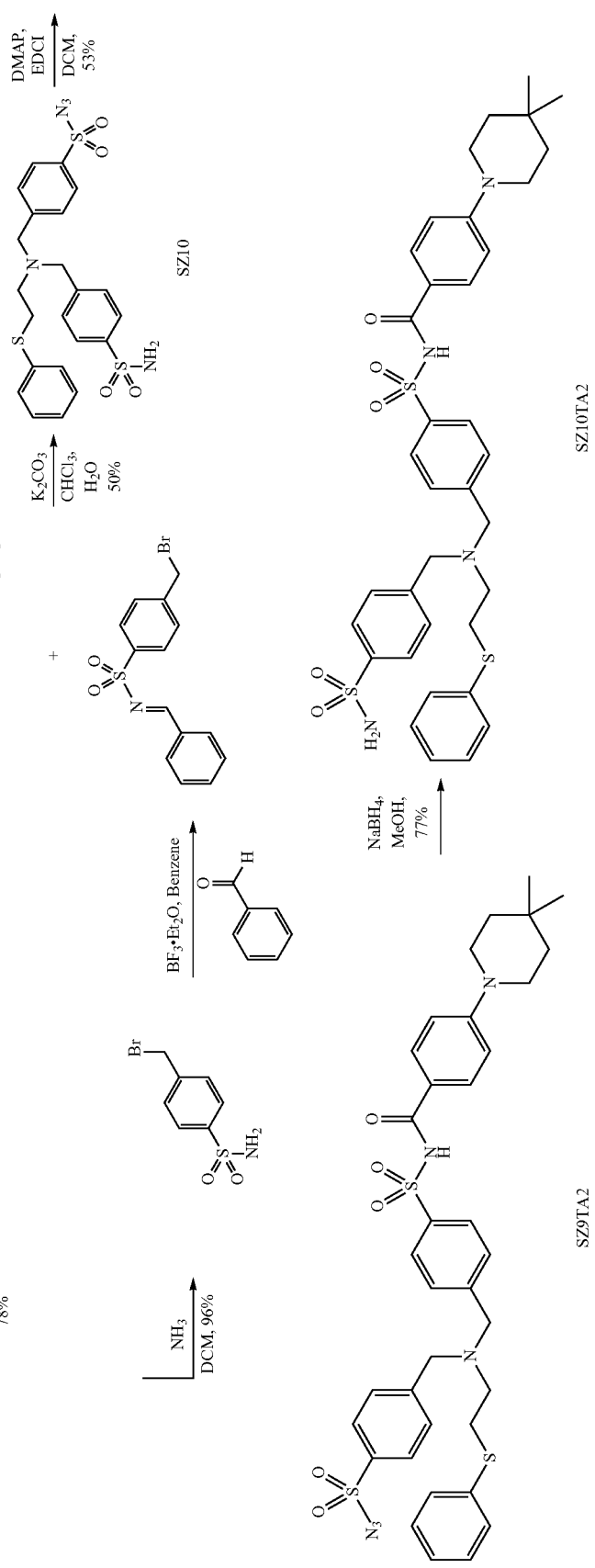

3.4 Acylsulfonamide (SZ15TA3)

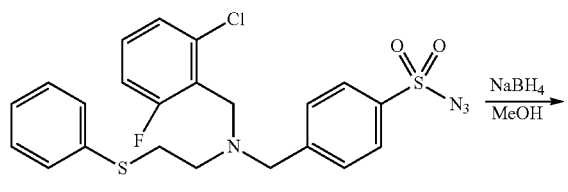

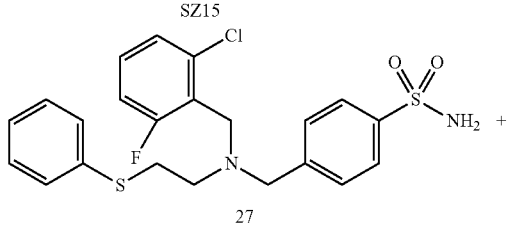

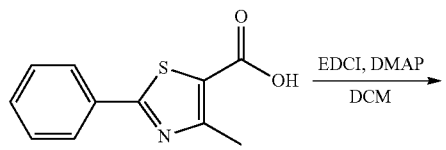

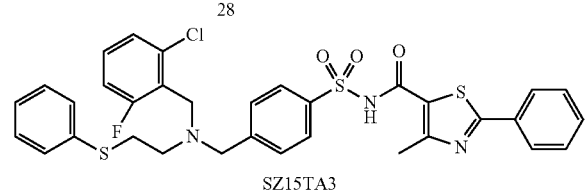

Sodium boron hydride (60 mg, 1.5 mmol) was added slowly to the solution of (SZ15) (1 mmol) in Methanol. The system was stirred for 30 min and removed all the solvent. Intermediate 27 was obtained by flash chromatography and used for next step directly. The solution of 27, 28 (1 mmol), EDCI (2 mmol) and DMAP (0.2 mmol) in DCM was stirred for 12 hours at room temperature, and the system was extracted by ethyl acetate (20 mL×3). The combined organic phase was dried by anhydrous sodium sulfate and concentrated. And product (SZ15TA3) (0.5 mmol, 50%) was obtained by purification on preparative HPLC. $^1$H-NMR (400 MHz, CDCl$_3$) δ: 9.95 (s, 2H), 7.99 (d, J=7.5 Hz, 2H), 7.77 (d, J=7.5 Hz, 2H), 7.53 (d, J=7.5 Hz, 2H), 7.35-7.12 (m, 10H), 6.92 (t, J=7.5 Hz, 1H), 4.23 (bs, 4H), 3.14-3.12 (m, 4H), 2.57 (s, 3H) ppm. $^{13}$C-NMR (100 MHz, CDCl$_3$) δ: 169.8, 160.3 (d, $^1J_{CF}$=150 Hz), 160.2, 139.9, 136.9 (d, $^2J_{CF}$=12.5 Hz), 132.8, 132.5 (d, $^3J_{CF}$=10 Hz), 131.9, 131.7, 131.0, 130.8, 129.4, 129.2, 129.2, 127.6, 127.0, 126.3, 122.0, 117.1, 116.8, 114.9 (d, $^2J_{CF}$=21.5 Hz), 57.5, 52.7, 48.9, 28.8, 17.7 ppm. HRMS (ESI$^+$) for [M+H]$^+$; calculated: 666.11164. found: 666.10968 (error m/z=−2.94 ppm).

3.5 Acylsulfonamide (SZ15TA8)

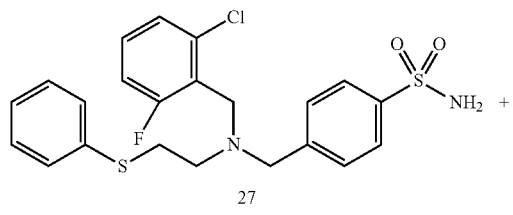

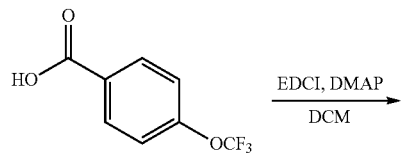

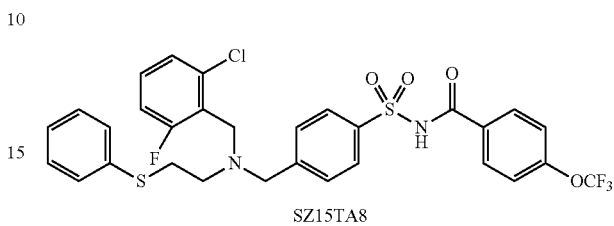

The solution of 27, 29 (1 mmol), EDCI (2 mmol) and DMAP (0.2 mmol) in DCM was stirred for 12 hours at room temperature, and the system was extracted by ethyl acetate (20 mL×3). The combined organic phase was dried by anhydrous sodium sulfate and concentrated. And product (SZ15TA8) (0.82 mmol, 82%) was obtained by purification on preparative HPLC. $^1$H-NMR (400 MHz, CDCl$_3$) δ: 10.9 (bs, 1H), 8.04 (d, J=8.0 Hz, 2H), 7.90 (d, J=8.4 Hz, 2H), 7.61 (d, J=8.0 Hz, 2H), 7.23-7.09 (m, 9H), 6.93 (t, J=8.4 Hz, 1H), 4.27 (s, 2H), 4.25 (s, 2H), 3.23-3.16 (m, 4H) ppm. $^{13}$C-NMR (100 MHz, CDCl$_3$) δ: 164.1, 162.6 (d, $^1J_{CF}$=250 Hz), 161.2 (d, $^2J_{CF}$=37 Hz), 152.7, 139.6, 137.6, 136.6, 133.0, 132.1 (d, $^3J_{CF}$=9.5 Hz), 130.8, 130.3, 129.4, 129.2, 129.0, 127.3, 126.1, 121.4, 120.3, 118.8, 117.5, 117.4, 114.6 (d, $^2J_{CF}$=22.6 Hz), 57.4, 52.7, 48.8, 28.7 ppm. HRMS (ESI$^+$) for [M+H]$^+$; calculated: 653.09532. found: 653.09349 (error m/z=−2.79 ppm).

3.6 Acylsulfonamide (SZ16TA6)

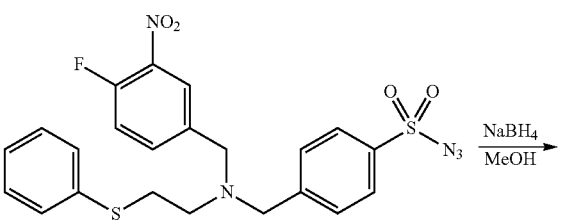

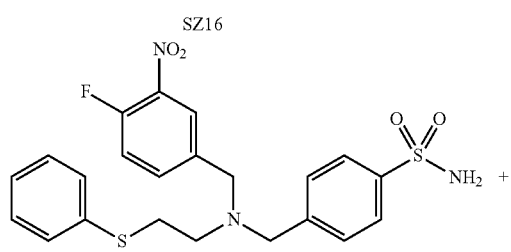

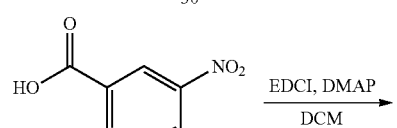

-continued

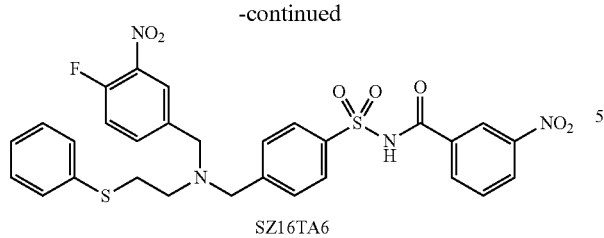

SZ16TA6

Compound 30 was prepared starting from (SZ16) using the procedure described for the preparation of compounds 27, and (SZ16TA6) was prepared starting from 30 and 31 using the procedure described for the preparation of compounds (SZ15TA8) in 46% yield. $^1$H-NMR (400 MHz, CD$_3$CN) δ: 8.58 (s, 1H), 8.36 (d, J=8.0 Hz, 1H), 8.15 (d, J=7.6 Hz, 1H), 8.10 (d, J=6.8 Hz, 1H), 8.02 (d, J=7.6 Hz, 2H), 7.69-7.65 (m, 2H), 7.62 (d, J=8.0 Hz, 2H), 7.28 (t, J=10 Hz, 1H), 7.17-7.14 (m, 4H), 7.09 (dd, J=8.0, 4.0 Hz, 1H), 3.97 (s, 2H), 3.93 (s, 2H), 3.15 (t, J=7.2 Hz, 2H), 2.86 (t, J=7.2 Hz, 2H) ppm. $^{13}$C-NMR (100 MHz, CD$_3$CN) δ: 163.8, 155.1 (d, $^1J_{CF}$=261 Hz), 148.4, 142.3, 138.9, 137.4 (d, $^3J_{CF}$=9.1 Hz), 135.1, 134.5, 133.3 (d, $^2J_{CF}$=21.4 Hz), 130.4, 129.3, 129.2, 128.7, 127.8, 127.4, 126.5, 123.4, 118.7 (d, $^2J_{CF}$=21.3 Hz), 117.6, 57.2, 56.5, 52.2, 29.2 ppm.

3.7 Acylsulfonamide (SZ16TA8)

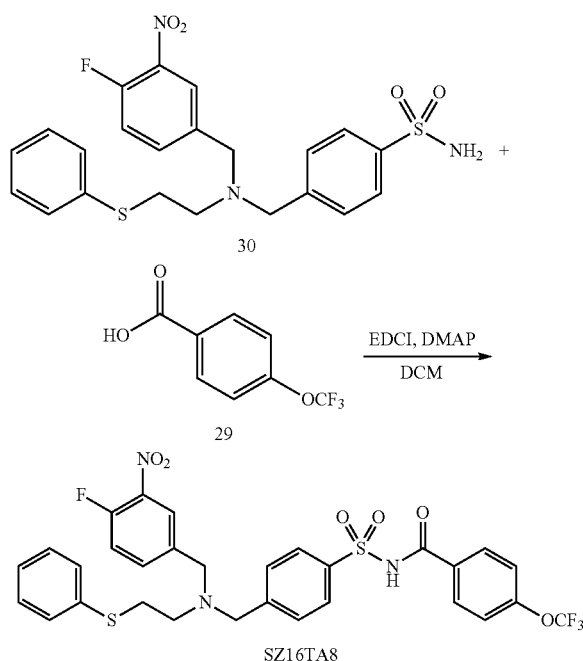

SZ16TA8

(SZ16TA8) was prepared starting from 30 and 29 using the procedure described for the preparation of compounds (SZ15TA8) in 36% yield. $^1$H-NMR (400 MHz, CD$_3$CN) δ: 8.18 (dd, J=6.8, 1.6 Hz, 1H), 8.04 (d, J=8.0 Hz, 2H), 7.90 (d, J=8.8 Hz, 2H), 7.75 (dd, J=4.4, 2.4 Hz, 1H), 7.64 (d, J=8.4 Hz, 2H), 7.37 (d, J=8.8 Hz, 2H), 7.34-7.31 (m, 1H), 7.20-7.15 (m, 4H), 4.20 (s, 2H), 4.17 (s, 2H), 3.23-3.19 (m, 2H), 3.03-2.99 (m, 2H), 2.62 (t, J=7.2 Hz, 2H), 1.44 (t, J=5.2 Hz, 4H), 0.95 (s, 6H) ppm. $^{13}$C-NMR (100 MHz, CD$_3$CN) δ: 164.3, 155.6 (d, $^1J_{CF}$=263 Hz), 152.6, 139.9, 138.8, 138.3 (d, $^3J_{CF}$=10 Hz), 134.0, 131.2, 130.9, 130.5, 130.0, 129.4, 128.9, 128.5, 127.1, 120.9, 119.1 (d, $^2J_{CF}$=21.4 Hz), 57.0, 56.4, 51.7, 28.3 ppm.

3.8 Acylsulfonamide (SZ17TA7)

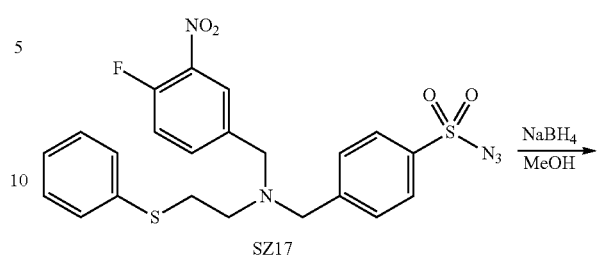

Compound 33 was prepared starting from (SZ17) using the procedure described for the preparation of compounds 27, and (SZ17TA7) was prepared starting from 33 and 32 using the procedure described for the preparation of compounds (SZ15TA8) in 36% yield. HRMS (ESI$^+$) for [M+H$_2$O]$^+$; calculated: 614.19037. found: 614.18830 (error m/z=−3.36 ppm).

EXAMPLE 4

Preparation of Other Compounds 4.1 Acylsulfonamide (SZ2TA1)

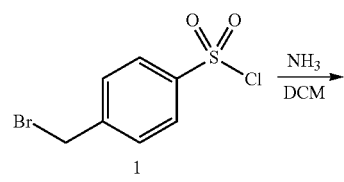

-continued

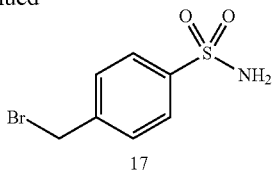

17

Ammonia gas was passed through a solution of compound 1 (1 g, 3.7 mmol) in DCM (100 mL) at 0° C. for 10 minutes. Brine (20 mL) was added. The separated organic phase was dried over anhydrous sodium sulfate and concentrated. The product 17 (900 mg, 96.8%) was isolated by flash chromatography (hexanes:EtOAc=2:1). $^1$H-NMR (250 MHz, Acetone-d6) δ: 7.91 (d, J=10.0 Hz, 2H), 7.67 (d, J=10.0 Hz, 2H), 6.63 (bs, 2H), 4.74 (s, 2H) ppm.

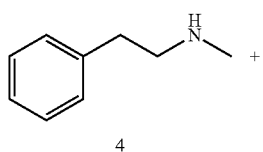

4

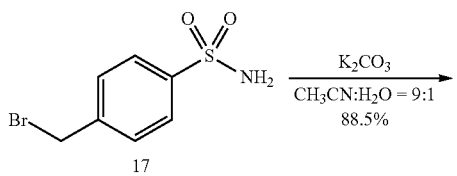

18

A mixture of 17 (100 mg, 0.40 mmol), 4 (54.3 mg, 0.40 mmol) and potassium carbonate (100 mg, 0.72 mmol) in acetonitrile and water (9:1) was stirred at room temperature for 12 hours. To this mixture, ethyl acetate (20 mL) and water (20 mL) were added, and the resulting biphasic mixture was extracted by ethyl acetate (20 mL×3). The combined organic phases were dried over anhydrous sodium sulfate and concentrated. Product 18 (108 mg, 88.5%) was obtained by flash chromatography (hexane:EtOAc=1:1; Rf=0.2 in hexane:EtOAc=1:1). $^1$H-NMR (250 MHz, CDCl$_3$) δ: 7.73 (d, J=10.0 Hz, 2H), 7.30 (d, J=10.0 Hz, 2H), 7.22-7.07 (m, 5H), 5.18 (bs, 2H), 3.51 (s, 2H), 2.76-2.70 (m, 2H), 2.60-2.54 (m, 2H), 2.19 (s, 3H) ppm. $^{13}$C-NMR (62.5 MHz, CDCl$_3$) δ: 144.6, 140.6, 140.2, 129.4, 128.7, 128.4, 126.4, 126.1, 61.6, 59.1, 42.2, 33.8 ppm. HRMS (ESI$^+$) for [M+H]$^+$; calculated: 305.1324. found: 305.1325. (error m/z=0.3 ppm).

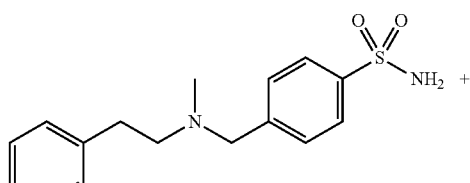

18

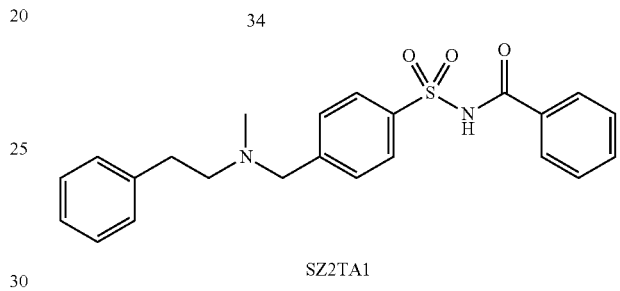

34

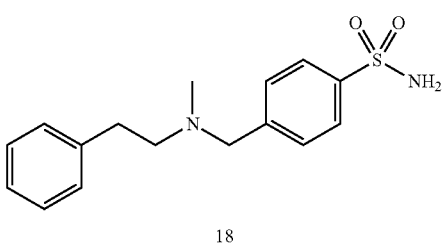

SZ2TA1

A mixture of 34 (31 mg, 0.25 mmol), 18 (76 mg, 0.25 mmol), EDCI (60 mg, 0.314 mmol) and DMAP (8 mg, 0.065 mmol) in dichloromethane (10 mL) was stirred for 19 h. Product (SZ2TA1) (87 mg, 85%) was isolated after flash chromatography (DCM: MeOH=18:1). Rf=0.68 (DCM: MeOH=4:1). $^1$H-NMR (400 MHz, DMSO-d6) δ: 7.86 (d, J=7.6 Hz, 4H), 7.48 (d, J=8 Hz, 2H), 7.37-7.19 (m, 8H), 4.16 (bs, 2H), 3.09-3.07 (m, 2H), 2.94-2.90 (m, 2H), 2.58 (s, 3H) ppm. $^{13}$C-NMR (100 MHz, DMSO-d6) δ: 169.7, 146.2, 138.4, 131.2, 130.6, 129.9, 129.4, 129.2, 129.0, 128.3, 128.0, 127.3, 59.5, 57.4, 31.1 ppm. HRMS (ESI$^+$) for [M+H]$^+$; calculated: 409.1586. found: 409.1582 (error m/z=−0.9 ppm).

4.2 Acylsulfonamide (SZ2TA2)

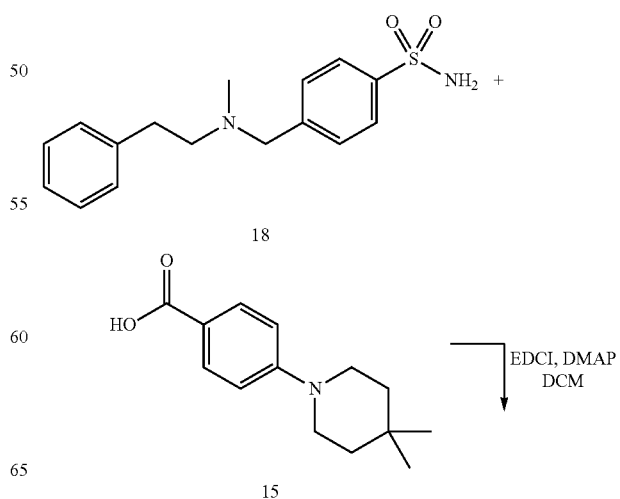

18

15

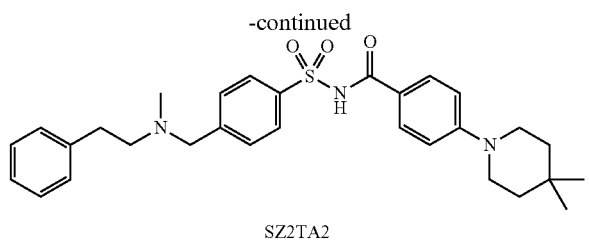

SZ2TA2

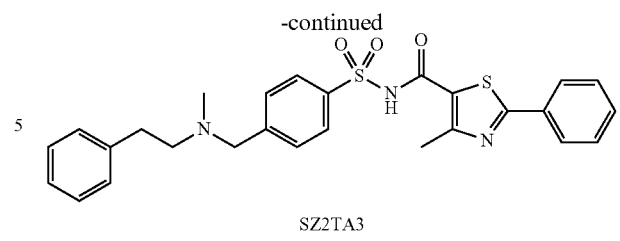

SZ2TA3

A solution of 15 (58 mg, 0.25 mmol), 18 (76 mg, 0.25 mmol), EDCI (60 mg, 0.314 mmol) and DMAP (8 mg, 0.065 mmol) in dichloromethane (10 mL) was stirred for 19 hours. Product (SZ2TA2) (42 mg, 32.5%) was isolated after flash chromatography (DCM: MeOH=24:1). Rf=0.6 (DCM: MeOH=6:1). $^1$H-NMR (400 MHz, DMSO-d6) δ: 7.85 (d, J=8 Hz, 2H), 7.69 (d, J=8.8 Hz, 2H), 7.44 (d, J=8 Hz, 2H), 7.24-7.16 (m, 6H), 6.84 (d, J=8.8 Hz, 2H), 3.80 (bs, 2H), 3.27-3.24 (m, 4H), 3.14 (s, 2H), 2.79 (bs, 4H), 2.33 (s, 3H), 1.35-1.32 (m, 2H), 0.91 (s, 6H) ppm. $^{13}$C-NMR (100 MHz, DMSO-d6) δ: 166.9, 153.9, 139.9, 130.7, 129.9, 129.3, 129.0, 128.1, 126.8, 126.3, 113.5, 60.5, 58.5, 44.5, 41.7, 38.1, 32.6, 29.1, 28.3, 28.2 ppm. HRMS (ESI$^+$) for [M+H]$^+$; calculated: 520.2634. found: 520.2627 (error m/z=1.3 ppm).

4.3 Acylsulfonamide (SZ2TA3)

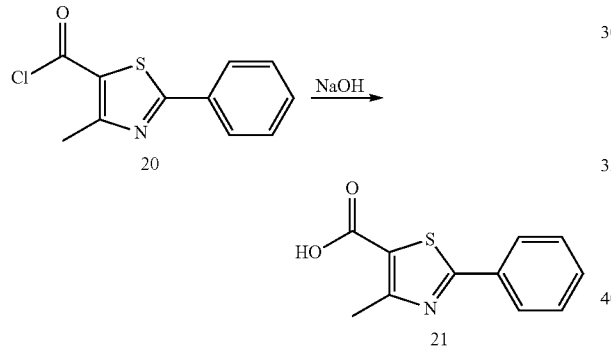

Compound 20 (500 mg, 2.1 mmol) was added into 1M NaOH and then stirred overnight. The resulting mixture was treated with 2N HCl. Product 21 (310 mg, 67%) can be filtered out and dried. The crude product was used for next step directly.

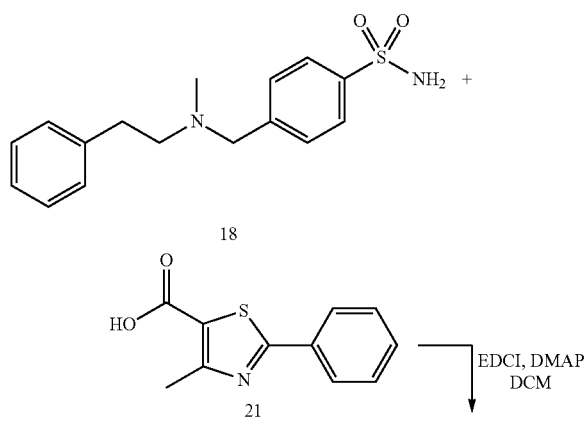

A solution of 21 (45 mg, 0.205 mmol), 18 (61 mg, 0.205 mmol), EDCI (60 mg, 0.314 mmol) and DMAP (8 mg, 0.065 mmol) in dichloromethane (10 mL) was stirred for 24 h. Product (SZ2TA3) (58 mg, 55%) was isolated by preparative HPLC. (DCM: MeOH=36:1). Rf=0.55 (DCM: MeOH=8:1). $^1$H-NMR (250 MHz, Acetone-d6) δ: 8.03 (d, J=8 Hz, 2H), 7.85-7.78 (m, 4H), 7.39-7.36 (m, 3H), 7.14-7.11 (m, 5H), 4.52 (bs, 2H), 3.36-3.32 (m, 2H), 3.12-3.09 (m, 2H), 2.84 (s, 3H), 2.48 (s, 3H) pm. $^{13}$C-NMR (100 MHz, CDCl$_3$) δ: 169.7, 161.2, 159.8, 140.9, 135.1, 134.4, 131.8, 131.6, 131.5, 129.2, 129.1, 129.0, 128.6, 127.5, 126.9, 122.4, 59.3, 57.5, 39.6, 30.5, 17.5 ppm. HRMS (ESI$^+$) for [M+H]$^+$; calculated: 506.1572. found: 506.1565 (error m/z=-1.4 ppm).

4.4 Acylsulfonamide (SZ4TA1)

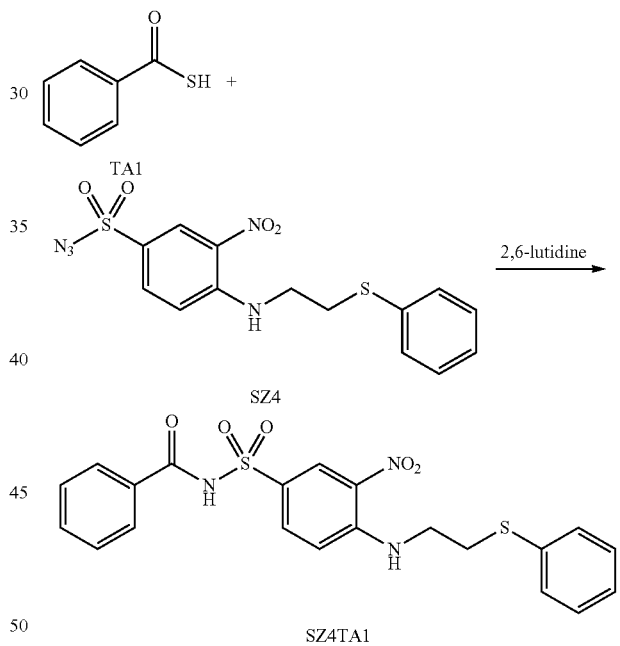

A solution of (TA1) (50 mg, 0.36 mmol), (SZ4) (136 mg, 0.36 mmol) and 2,6-lutidine (40 mg, 0.37 mmol) in chloroform (10 mL) was stirred at 70° C. for 16 h. Chloroform (30 mL) was added to the reaction and the resulting mixture was washed sequentially with saturated copper sulfate aqueous solution (50 mL) and brine (20 mL). The organic phase was then dried over anhydrous sodium sulfate and concentrated. Product (SZ4TA1) (89 mg, 54%) was isolated after flash chromatography (DCM: MeOH=26:1). Rf=0.58 (DCM: MeOH=8:1). $^1$H-NMR (400 MHz, CDCl$_3$) δ: 8.93 (s, 1H), 8.87 (d, J=1.2 Hz, 1H), 8.68 (s, 1H), 8.13 (d, J=8.4 Hz, 1H), 7.76 (d, J=7.6 Hz, 2H), 7.56 (t, J=7.2 Hz, 1H), 7.45-7.37 (m, 4H), 7.29-7.22 (m, 4H), 6.81 (d, J=8.8 Hz, 1H), 3.58-3.54 (m, 2H), 3.20-3.17 (m, 2H) ppm. $^{13}$C-NMR (100 MHz, CDCl$_3$) δ: 164.3, 147.6, 135.5, 133.7, 131.2, 130.9, 129.3, 129.0, 127.7, 127.4, 124.5, 113.7, 42.1, 33.2 ppm. HRMS (ESI⁺) for [M+H]⁺; calculated: 458.08389. found: 458.08350 (error m/z=−0.84 ppm).

4.5 Acylsulfonamide (SZ5TA1)

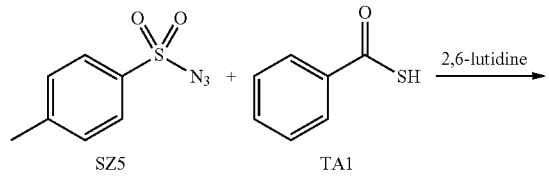

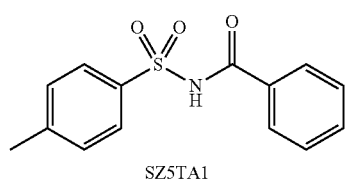

A solution of (TA1) (50 mg, 0.36 mmol), (SZ5) (71 mg, 0.36 mmol) and 2,6-lutidine (40 mg, 0.37 mmol) in chloroform (10 mL) was stirred at 70° C. for 16 h. Chloroform (30 mL) was added to the reaction and the resulting mixture was washed sequentially with saturated copper sulfate aqueous solution (50 mL) and brine (20 mL). The organic phase was then dried over anhydrous sodium sulfate and concentrated. Product (SZ5TA1) (67 mg, 68%) was isolated after flash chromatography (DCM: MeOH=38:1). Rf=0.7 (DCM: MeOH=10:1). ¹H-NMR (250 MHz, CDCl₃) δ: 9.62 (s, 1H), 7.95 (d, J=8 Hz, 2H), 7.75 (d, J=8.0 Hz, 2H), 7.43 (t, J=7.2 Hz, 1H), 7.32-7.22 (m, 4H), 2.32 (s, 3H) ppm. ¹³C-NMR (100 MHz, CDCl₃) δ: 164.5, 145.1, 135.4, 133.4, 129.5, 128.7, 128.5, 127.9, 127.8, 21.6 ppm. HRMS (ESI) for [M+H]⁺; calculated: 276.0694. found: 276.0696 (error m/z=−0.7 ppm).

4.6 Acylsulfonamide (SZ5TA2)

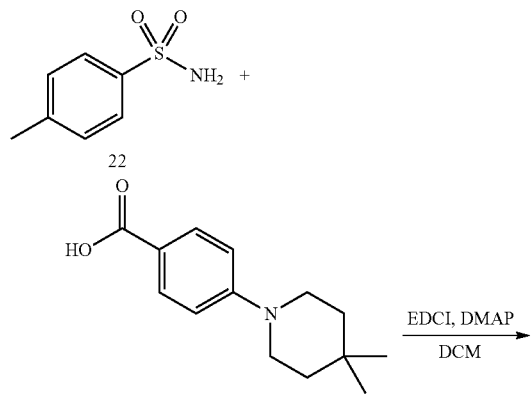

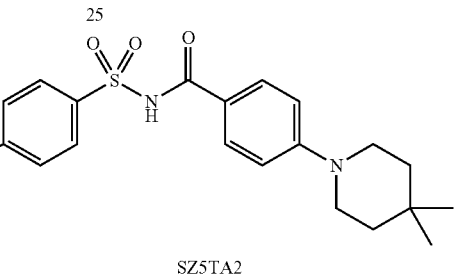

A solution of 15 (58 mg, 0.25 mmol), 22 (43 mg, 0.25 mmol), EDCI (60 mg, 0.314 mmol) and DMAP (8 mg, 0.065 mmol) in dichloromethane (10 mL) was stirred for 30 h. Product (SZ5TA2) (68 mg, 70%) was isolated after flash chromatography (DCM: MeOH=16:1). Rf=0.6 (DCM: MeOH=8:1). ¹H-NMR (400 MHz, CDCl₃) δ: 8.70 (bs, 1H), 8.00 (d, J=8 Hz, 2H), 7.63 (d, J=8.4 Hz, 2H), 7.30 (d, J=8 Hz, 2H), 6.82 (d, J=7.6 Hz, 2H), 3.30 (t, J=6 Hz, 4H), 2.40 (s, 3H), 1.46 (bs, 4H), 0.97 (s, 6H) ppm. ¹³C-NMR (100 MHz, DMSO-d6) δ: 165.1, 154.4, 144.5, 137.9, 130.9, 130.0, 128.3, 119.2, 113.4, 43.9, 38.0, 29.2, 28.3, 21.9 ppm. HRMS (ESI⁺) for [M+H]⁺; calculated: 387.1742. found: 387.1742 (error m/z=−1.8 ppm).

4.7 Acylsulfonamide (SZ9TA1)

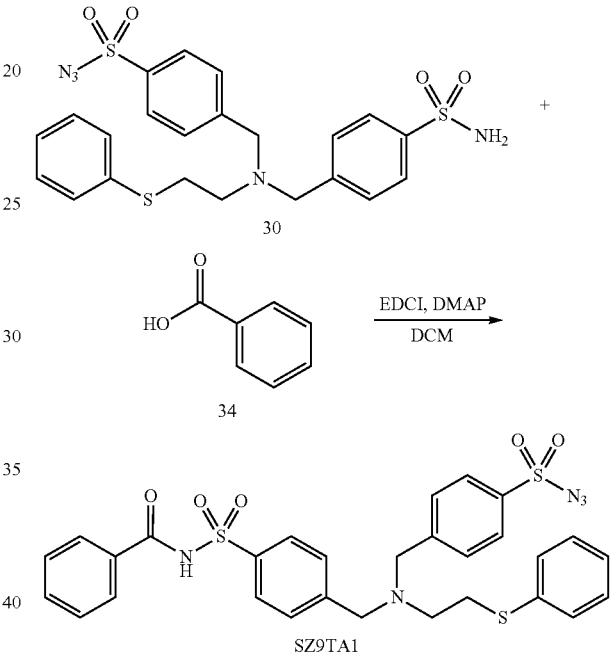

(SZ9TA1) was prepared starting from 30 and 34 using the procedure described for the preparation of compounds (SZ15TA8) in 37% yield. ¹H-NMR (400 MHz, CDCl₃) δ: 8.03 (d, J=8.4 Hz, 2H), 7.78 (d, J=8.4 Hz, 2H), 7.71 (d, J=7.6 Hz, 2H), 7.51-7.46 (m, 4H), 7.41-7.33 (m, 3H), 7.19-7.04 (m, 5H), 3.61 (s, 4H), 2.99 (t, J=7.2 Hz, 2H), 2.68 (t, J=7.2 Hz, 2H) ppm. ¹³C-NMR (100 MHz, CD₃CN) δ: 170.0, 164.3, 146.9, 145.6, 137.4, 137.2, 135.7, 133.5, 131.2, 130.1, 129.5, 129.1, 128.9, 128.8, 128.4, 127.7, 127.6, 126.3, 58.0, 57.9, 52.8, 31.5 ppm. HRMS (ESI⁺) for [M+H]⁺; calculated: 622.12471. found: 622.12402 (error m/z=−1.10 ppm).

4.8 Acylsulfonamide (SZ10TA1)

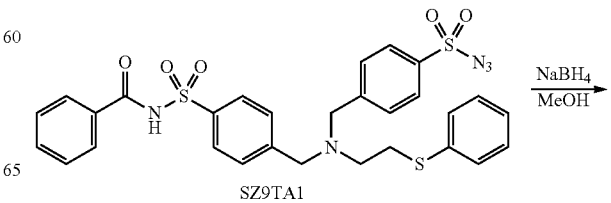

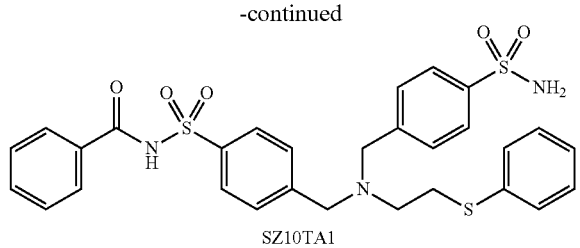

SZ10TA1

Sodium boron hydride (60 mg, 1.5 mmol) was added slowly to the solution of (SZ9TA1) (1 mmol) in Methanol. The system was stirred for 30 min and removed all the solvent. (SZ10TA1) was obtained by flash chromatography (hexane:EtOAc=1:1; Rf=0.15 in hexane:EtOAc=1:1). $^1$H-NMR (400 MHz, CD$_3$OD) δ: 8.04 (d, J=8.0 Hz, 2H), 7.92 (d, J=7.6 Hz, 2H), 7.79 (d, J=7.6 Hz, 2H), 7.44-7.27 (m, 7H), 7.12-6.97 (m, 5H), 3.55 (s, 2H), 3.49 (s, 2H), 2.96 (t, J=7.2 Hz, 2H), 2.57 (t, J=7.2 Hz, 2H) ppm. $^{13}$C-NMR (100 MHz, CD$_3$OD) δ: 173.4, 144.3, 143.6, 142.4, 137.0, 136.3, 131.5, 129.2, 129.0, 128.8, 128.7, 128.6, 127.7, 126.5, 126.0, 125.7, 57.7, 52.7, 30.7 ppm. HRMS (ESI) for [M+H]$^+$; calculated: 596.13421. found: 596.13388 (error m/z=−0.55 ppm).

4.9 Acylsulfonamide (SZ10TA5)

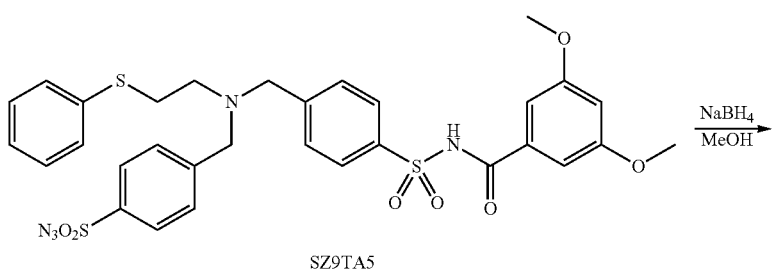

SZ9TA5

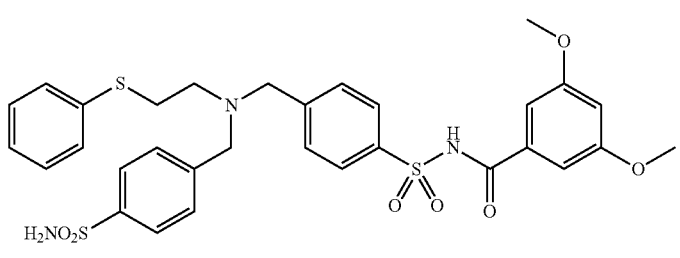

SZ10TA5

(SZ10TA5) was prepared starting from (SZ9TA5) using the procedure described for the preparation of compounds (SZ10TA1) in 91% yield. $^1$H-NMR (400 MHz, CDCl$_3$) δ: 7.96 (d, J=8.0 Hz, 2H), 7.80 (d, J=8.04 Hz, 2H), 7.50-7.44 (m, 4H), 7.15-7.01 (m, 7H), 6.57 (d, J=1.6 Hz, 1H), 3.71 (s, 6H), 3.60 (s, 2H), 3.58 (s, 2H), 3.31-3.30 (m, 2H), 2.64-2.60 (m, 2H) ppm. $^{13}$C-NMR (100 MHz, CD$_3$CN) δ: 171.0, 162.0, 145.7, 145.2, 143.5, 141.6, 138.0, 137.4, 130.6, 130.4, 129.9, 129.8, 128.7, 127.1, 126.9, 107.3, 105.6, 58.8, 56.1, 55.9, 53.9, 31.8 ppm. HRMS (ESI$^+$) for [M+H]$^+$; calculated: 656.15534. found: 656.15466 (error m/z=−1.03 ppm).

4.10 Acylsulfonamide (SZ15TA1)

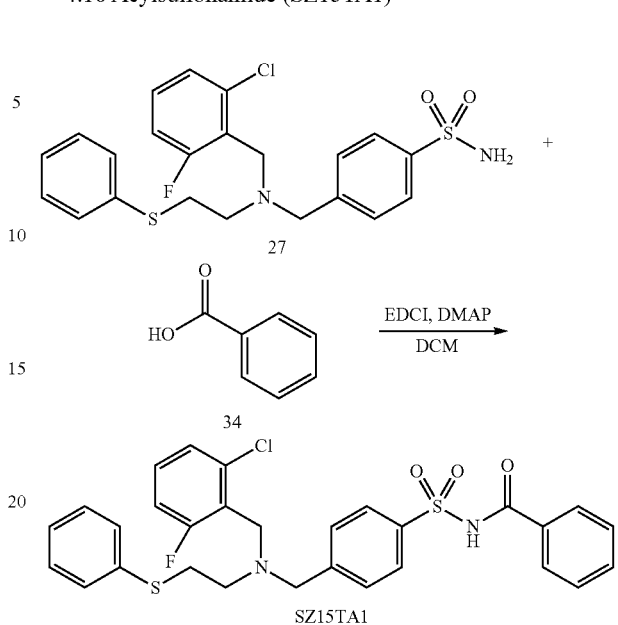

(SZ15TA1) was prepared starting from 27 and 34 using the procedure described for the preparation of (SZ15TA3) in 61% yield. $^1$H-NMR (400 MHz, CD$_3$CN) δ: 8.07 (d, J=8.4 Hz, 2H), 7.82 (d, J=7.6 Hz, 2H), 7.21 (d, J=8.0 Hz, 2H), 7.61 (t, J=7.2 Hz, 1H), 7.47 (t, J=7.6 Hz, 2H), 7.38-7.34 (m, 1H), 7.26-7.12 (m, 6H), 7.07 (t, J=8.8 Hz, 1H), 4.40 (s, 2H), 4.32 (s, 2H), 3.35-3.31 (m, 2H), 3.25-3.21 (m, 2H) ppm. $^{13}$C-NMR (100 MHz, CD$_3$CN) δ: 165.9, 162.7 (d, $^1J_{CF}$=249 Hz), 160.5, 160.1, 140.9, 137.7, 136.9, 134.1, 133.7, 133.4, 133.3 (d, $^3J_{CF}$=10 Hz), 132.0, 131.9, 130.6, 129.9, 129.3, 128.9, 127.8, 126.7, 115.4 (d, $^2J_{CF}$=22.5 Hz), 57.8, 53.4, 49.4, 28.3 ppm.

4.11 Acylsulfonamide (SZ15TA2)
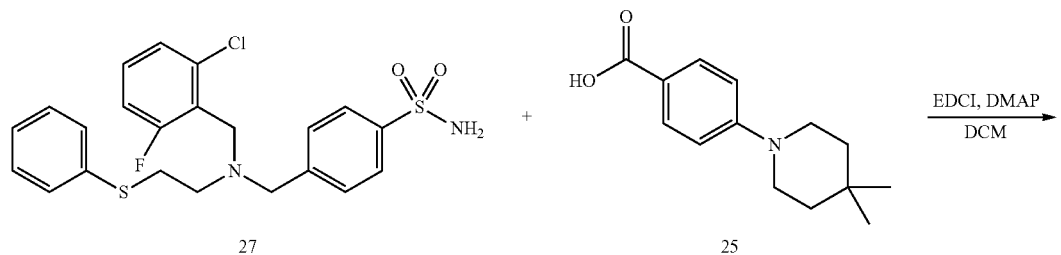
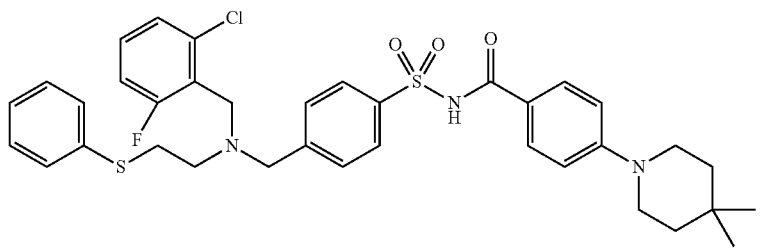
(SZ15TA2) was prepared starting from 27 and 25 using the procedure described for the preparation of (SZ15TA3) in 48.4% yield. $^1$H-NMR (400 MHz, CDCl$_3$) δ: 11.13 (bs, 1H), 7.96 (d, J=7.6 Hz, 2H), 7.79 (d, J=8.0 Hz, 2H), 7.56 (d, J=8.0 Hz, 2H), 7.27-7.12 (m, 10H), 6.93 (t, J=8.8 Hz, 1H), 4.27 (s, 2H), 4.24 (s, 2H), 3.35 (bs, 4H), 3.19 (bs, 2H), 3.15 (bs, 2H), 1.61 (bs, 4H), 0.99 (s, 6H) ppm. $^{13}$C-NMR (100 MHz, CDCl$_3$) δ: 164.2, 162.1 (d, $^1J_{CF}$=241 Hz), 161.3, 160.8, 149.9, 140.0, 137.0, 136.7, 132.9, 132.3 (d, $^3J_{CF}$=9.5 Hz), 130.8, 130.5, 130.3, 129.2, 129.0, 127.4, 126.1, 125.8, 117.4, 114.7 (d, $^2J_{CF}$=22.6 Hz), 57.4, 52.8, 48.8, 48.5, 36.6, 28.6, 27.8, 27.4 ppm.
4.12 Acylsulfonamide (SZ15TA4)
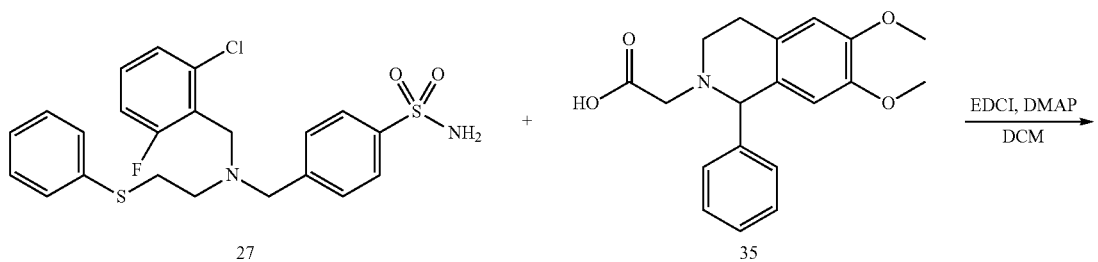
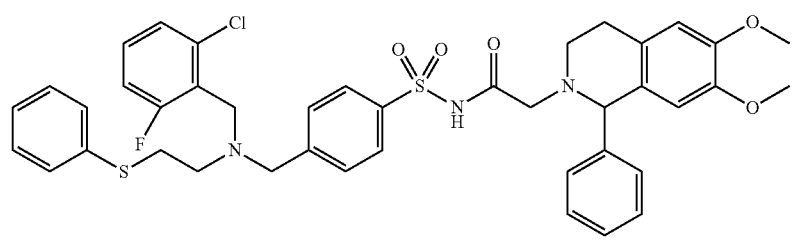

(SZ15TA4) was prepared starting from 27 and 35 using the procedure described for the preparation of (SZ15TA3) in 48.4% yield. $^1$H-NMR (400 MHz, CDCl$_3$) δ: 8.56 (bs, 1H), 7.94 (d, J=8.0 Hz, 2H), 7.59 (d, J=8.0 Hz, 2H), 7.35-7.30 (m, 4H), 7.24-7.18 (m, 10H), 6.98 (t, J=8.4 Hz, 1H), 6.65 (s, 1H), 6.18 (s, 1H), 5.70 (s, 1H), 4.28 (bs, 4H), 4.09 (d, J=16.4 Hz, 1H), 3.89 (d, J=16.8 Hz, 1H), 3.83 (s, 3H), 3.57 (s, 3H), 3.45 (bs, 2H), 3.19-3.02 (m, 6H) ppm. $^{13}$C-NMR (100 MHz, CDCl$_3$) δ: 165.0, 162.4 (d, $^1J_{CF}$=251 Hz), 161.5, 149.8, 148.9, 139.8, 137.4, 137.0, 134.6, 133.2, 132.5 (d, $^3J_{CF}$=9.5 Hz), 131.3, 130.9, 130.7, 130.6, 129.5, 129.0, 127.7, 126.4, 122.9, 120.8, 117.5, 117.3, 115.0 (d, $^2J_{CF}$=22.6 Hz), 111.0 (d, $^2J_{CF}$=14.9 Hz), 66.4, 57.8, 56.1, 56.0, 54.0, 52.9, 49.1, 46.0, 29.0, 23.7 ppm. HRMS (ESI$^+$) for [M+H]$^+$; calculated: 774.22330. found: 774.22223 (error m/z=−1.37 ppm).

4.13 Acylsulfonamide (SZ15TA5)

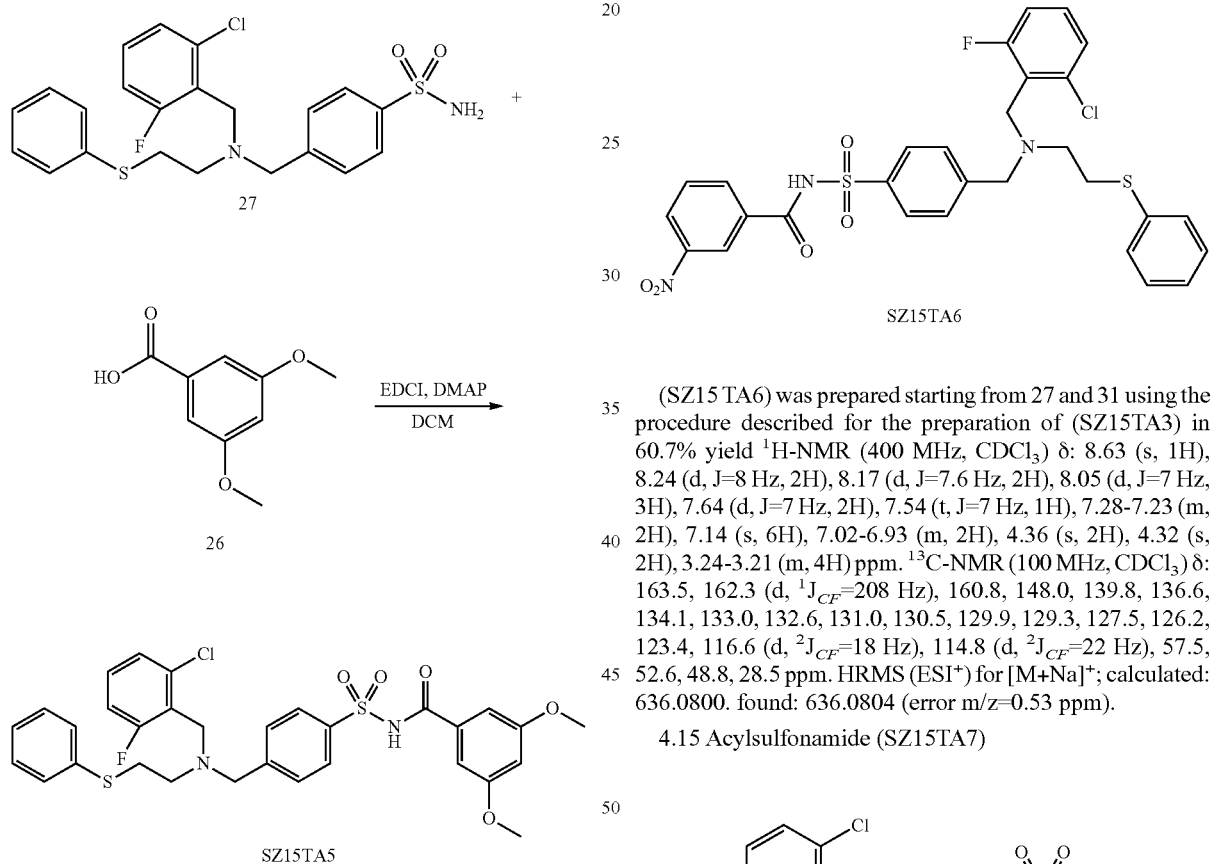

SZ15TA5

(SZ15TA5) was prepared starting from 27 and 26 using the procedure described for the preparation of (SZ15TA3) in 44.2% yield. $^1$H-NMR (400 MHz, CDCl$_3$) δ: 8.84 (bs, 1H), 8.04 (d, J=7.2 Hz, 2H), 7.60 (d, J=7.6 Hz, 2H), 7.28 (dd, J=14.0, 7.2 Hz, 1H), 7.16 (bs, 6H), 6.97 (t, J=8.4 Hz, 1H), 6.91 (s, 2H), 6.55 (s, 1H), 4.36 (s, 1H), 4.33 (s, 1H), 3.70 (s, 6H), 3.22 (bs, 4H) ppm. $^{13}$C-NMR (100 MHz, CDCl$_3$) δ: 165.1, 162.5 (d, $^1J_{CF}$=226 Hz), 161.1, 140.3, 136.9, 136.2, 133.1, 133.0, 132.7, 131.3, 131.1, 129.6, 127.9, 126.5, 116.4 (d, $^2J_{CF}$=16.8 Hz), 115.1 (d, $^2J_{CF}$=22.5 Hz), 106.3, 106.0, 57.7, 55.8, 52.9, 49.1, 28.7 ppm. HRMS (ESI$^+$) for [M+H]$^+$; calculated: 629.13415. found: 629.13427 (error m/z=0.20 ppm).

4.14 Acylsulfonamide (SZ15TA6)

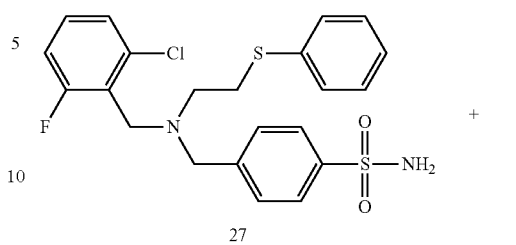

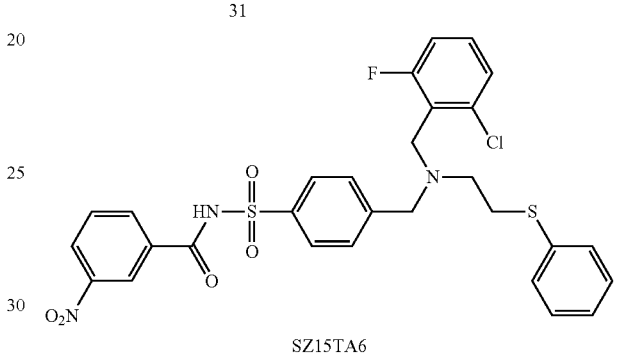

SZ15TA6

(SZ15TA6) was prepared starting from 27 and 31 using the procedure described for the preparation of (SZ15TA3) in 60.7% yield $^1$H-NMR (400 MHz, CDCl$_3$) δ: 8.63 (s, 1H), 8.24 (d, J=8 Hz, 2H), 8.17 (d, J=7.6 Hz, 2H), 8.05 (d, J=7 Hz, 3H), 7.64 (d, J=7 Hz, 2H), 7.54 (t, J=7 Hz, 1H), 7.28-7.23 (m, 2H), 7.14 (s, 6H), 7.02-6.93 (m, 2H), 4.36 (s, 2H), 4.32 (s, 2H), 3.24-3.21 (m, 4H) ppm. $^{13}$C-NMR (100 MHz, CDCl$_3$) δ: 163.5, 162.3 (d, $^1J_{CF}$=208 Hz), 160.8, 148.0, 139.8, 136.6, 134.1, 133.0, 132.6, 131.0, 130.5, 129.9, 129.3, 127.5, 126.2, 123.4, 116.6 (d, $^2J_{CF}$=18 Hz), 114.8 (d, $^2J_{CF}$=22 Hz), 57.5, 52.6, 48.8, 28.5 ppm. HRMS (ESI$^+$) for [M+Na]$^+$; calculated: 636.0800. found: 636.0804 (error m/z=0.53 ppm).

4.15 Acylsulfonamide (SZ15TA7)

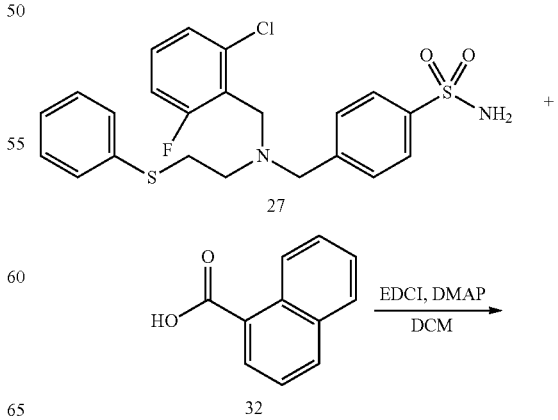

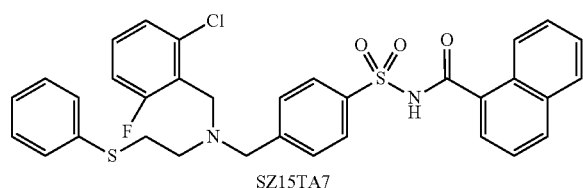

SZ15TA7

(SZ15TA7) was prepared starting from 27 and 32 using the procedure described for the preparation of (SZ15TA3) in 48.4% yield. $^1$H-NMR (400 MHz, CD$_3$OD) δ: 8.11 (d, J=8.4 Hz, 2H), 7.98 (d, J=8.4 Hz, 1H), 7.95 (d, J=8.8 Hz, 1H), 7.85 (d, J=8.4 Hz, 1H), 7.68-7.64 (m, 3H), 7.47 (d, J=8.0 Hz, 1H), 7.43 (d, J=9.2 Hz, 1H), 7.39-7.28 (m, 2H), 7.23-7.10 (m, 6H), 7.02 (t, J=8.8 Hz, 1H), 4.28 (s, 2H), 4.21 (s, 2H), 3.24-3.21 (m, 2H), 3.12-3.09 (m, 2H) ppm. $^{13}$C-NMR (100 MHz, CD$_3$OD) δ: 168.1, 162.3 (d, $^1J_{CF}$=249.6 Hz), 140.2, 136.5, 133.9, 132.3, 132.0, 130.9, 130.6, 130.5, 130.0, 129.2, 128.7, 127.3, 127.1, 126.9, 126.6, 126.0, 124.4 (d, $^3J_{CF}$=10.7 Hz), 114.5 (d, $^2J_{CF}$=22.9 Hz), 57.4, 53.3, 48.5, 28.7 ppm.

4.16 Acylsulfonamide (SZ15TA9)

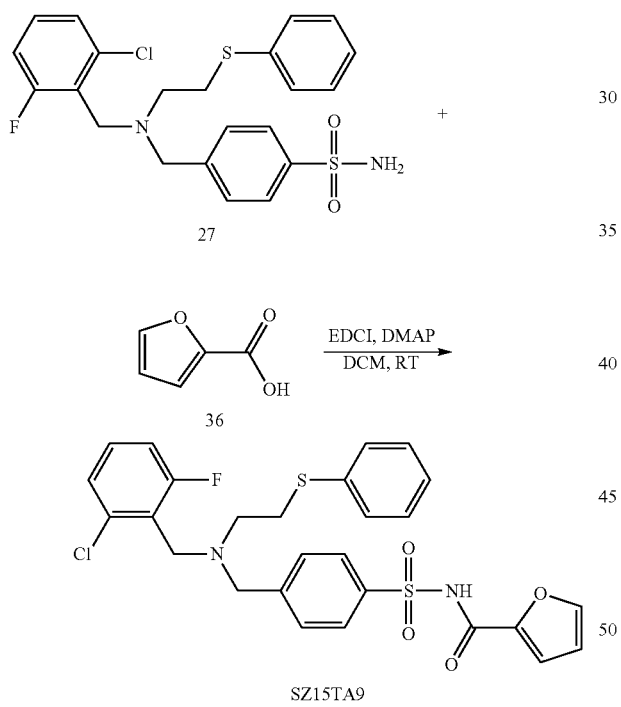

SZ15TA9

(SZ15TA9) was prepared starting from 27 and 36 using the procedure described for the preparation of (SZ15TA9) in 91.6% yield. $^1$H-NMR (400 MHz, CDCl$_3$) δ: 10.32 (s, 1H), 8.03 (d, J=8 Hz, 2H), 7.64 (d, J=8 Hz, 2H), 7.28-7.22 (m, 3H), 7.14-7.12 (m, 7H), 6.94 (t, J=9 Hz, 1H), 4.45 (s, 2H), 4.37 (s, 2H), 3.27 (s, 4H) ppm. $^{13}$C-NMR (100 MHz, CDCl$_3$) δ: 162.0 (d, $^1J_{CF}$=251 Hz), 160.9, 160.5, 155.1, 146.6, 144.7, 140.2, 136.5, 135.3, 132.9 (d, $^3J_{CF}$=9.6 Hz), 132.0, 131.3, 130.7, 129.2, 129.1, 127.7, 126.2, 118.5, 117.1, 115.5 (d, $^2J_{CF}$=17 Hz), 114.8 (d, $^2J_{CF}$=22.6 Hz), 114.3, 112.8, 57.4, 52.6, 48.8, 28.1 ppm. HRMS (ESI$^+$) for [M+H]$^+$; calculated: 559.0923. found: 559.0915 (error m/z=−1.31 ppm).

4.17 Acylsulfonamide (SZ15TA10)

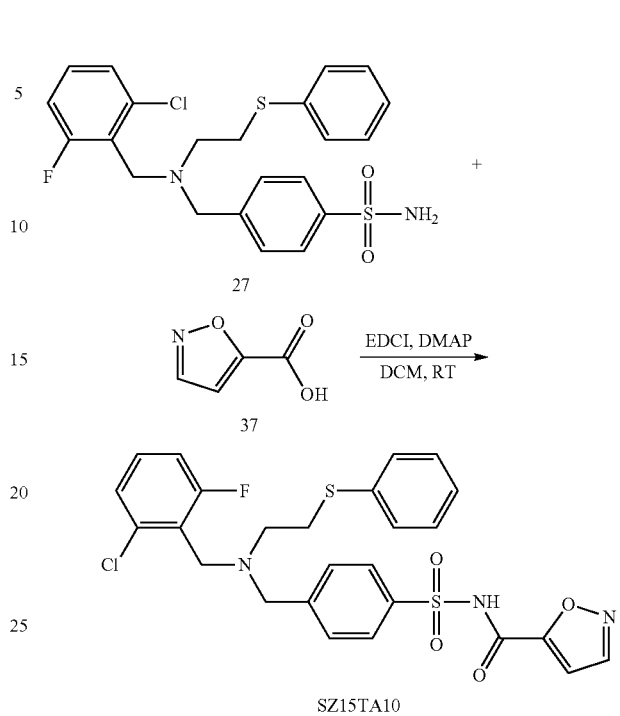

SZ15TA10

(SZ15TA10) was prepared starting from 27 and 37 using the procedure described for the preparation of (SZ15TA9) in 91.6% yield. $^1$H-NMR (400 MHz, CDCl$_3$) δ: 8.30 (s, 1H), 7.98 (d, J=8 Hz, 2H), 7.83 (bs, 1H), 7.54 (d, J=8 Hz, 2H), 7.18-7.10 (m, 7H), 6.99 (s, 1H), 6.91 (t, J=8.4 Hz, 1H), 4.06 (s, 2H), 4.02 (s, 2H), 3.13-3.11 (m, 2H), 2.97-2.95 (m, 2H) ppm. $^{13}$C-NMR (100 MHz, CDCl$_3$) δ: 162.2 (d, $^1J_{CF}$=250 Hz), 160.3, 153.4, 151.2, 141.9, 137.9, 136.4, 134.2, 130.9 (d, $^3J_{CF}$=9.6 Hz), 129.9, 129.7, 129.0, 128.7, 126.6, 125.8, 120.3 (d, $^2J_{CF}$=17.6 Hz), 114.3 (d, $^2J_{CF}$=23 Hz), 108.7, 57.5, 52.9, 49.0, 29.6 ppm. HRMS (ESI$^+$) for [M+H]$^+$; calculated: 560.0875. found: 560.0873 (error m/z=−0.34 ppm).

4.18 Acylsulfonamide (SZ17TA3)

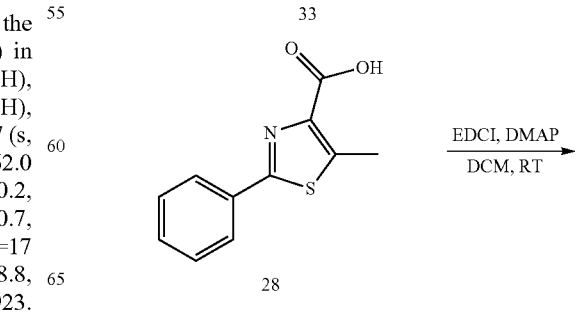

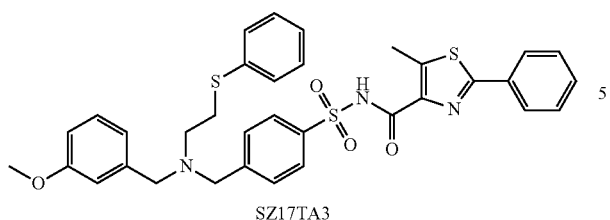

(SZ17TA3) was prepared starting from 33 and 28 using the procedure described for the preparation of (SZ15TA9) in 79.5% yield. $^1$H-NMR (400 MHz, CDCl$_3$) δ: 9.81 (s, 1H), 8.05 (d, J=8 Hz, 2H), 7.79 (d, J=7.2 Hz, 2H), 7.53 (d, J=7.6 Hz, 2H), 7.42-7.33 (m, 3H), 7.21-15 (m, 6H), 6.95 (s, 1H), 6.87 (d, J=8 Hz, 1H), 6.81 (d, J=7.2 Hz, 1H), 4.29 (s, 2H), 4.19 (s, 2H), 3.7 (s, 3H), 3.11-3.10 (m, 4H), 2.60 (s, 3H) ppm.

4.19 Acylsulfonamide (SZ3TA6)

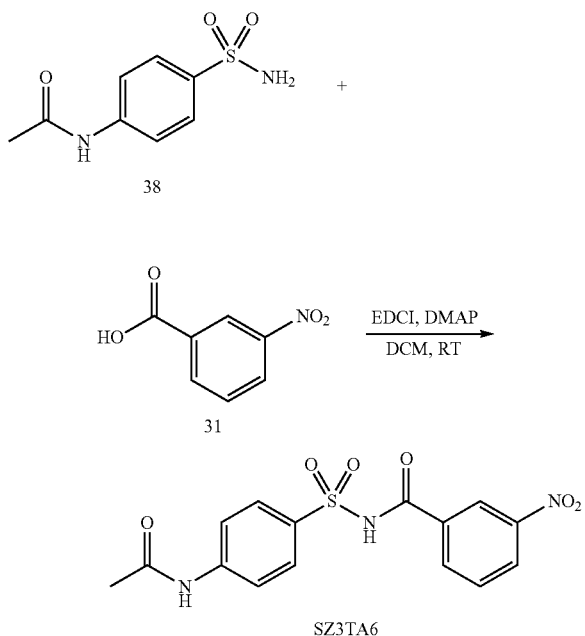

(SZ3TA6) was prepared starting from 38 and 31 using the procedure described for the preparation of (SZ15TA9) in 45.5% yield. $^1$H-NMR (250 MHz, acetone-d$_6$) δ: 8.61 (s, 1H), 8.31 (d, J=7.5 Hz, 1H), 8.22 (d, J=10 Hz, 1H), 7.9 (d, J=7.5 Hz, 2H), 7.75-7.64 (m, 3H), 1.99 (s, 3H) ppm. $^{13}$C-NMR (60 MHz, acetone-d$_6$) δ: 169.7, 149.2, 145.1, 135.2, 134.1, 131.1, 130.5, 128.0, 123.9, 119.1, 24.3 ppm.

4.20 Acylsulfonamide (SZ3TA9)

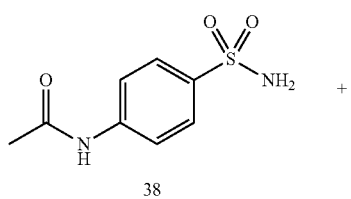

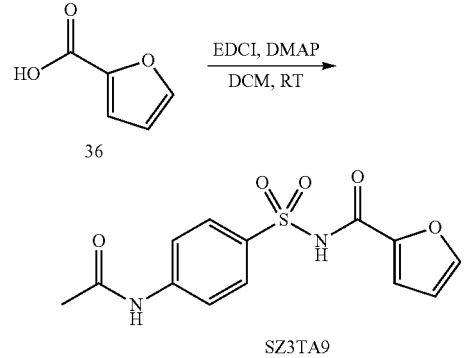

(SZ3TA9) was prepared starting from 38 and 36 using the procedure described for the preparation of (SZ15TA9) in 35.5% yield. $^1$H-NMR (400 MHz, CD$_3$OD) δ: 7.97 (d, J=8.8 Hz, 2H), 7.75 (d, J=8.8 Hz, 2H), 7.70 (d, J=1.2 Hz, 1H), 7.25 (d, J=1.2 Hz, 1H), 6.58 (dd, J=3.2, 1.6 Hz, 1H), 2.13 (s, 3H) ppm. $^{13}$C-NMR (100 MHz, CD$_3$OD) δ: 170.9, 156.4, 147.1, 145.6, 143.9, 133.8, 129.4, 118.9, 117.8, 112.4, 22.9 ppm. HRMS (ESI$^+$) for [M+H]$^+$; calculated: 309.05397. found: 309.05467 (error m/z=2.28 ppm).

4.21 Acylsulfonamide (SZ9TA7)

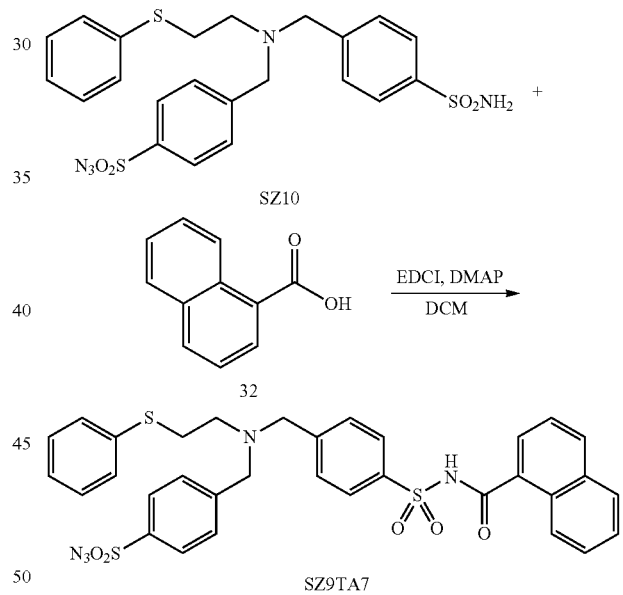

(SZ9TA7) was prepared starting from (SZ10) and 32 using the procedure described for the preparation of (SZ15TA9) in 69.3% yield. $^1$H-NMR (400 MHz, CDCl$_3$) δ: 8.44 (s, 1H), 7.96 (d, J=8.0 Hz, 2H), 7.73-7.71 (m, 3H), 7.57-7.55 (m, 3H), 7.35 (d, J=8.0 Hz, 2H), 7.15-6.95 (m, 10H), 3.37 (s, 2H), 3.31 (s, 2H), 2.86 (t, J=6.4 Hz, 2H), 2.50 (bs, 2H) ppm. $^{13}$C-NMR (100 MHz, CDCl$_3$) δ: 147.0, 143.5, 140.0, 136.8, 135.8, 133.4, 131.4, 130.4, 129.5, 128.9, 128.8, 128.7, 128.0, 127.7, 127.4, 127.1, 126.9, 126.1, 125.7, 124.4, 57.6, 57.4, 52.5, 31.2 ppm. HRMS (ESI$^+$) for [M+H]$^+$; calculated: 309.05397. found: 309.05467 (error m/z=2.28 ppm).

What is claimed is:

1. A process for the preparation of an acylsulfonamide (3), the process comprising reacting a thioacid (1) with a sulfonyl azide (2) in the presence of a protein of the Bcl-2 family, wherein the thioacid (1), the sulfonyl azide (2), and the acylsulfonamide (3) correspond to Formulae (1), (2), and (3):

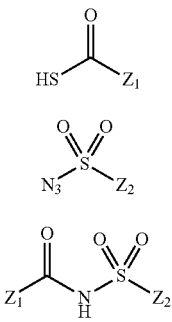

$Z_1$ is hydrocarbyl, substituted hydrocarbyl, heteroaryl, or heterocyclo; and $Z_2$ is hydrocarbyl, substituted hydrocarbyl, heteroaryl, or heterocyclo.

2. The process of claim 1 wherein $Z_1$ is aryl, substituted aryl, or heteroaryl.

3. The process of claim 1 wherein $Z_1$ has the formula:

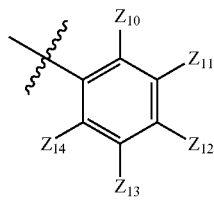

wherein
$Z_{10}$, $Z_{11}$, $Z_{12}$, $Z_{13}$, and $Z_{14}$ are independently hydrogen, hydroxyl, protected hydroxyl, halo, hydrocarbyl, substituted hydrocarbyl, heterocyclo, heteroaryl, alkoxy, alkenoxy, alkynoxy, aryloxy, arylalkoxy (heterocyclo)alkoxy, trihaloalkoxy, amino, amido, or cyano, or two of $Z_{10}$, $Z_{11}$, $Z_{12}$, $Z_{13}$, and $Z_{14}$, together with the carbon atoms to which they are attached, form a fused carbocyclic (e.g., napthyl) or heterocyclic ring.

4. The process of claim 3 wherein $Z_{10}$, $Z_{11}$, $Z_{12}$, $Z_{13}$, and $Z_{14}$ are independently hydrogen, amino, alkoxy, nitro, or trihalomethoxy.

5. The process of claim 1 wherein $Z_1$ has the formula:

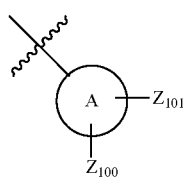

wherein
A is phenyl or a five- or six-membered aromatic carbocyclic or heterocyclic ring wherein from one to three carbon atoms may be replaced by a heteroatom selected from N, O, or S, and wherein A is substituted with $Z_{100}$ and $Z_{101}$ through ring carbon atoms or ring heteroatoms, and $Z_{100}$ and $Z_{101}$ are independently hydrogen, hydrocarbyl, substituted hydrocarbyl, heterocyclo, alkoxy, alkenoxy, alkynoxy, aryloxy, heterocyclo(alkoxy), or halo.

6. The process of claim 1 wherein $Z_1$ is substituted or unsubstituted furyl, thienyl, pyridyl, oxazolyl, isoxazolyl, imidazolyl, pyridyl, pyrimidyl, purinyl, triazolyl, or thiazolyl.

7. The process of claim 1 wherein $Z_1$ is substituted or unsubstituted morpholino, pyran, tetrahydropyran, piperazinyl, piperidinyl, tetrahydropyridinyl, pyrrolidinyl, pyrrolinyl, 1,4-diazepanyl, or azepinyl.

8. The process of claim 1 wherein $Z_1$ is —$(CH_2)_x$—$Z_{102}$ wherein $Z_{102}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3.

9. The process of claim 1 wherein $Z_1$ is heteroaryl, heterocyclo, or has the formula:

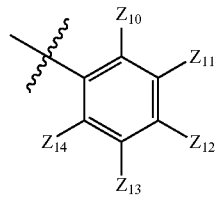

wherein
$Z_{10}$, $Z_{11}$, $Z_{12}$, $Z_{13}$, and $Z_{14}$ are independently hydrogen, amino, alkoxy, nitro, or trihalomethoxy (e.g., trifluoromethoxy); or $Z_1$ is —$(CH_2)_x$—$Z_{102}$ wherein $Z_{102}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3.

10. The process of any one of claims 1-9 wherein $Z_2$ is substituted or unsubstituted alkyl, alkenyl, alkynyl, aryl, alkaryl, or aralkyl.

11. The process of any one of claims 1-9 wherein $Z_2$ has the formula:

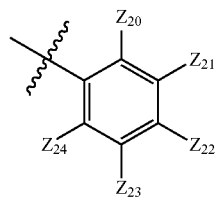

wherein
$Z_{20}$, $Z_{21}$, $Z_{22}$, $Z_{23}$, and $Z_{24}$ are independently hydrogen, halo, hydrocarbyl, substituted hydrocarbyl, alkoxy, alkenoxy, alkynoxy, aryloxy, nitro, cyano, amino, or amido, or two of $Z_{20}$, $Z_{21}$, $Z_{22}$, $Z_{23}$, and $Z_{24}$, together with the carbon atoms to which they are attached, form a fused carbocyclic or heterocyclic ring.

12. The process of claim 11 wherein $Z_{20}$, $Z_{21}$, $Z_{22}$, $Z_{23}$, and $Z_{24}$ are independently alkyl, substituted alkyl, amino, alkoxy, alkenoxy, alkynoxy, or aryloxy.

13. The process of any one of claims 1-10 wherein $Z_2$ is phenyl, substituted phenyl, napthyl, or substituted napthyl.

14. The process of any one of claims 1-10 wherein $Z_2$ may be —$(CH_2)_x$—$Z_{200}$ wherein $Z_{200}$ is hydrogen, hydroxyl, protected hydroxyl, heterocyclo, amino, amido, alkoxy, aryloxy, cyano, nitro, thiol, or an acetal, ketal, ester, ether, or thioether, and x is 1, 2, or 3.

15. The process of any one of claims 1-9 wherein $Z_2$ is substituted or unsubstituted furyl, thienyl, pyrrolyl, oxazolyl, imidazolyl, pyridyl, pyrimidyl, purinyl, triazolyl, or thiazolyl.

16. The process of any one of claims 1-9 wherein $Z_2$ is substituted or unsubstituted morpholino, pyran, tetrahydropyran, piperazinyl, piperidinyl, tetrahydropyridinyl, pyrrolidinyl, pyrrolinyl, 1,4-diazepanyl, or azepinyl.

17. The process of any one of claims 1-16 wherein the protein is selected from Bcl-2, Bcl-$X_L$, and Mcl-1.

18. The process of any one of claims 1-17 wherein the protein is Bcl-$X_L$.

19. The process of any one of claims 1-17 wherein the protein is Mcl-1.

* * * * *